United States Patent [19]

Lewicki et al.

[11] Patent Number: 5,212,286

[45] Date of Patent: * May 18, 1993

[54] ATRIAL NATRIURETIC/VASODILATOR PEPTIDE COMPOUNDS

[75] Inventors: John A. Lewicki, Sunnyvale; Robert M. Scarborough, Jr., Hayward, both of Calif.

[73] Assignee: Scios Nova Inc., Mountain View, Calif.

[*] Notice: The portion of the term of this patent subsequent to Aug. 16, 2005 has been disclaimed.

[21] Appl. No.: 870,795

[22] Filed: Jun. 5, 1986

Related U.S. Application Data

[63] Continuation-in-part of Ser. No. 766,030, May 8, 1985, Pat. No. 4,764,504, which is a continuation-in-part of Ser. No. 602,117, Apr. 9, 1984, Pat. No. 4,618,600, and a continuation-in-part of Ser. No. 616,488, Jun. 1, 1984, abandoned.

[51] Int. Cl.$^5$ .......................... C07K 7/08; C07K 7/10
[52] U.S. Cl. .................................. 530/324; 530/325; 530/326; 530/350
[58] Field of Search ................. 530/324, 325, 326, 350

[56] References Cited

U.S. PATENT DOCUMENTS

| | | | |
|---|---|---|---|
| 4,496,544 | 1/1985 | Needleman | 530/325 |
| 4,557,864 | 12/1985 | Needleman | 530/325 |
| 4,607,023 | 8/1986 | Thibault et al. | 530/326 |
| 4,609,725 | 9/1986 | Brady et al. | 530/325 |
| 4,618,600 | 10/1986 | Johnson et al. | 530/325 |
| 4,652,549 | 3/1987 | Blaine | 514/13 |
| 4,656,158 | 4/1987 | Matsuo et al. | 530/324 |
| 4,657,891 | 4/1987 | Matsuo et al. | 530/304 |
| 4,663,437 | 5/1987 | de Bold | 530/324 |
| 4,670,540 | 6/1987 | Sakakibara | 530/326 |
| 4,673,732 | 6/1987 | Kiso et al. | 530/327 |
| 4,716,147 | 12/1987 | Tjoeng et al. | 530/325 |
| 4,721,704 | 1/1988 | Chang et al. | 514/13 |
| 4,757,048 | 7/1988 | Lewichi et al. | 530/325 |
| 4,764,504 | 8/1988 | Johnson et al. | 514/12 |

FOREIGN PATENT DOCUMENTS 0116784 12/1983 European Pat. Off. ............ 530/324
0271041 6/1989 European Pat. Off. .

OTHER PUBLICATIONS

De Bold et al., (1981) Life Science 28:89–94.
Garcia et al., (1982) Experientia 38:1071–1073.
Currie et al., (1983) Science 221:71–73.
Flynn et al., (1983) Biochem. Biophys. Res. Commun. 117:859–865.
Currie et al., (1984) Science 223:67–69.
Kangawa et al., (1984) Biochem. Biophys. Res. Commun. 118:131–139.
Kangawa et al., (1984) Biochem. Biophys. Res. Commun. 119:933–940.
Seidman et al., (1984) Science 225:324–326.
Flynn et al., (1983) Biochemical and Biophysical Research Communications 117(3):859–862.
Cantin et al., (1984) Biological Abstracts 78(8):6587–6588, abstract No. 58551.
Dayoff, M., Atlas of Protein Sequence and Structure, vol. 5, 89–99, 1972.
Chem. Abstr. vol. 105, (1986) 153554.
Chem. Abstr. vol. 105, (1986) 60954.
Chem. Abstr. vol. 106, (1987) 48656.
Chem. Abstr. vol. 105, (1986) 35761.

Primary Examiner—Merrell C. Cashion, Jr.
Assistant Examiner—Susan M. Perkins
Attorney, Agent, or Firm—Morrison & Foerster

[57] ABSTRACT

Methods, compounds and compositions are provided for inducing natriuresis, diuresis and vasodilatation in mammalian hosts by administering atrial natriuretic/vasodilator peptides to said host. Also provided are methods for producing such peptide compounds.

1 Claim, 22 Drawing Sheets

```
        10         20         30         40         50         60         70
GGATCCATTT GTCTCGGGCT GCTGGCTGCC TGCCATTTCC TCCTCTCCAC CCTTATTTGG AGGCCCTGAC 80         90        100        110        120        130        140
AGCTGAGGCC ACAAACAAAC CAGGGGAGCT GGGCACCAGC CAAGCGTCAC CCTCTGTTTC CCCGCACGGG 150        160        170        180        190        200        210
TACCAGCGTC GAGGAGAAAG AATCCTGAGG CACGGCGGTG AGATAACCAA GGACTCTTTT TTACTCTTCT 220        230        240        250        260        270        280
CACACCTTTG AAGTGGGAGC CTCTTGAGTC AAATCAGTAA GAATGCGGCT CTTGCAGCTG AGGGTCTGGG 290        300        310        320        330        340        350
GGGCTGTTGG GGCTGCCCAA GGCAGAGAGG GGCTGTGACA AGCCCTGCGG GATGATAACT TTAAAAGGGC 360        370        380        390        400        410        420
ATCTCCTGCT GGCTTCTCAC TTGGCAGCTT TATCACTGCA AGTGACAGAA TGGGGAGGGT TCTGTCTCTC 430        440        450        460        470        480        490
CTGCGTGCTT GGAGAGCTGG GGGGCTATAA AAAGAGGCGG CACTGGGCAG CTGGGAGACA GGGACAGACG 500        510        520        530        540        550        560
TAGGCCAAGA GAGGGGAACC AGAGAGGAAC CAGAGGGGAG AGACAGAGCA GCAAGCAGTG GATTGCTCCT 570                   588                   603
TGACGACGCC AGC ATG AGC TCC TTC TCC ACC ACC ACC GTG AGC TTC CTC CTT TTA
           MET Ser Ser Phe Ser Thr Thr Thr Val Ser Phe Leu Leu Leu
            1

618                   633                   648                   663
CTG GCA TTC CAG CTC CTA GGT CAG ACC AGA GCT AAT CCC ATG TAC AAT GCC GTG
Leu Ala Phe Gln Leu Leu Gly Gln Thr Arg Ala Asn Pro MET Tyr Asn Ala Val
                                                26

678                   693        706        716        726        736
TCC AAC GCA GAC CTG ATG GAT TTC AAG GTAGGGCCAG GAAAGCGGGT GCAGTCTGGG GCCAGGGGGC
Ser Asn Ala Asp Leu MET Asp Phe Lys 746        756        766        776        786        796        806
TTTCTGATGC TGTGCTCACT CCTCTTGATT TCCTCCAAGT CAGTGAGGTT TATCCCTTTC CCTGTATTTT 816                    833                   848
CCTTTTCTAA AG AAT TTG CTG GAC CAT TTG GAA GAA AAG ATG CCT TTA GAA GAT
              Asn Leu Leu Asp His Leu Glu Glu Lys MET Pro Leu Glu Asp
                                            50

863                   878                   893                   908
GAG GTC GTG CCC CCA CAA GTG CTC AGT GAG CCG AAT GAA GAA GCG GGG GCT GCT
Glu Val Val Pro Pro Gln Val Leu Ser Glu Pro Asn Glu Glu Ala Gly Ala Ala 923                   938                   953                   968
CTC AGC CCC CTC CCT GAG GTG CCT CCC TGG ACC GGG GAA GTC AGC CCA GCC CAG
Leu Ser Pro Leu Pro Glu Val Pro Pro Trp Thr Gly Glu Val Ser Pro Ala Gln 983                   998                  1013
AGA GAT GGA GGT GCC CTC GGG CGG GGC CCC TGG GAC TCC TCT GAT CGA TCT GCC
Arg Asp Gly Gly Ala Leu Gly Arg Gly Pro Trp Asp Ser Ser Asp Arg Ser Ala
                                100

1028                  1043                  1058                  1073
CTC CTA AAA AGC AAG CTG AGG GCG CTG CTC ACT GCC CCT CGG AGC CTG CGG AGA
Leu Leu Lys Ser Lys Leu Arg Ala Leu Leu Thr Ala Pro Arg Ser Leu Arg Arg
                                                                     127
```

FIG._1A. SHEET I

```
                 1088                    1103                  1118
TCC AGC TGC TTC GGG GGC AGG ATG GAC AGG ATT GGA GCC CAG AGC GGA CTG GGC
Ser Ser Cys Phe Gly Gly Arg MET Asp Arg Ile Gly Ala Gln Ser Gly Leu Gly 1133                    1155      1165      1175      1185      1195
TGT AAC AGC TTC CGG GTAAGAGGAA CTGGGGATGG AAATGGGATG GGATGGACAC TACTGGGAGA
Cys Asn Ser Phe Arg
              150
     1205      1215      1225      1235      1245      1255      1265
CACCTTCAGC AGGAAAGGGA CCAATGCAGA AGCTCATTCC CTCTCAAGTT TCTGCCCCAA CACCCAGAGT 1275      1285      1295      1305      1315      1325      1335
GCCCCATGGG TGTCAGGACA TGCCATCTAT TGTCCTTAGC TAGTCTGCTG AGAAAATGCT TAAAAAAAAA 1345      1355      1365      1375      1385      1395      1405
AGGGGGGGGG CTGGGCACGG TCGTCACGCC TGTAATCCCA GCACTTTGGG AGGCCAGGCA GCGGATCATG 1415      1425      1435      1445      1455      1465      1475
AGGTCAAGAG ATCAAGACTA TCCTGGCCAA CATGGTGAAA CCCCAGCTCT ACTAAAAATA CAAAAATTAG 1485      1495      1505      1515      1525      1535      1545
CTGGGTGTGT GGCGGGCACC TGTACTCTCA GCTACTTGGG AGGCTGAGGC AGGAGAATCA CTTGAACCCA 1555      1565      1575      1585      1595      1605      1615
GGAGGCAGAG GTTGCAGTGA GCAGAGATCA CGCCACTGCA GTCCAGCCTA GGTGATAGAG CGAGACTGTC 1625      1635      1645      1655      1665      1675      1685
TCAAAAAAAA AAAAAAAAGG CCAGGCGCGG TGGCTCACGC CTGTAATCCC AGCGCTTTGG GAGGCCAAGG 1695      1705      1715      1725      1735      1745      1755
CGGGTGGATC ACGAGGTCAG GAGATGGAGA CCATCCTGGC TAACACGGTG AAACCCCGTC TCTACTAAAA 1765      1775      1785      1795      1805      1815      1825
ATACAAAAAA TTAGCCAGGC GTGGTGGCCA GGCGCCTGTA AGTCCTAGCT ACTCCGGAGC TGAGGCAGGA 1835      1845      1855      1865      1875      1885      1895
GAATGGCCGT GAACCCGGGA GGCGGAGCTT GCAGTGAGCA GAGATGGCAC CACTGCACTC CAGCCTGGGC 1905      1915      1925      1935      1945      1955      1965
GACAGAGCAA GACTCCGTCT CAAAAAAAAA AAAAAAAAAA GCAACTGCCA CTAGCACTGG GAAATTAAAA 1975      1985      1995      2005      2015      2025      2035
TATTCATAGA GCCAAGTTAT CTTTGCATGG CTGATTAGCA GTTCATATTC CTCCCCAGAA TTGCAAGATC 2045      2055      2065      2075      2085      2095      2105
CTGAAGGGCT TAAGTGAAAT TTACTCTGAT GAGTAACTTG CTTATCAATT CATGAAGCTC AGAGGGTCAT 2115      2125      2135      2145      2155      2165      2175
CAGGCTGGGG TGGGGCCGG TGGGAAGCAG GTGGTCAGTA ATCAAGTTCA GAGGATGGGC ACACTCATAC 2185      2195      2205      2215      2225      2235
ATGAAGCTGA CTTTTCCCAG GACAGCCAGG TCACCAAGCC AGATATGTCT GTGTTCTCTT TGCAG 2262      2272      2282      2292      2302
TAC TGA AGA TAA CAGCCAGGGA GGACAAGCAG GGCTGGGCCT AGGGACAGAC TGCAAGAGGC
Tyr     Arg
151
```

FIG._1A. SHEET II

```
         2312       2322       2332       2342       2352       2362       2372
TCCTGTCCCC TGGGGTCTCT GCTGCATTTG TGTCATCTTG TTGCCATGGA GTTGTGATCA TCCCATCTAA 2382       2392       2402       2412       2422       2432       2442
GCTGCAGCTT CCTGTCAACA CTTCTCACAT CTTATGCTAA CTGTAGATAA AGTGGTTTGA TGGTGACTTC 2452       2462       2472       2482       2492       2502       2512
CTCGCCTCTC CCACCCCATG CATTAAATTT TAAGGTAGAA CCTCACCTGT TACTGAAAGT GGTTTGAAAG 2522       2532       2542       2552       2562       2572       2582
TGAATAAACT TCAGCACCAT GGACAGAAGA CAAATGCCTG CGTTGGTGTG CTTTCTTTCT TCTTGGGAAG

AGAATTC
```

FIG._IA. SHEET III

```
  1
  G GCA TTC CAG CTC CTA GGT CAG ACC AGA GCT AAT CCC ATG TAC AAT GCC GTG TCC AAC GCA GAC CTG ATG GAT
    Ala Phe Gln Leu Leu Gly Gln Thr Arg Ala Asn Pro Met Tyr Asn Ala Val Ser Asn Ala Asp Leu Met Asp
    16                                    26                                 50
                                                    100
  TTC AAG AAT TTG CTG GAC CAT TTG GAA GAA AAG ATG CCT TTA GAA GAT GAG GTC GTG CCC CCA CAA GTG CTC
  Phe Lys Asn Leu Leu Asp His Leu Glu Glu Lys Met Pro Leu Glu Asp Glu Val Val Pro Pro Gln Val Leu
                                        50
                            150                                        200
  AGT GAG CCG AAT GAA GAA GCG GGG GCT GCT CTC AGC CCC CTC CCT GAG GTG CCT CCC TGG ACC GGG GAA GTC
  Ser Glu Pro Asn Glu Glu Ala Gly Ala Ala Leu Ser Pro Leu Pro Glu Val Pro Pro Trp Thr Gly Glu Val
                                                          250
  AGC CCA GCC CAG AGA GAT GGA GGT GCC CTC GGG CTG CTC ACT GCC CCT CGG GGC CCC TGG GAC TCC TCT GAT CGA TCT GCC CTC CTA
  Ser Pro Ala Gln Arg Asp Gly Gly Ala Leu Gly Leu Leu Thr Ala Pro Arg Gly Pro Trp Asp Ser Ser Asp Arg Ser Ala Leu Leu
              300                                                 350
  AAA AGC AAG CTG AGG GCG CTG AGC GGA CTG GGC TGT AAC AGC TTC AGG AGA TCC AGC AGC TGC TTC GGG GGC AGG ATG
  Lys Ser Lys Leu Arg Ala Leu Arg Ala Ser Gly Leu Gly Cys Asn Ser Phe Arg Arg Ser Ser Cys Phe Gly Gly Arg Met
                                              400
  GAC AGG ATT GGA GCC CAG AGC GGA GCC CAG AGC GGA CTG GGC TGT AAC AGC TTC CGG TAC TGA agataacagc cagggaggac
  Asp Arg Ile Gly Ala Gln Ser Gly                                   Tyr
              450                                           151
                                                                500
  aagcaggct gggcctaggg acagactgca agaggctcct gtcccctggg gtctctgctg catttgtgtc atcttgttgc catggagttg
                                                                                  600
  tgatcatccc atctaagctg cagcttcctg tcaacacttc tcacatctta tgctaactgt agataaagtg gtttgatggt gacttcctcg
                                  650                                                              700
  cctctcccac cccatgcatt aaatttaag gtagaactc acctgttact gaaagtggtt tgaaagtgaa taaacttcag caccatggac
```

FIG.\_1b.

```
         10          20          30          40          50          60          70
GAGGAAGAAG CCCTTGGTGA TGGAGAGAAA CCAGAGAGTG AGCCGAGACA GCAAACATCA GATCGTGCCC
                         ⬆

80                              99                      114
CGACCCACGC CAGC ATG GGC TCC TTC TCC ATC ACC AAG GGC TTC TTC CTC TTC CTG
            MET Gly Ser Phe Ser Ile Thr Lys Gly Phe Phe Leu Phe Leu
             1

129                     144                     159                     174
GCC TTT TGG CTC CCA GGC CAT ATT GGA GCA AAT CCC GTA TAC AGT GCG GTG TCC
Ala Phe Trp Leu Pro Gly His Ile Gly Ala Asn Pro Val Tyr Ser Ala Val Ser
                                         25
        189                     204                     219                     234
AAC ACA GAT CTG ATG GAT TTC AAG AAC CTG CTA GAC CAC CTG GAG GAG AAG ATG
Asn Thr Asp Leu MET Asp Phe Lys Asn Leu Leu Asp His Leu Glu Glu Lys MET
                                                                         50
             249                     264                     279
CCG GTA GAA GAT GAG GTC ATG CCT CCG CAG GCC CTG AGC GAG CAG ACC GAT GAA
Pro Val Glu Asp Glu Val MET Pro Pro Gln Ala Leu Ser Glu Gln Thr Asp Glu 294                     309                     324                     339
GCG GGG GCG GCA CTT AGC TCC CTC TCT GAG GTG CCT CCC TGG ACT GGG GAA GTC
Ala Gly Ala Ala Leu Ser Ser Leu Ser Glu Val Pro Pro Trp Thr Gly Glu Val 354                     369                     384
AAC CCG TCT CAG AGA GAT GGA GGT GCT CTC GGG CGC GGC CCC TGG GAC CCC TCC
Asn Pro Ser Gln Arg Asp Gly Gly Ala Leu Gly Arg Gly Pro Trp Asp Pro Ser
                                                         100
399                     414                     429                     444
GAT AGA TCT GCC CTC TTG AAA AGC AAA CTG AGG GCT CTG CTC GCT GGC CCT CGG
Asp Arg Ser Ala Leu Leu Lys Ser Lys Leu Arg Ala Leu Leu Ala Gly Pro Arg 459                     474                     489                     504
AGC CTG CGA AGG TCA AGC TGC TTC GGG GGT AGG ATT GAC AGG ATT GGA GCC CAG
Ser Leu Arg Arg Ser Ser Cys Phe Gly Gly Arg Ile Asp Arg Ile Gly Ala Gln
         _____
        126 519                    534                     553         563
AGC GGA CTA GGC TGC AAC AGC TTC CGG TAC CGA AGA TAA CAGCCAAATC TGCTCGAGCA
Ser Gly Leu Gly Cys Asn Ser Phe Arg Tyr Arg Arg
_____
        573         583         593      150 603 152  613         623         633
GATCGCAAAA GATCCCAAGC CTTGCGGTGT GTCACACAGC TTGGTCGCAT TGCCACTGAG AGGTGGTGAA 643         653         663         673         683         693         703
TACCCTCCTG GAGCTGCAGC TTCCTGTCTT CATCTATCAC GATCGATGTT AAGTGTAGAT GAGTGGTTTA 713         723         733         743         753         763         773
GTGAGGCCTT ACCTCTCCCA CTCTGCATAT TAAGGTAGAT CCTCACCCCT TTCAGAAAGC AGTTGGAAAA 783         793         803
AAATAAATCC GAATAAACTT CAGCACCACG GAC
_____    ⬆
```

FIG._2.

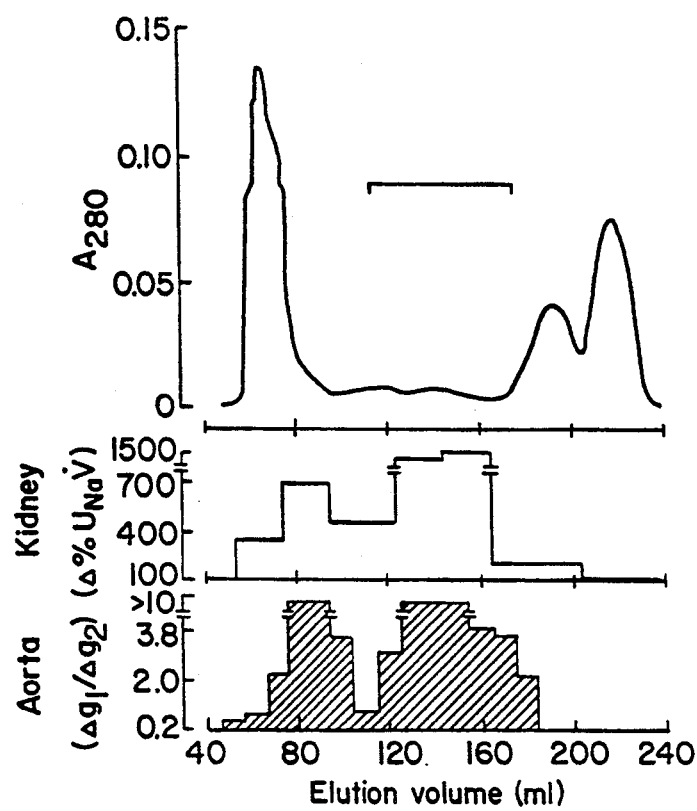
FIG._3A.
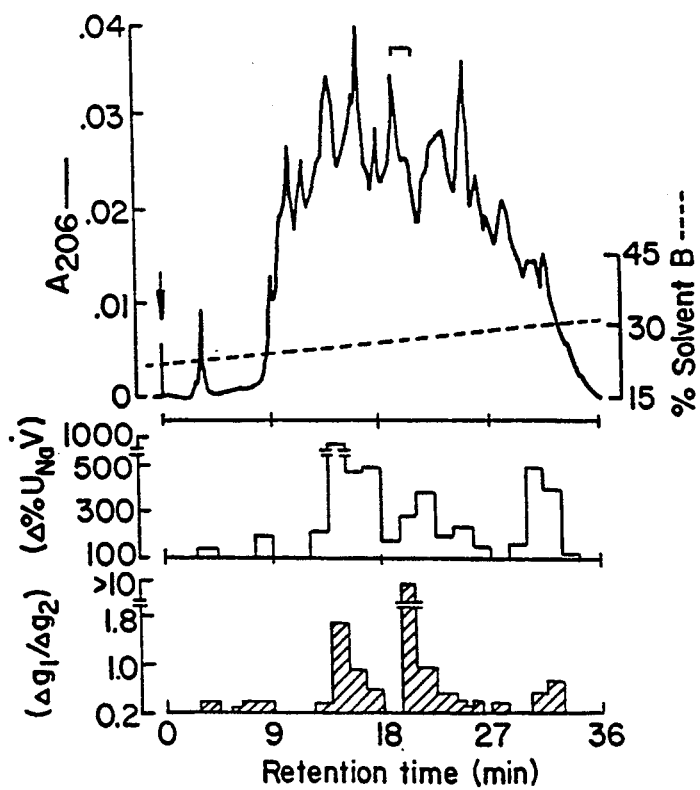
FIG._3B.

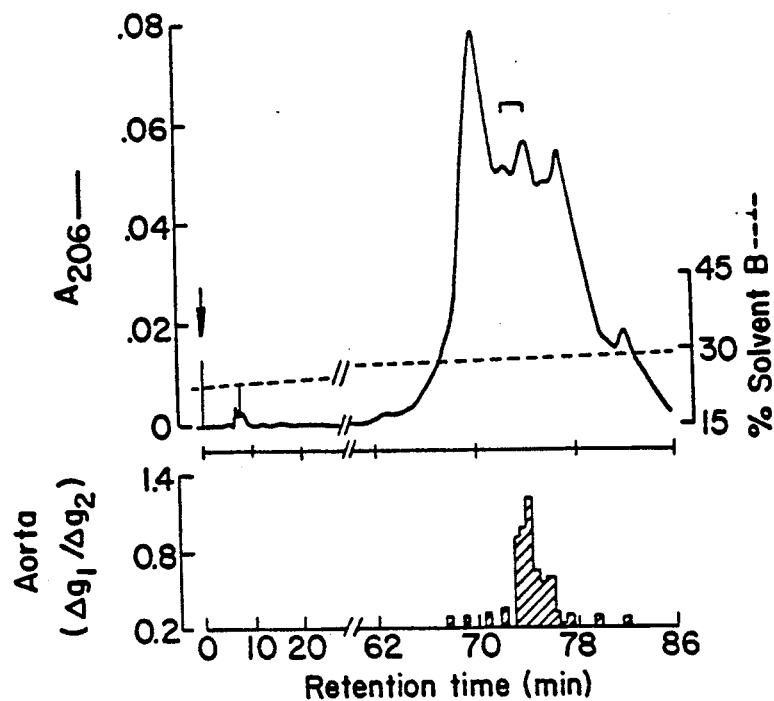
FIG._3C.
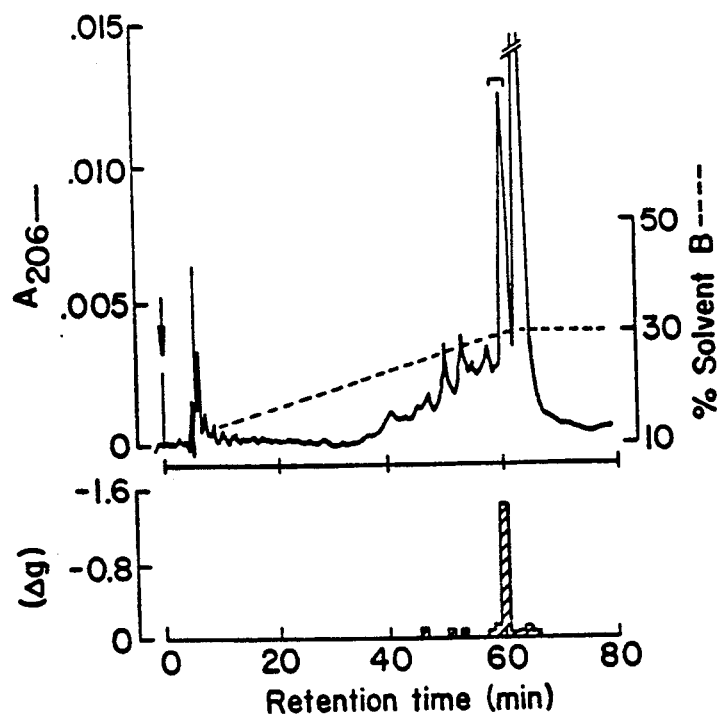
FIG._3D.

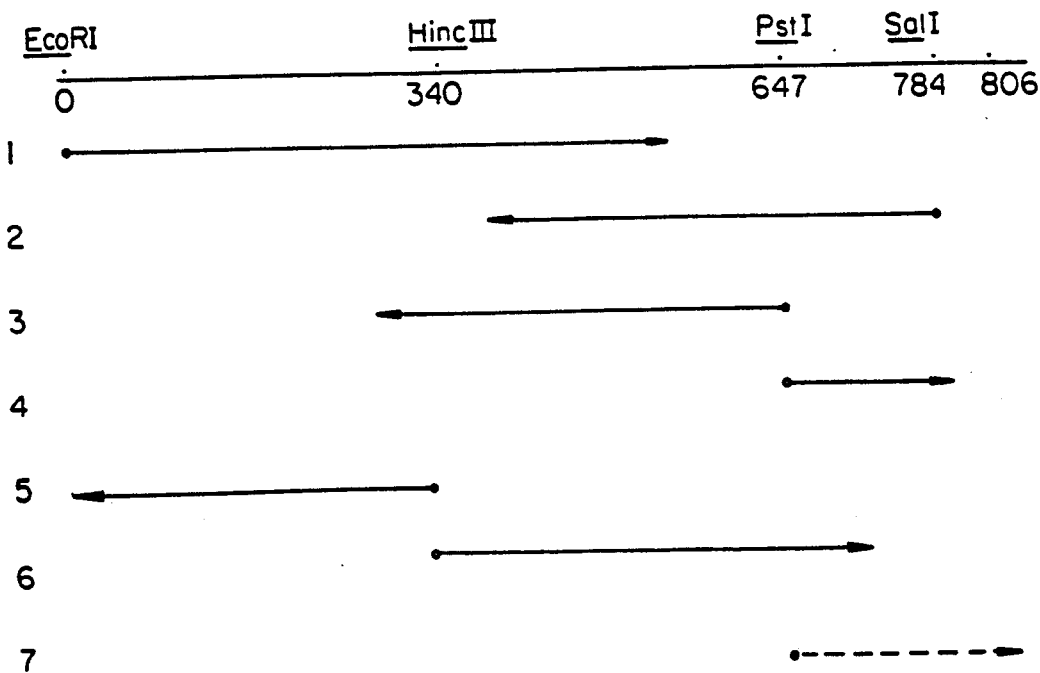

Lane
1 2
FIG._6A.
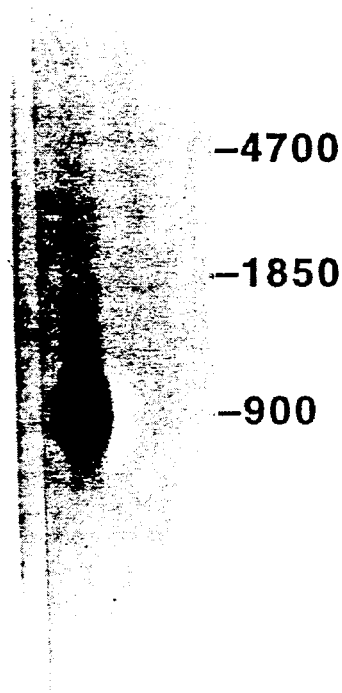
—4700
—1850
—900
FIG._6B.
—25K
—18K
—12K
FIG._6C.
FIG._6D.
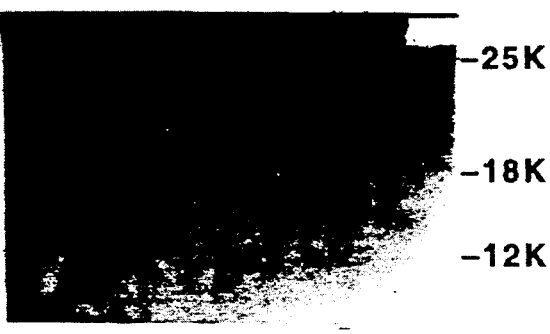
—25K
—18K
—12K
FIG._6E.

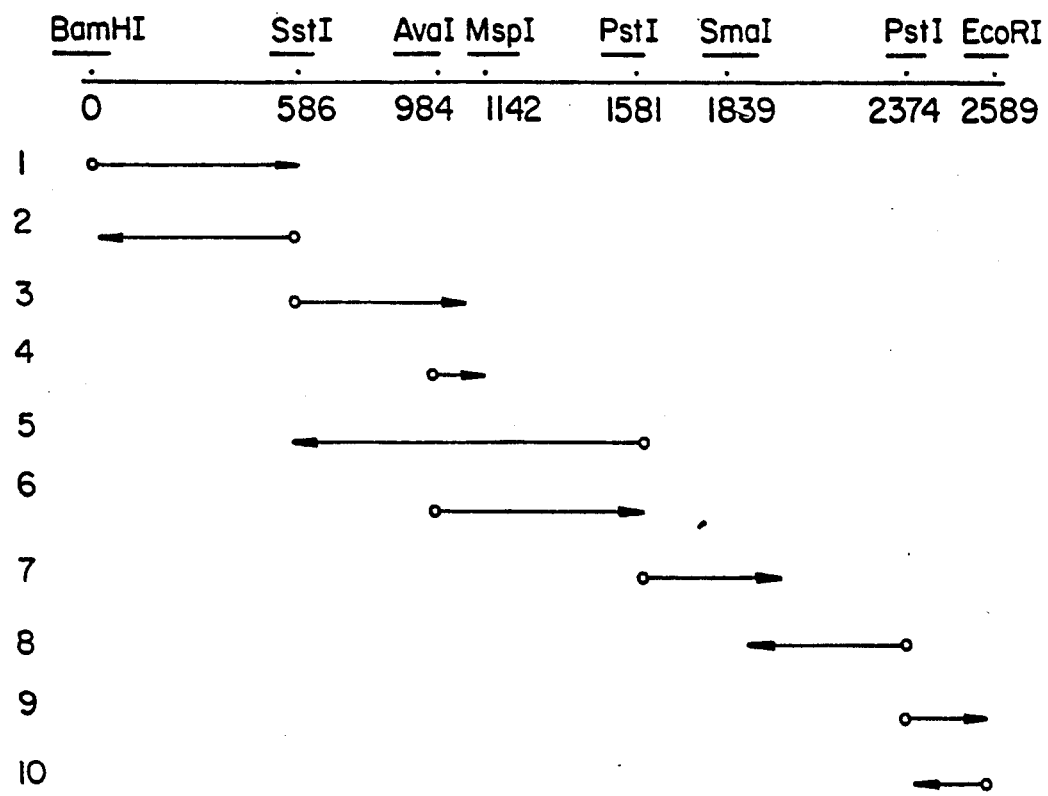
FIG._7.
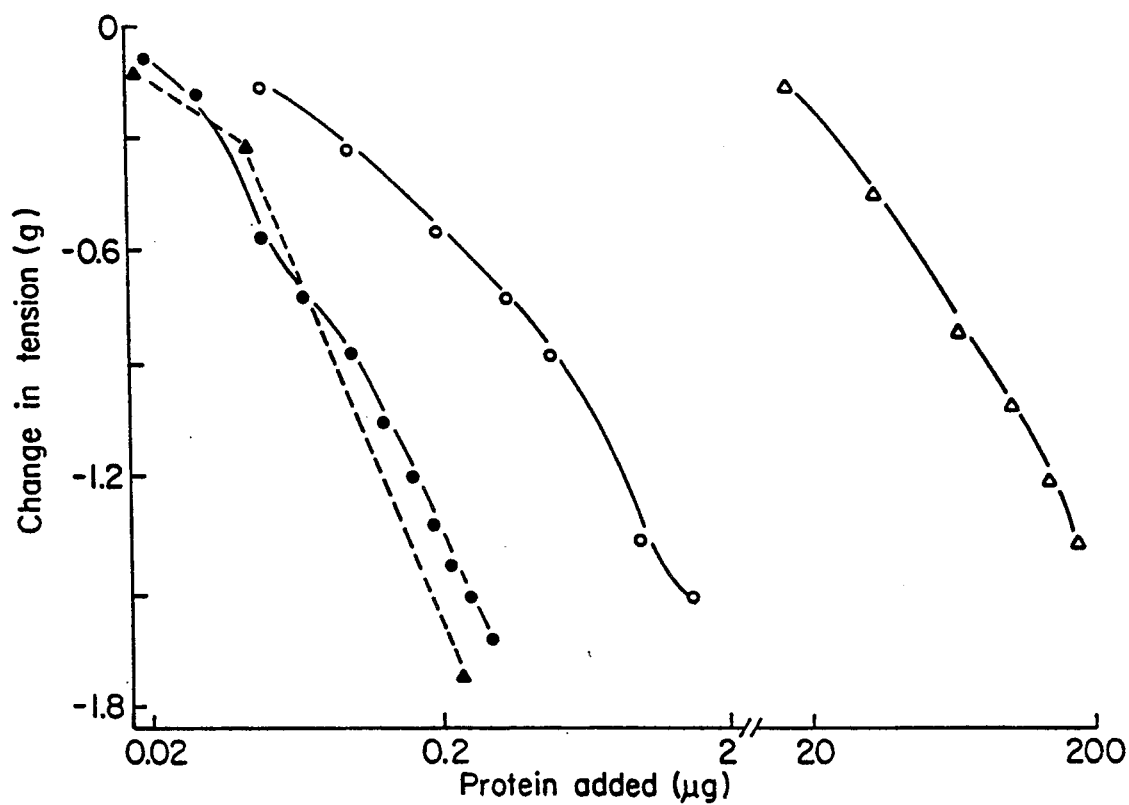
FIG._8.

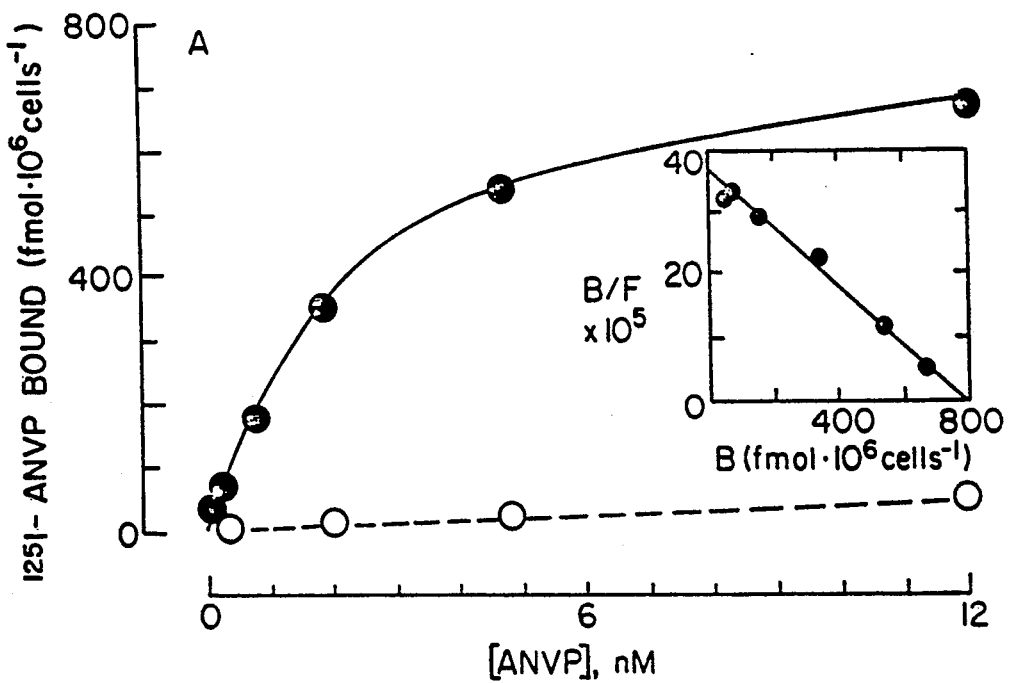
FIG._9A.
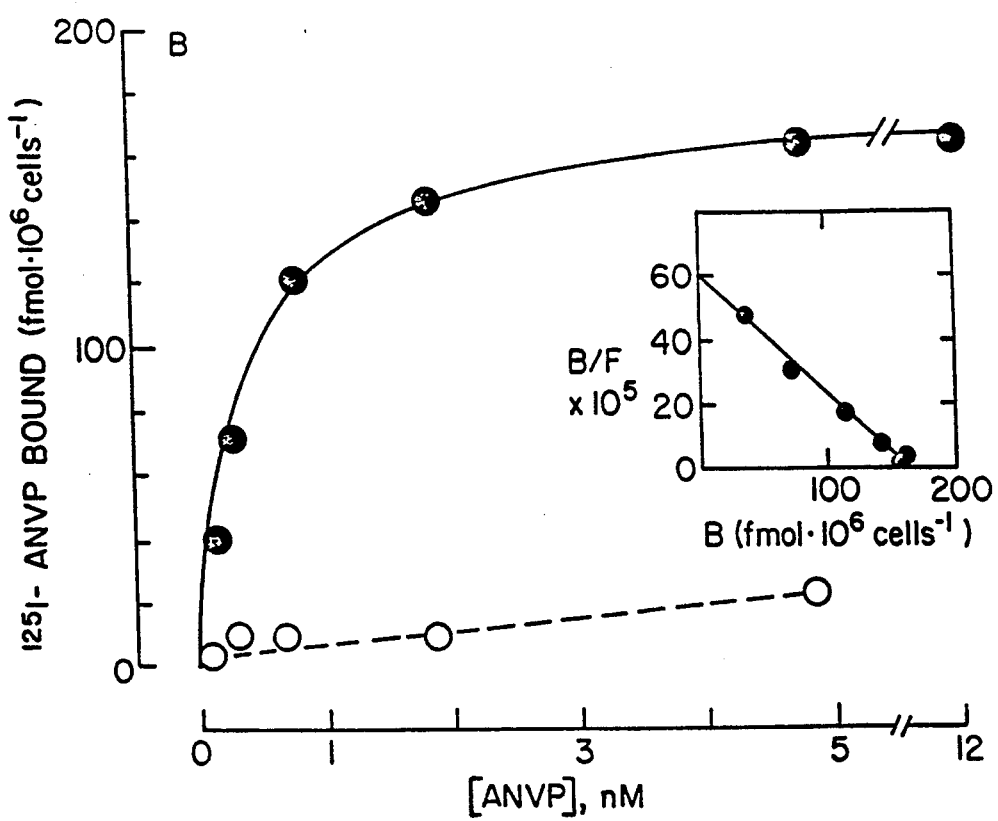
FIG._9B.

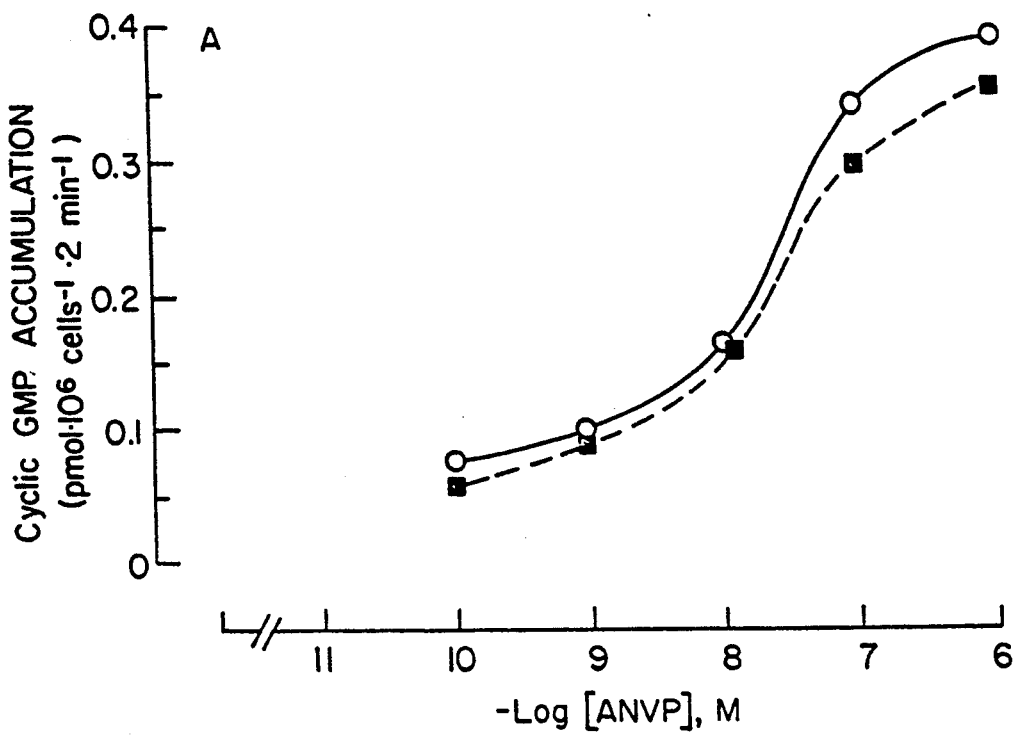
FIG._10A.
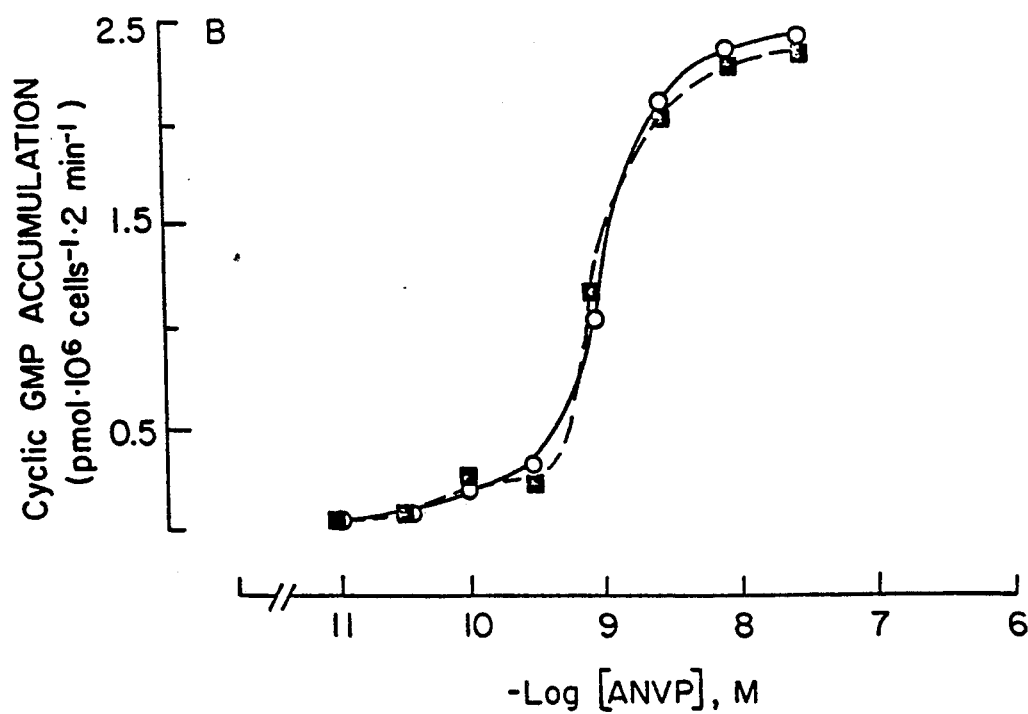
FIG._10B.

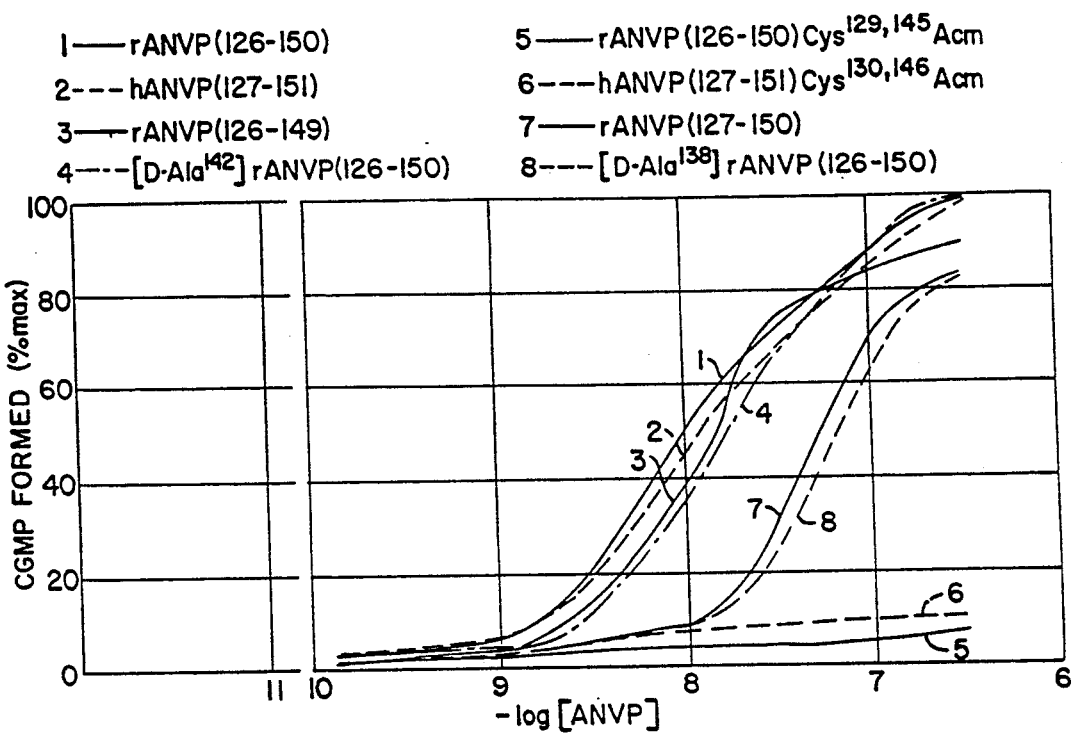
FIG._11A.
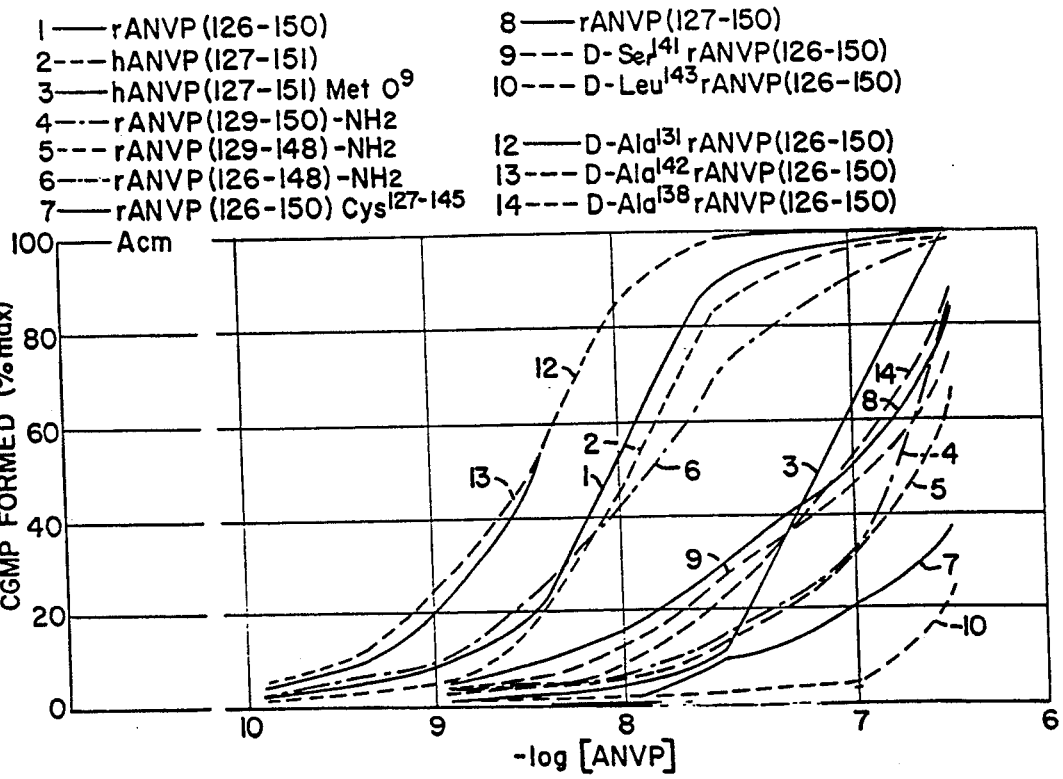
FIG._11B.

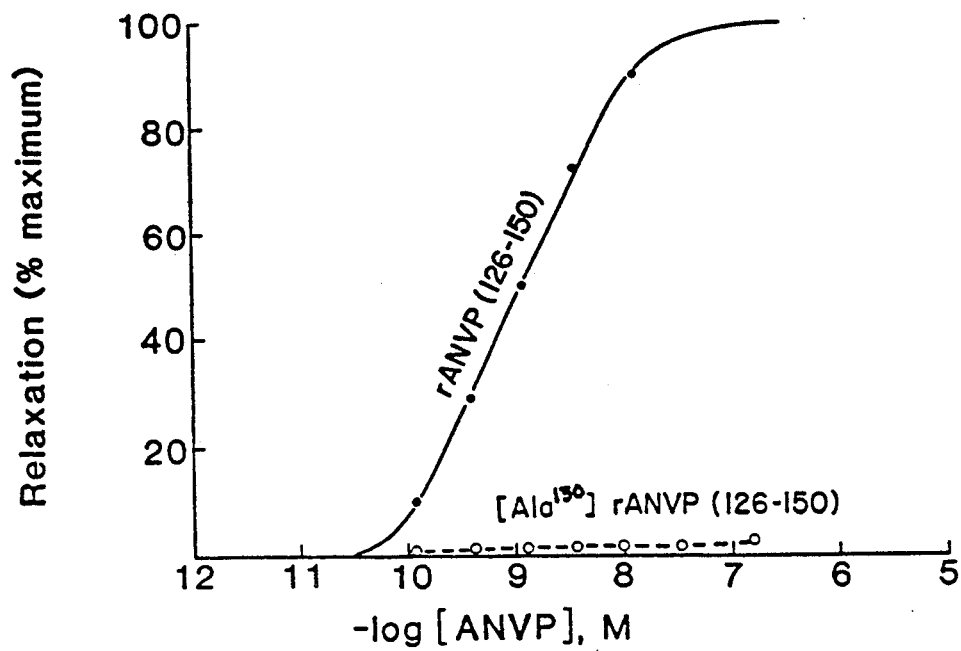
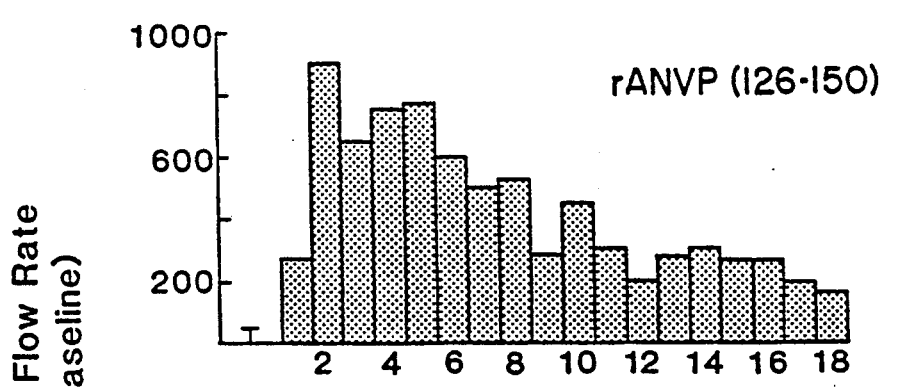
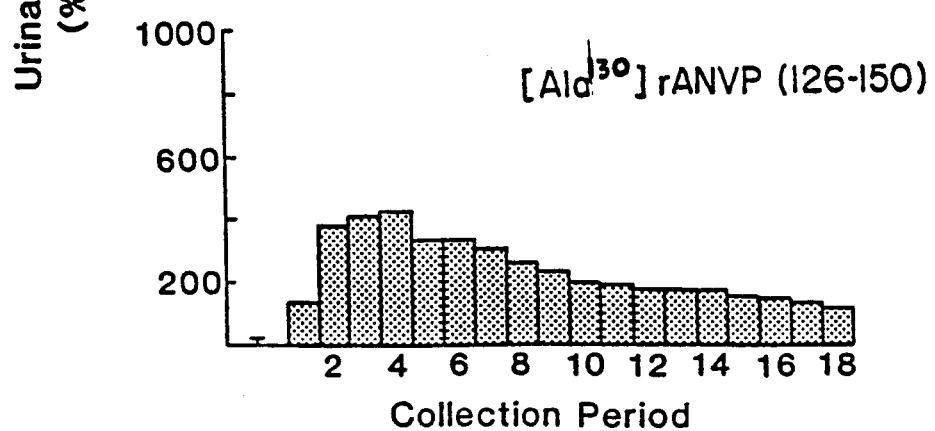

FIG._13A.
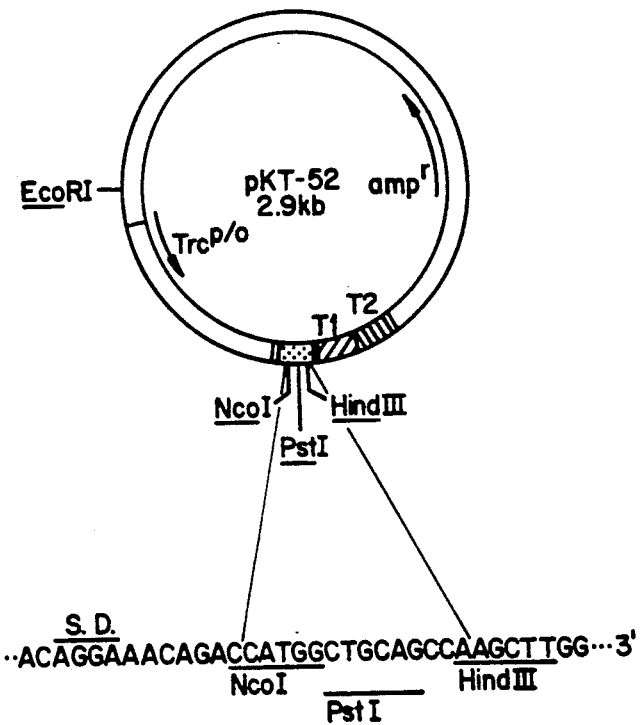
FIG._13B.
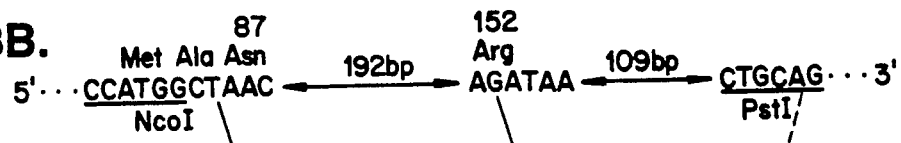
FIG._13C.
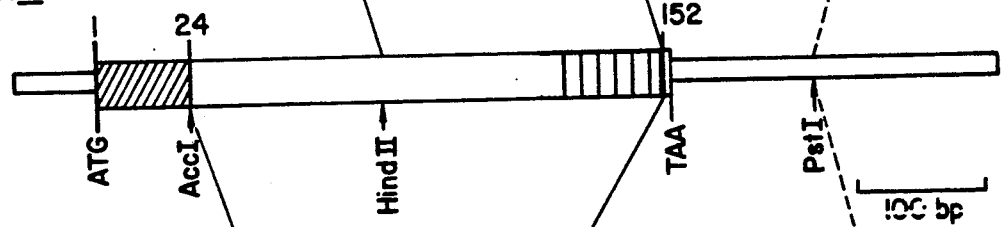
FIG._13D.

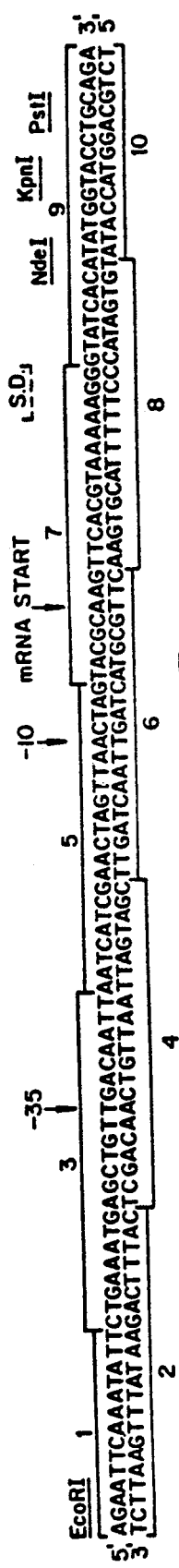
FIG._13E.
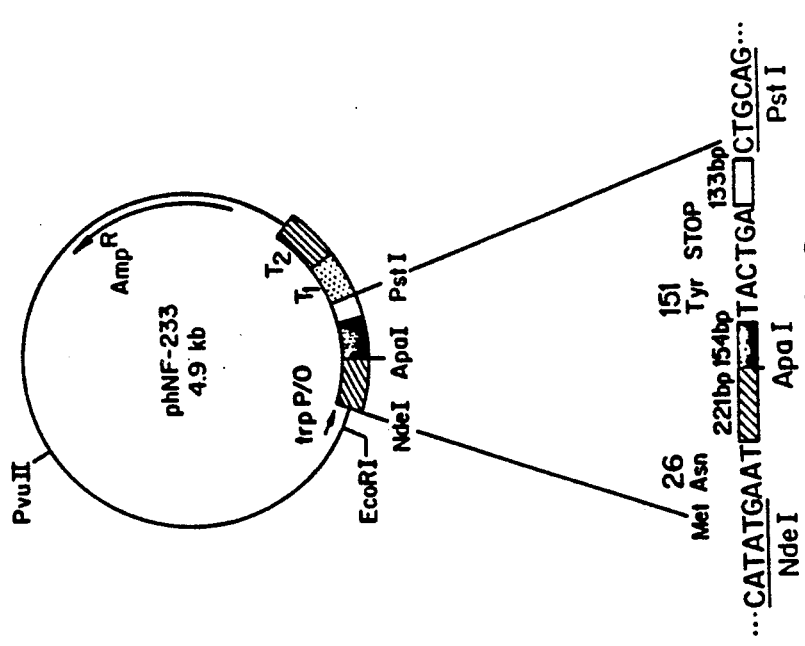
FIG._13G.
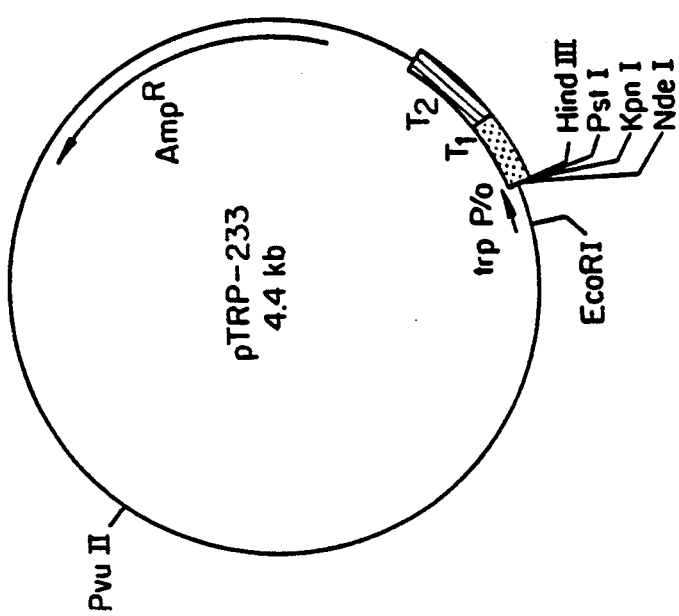
FIG._13F.

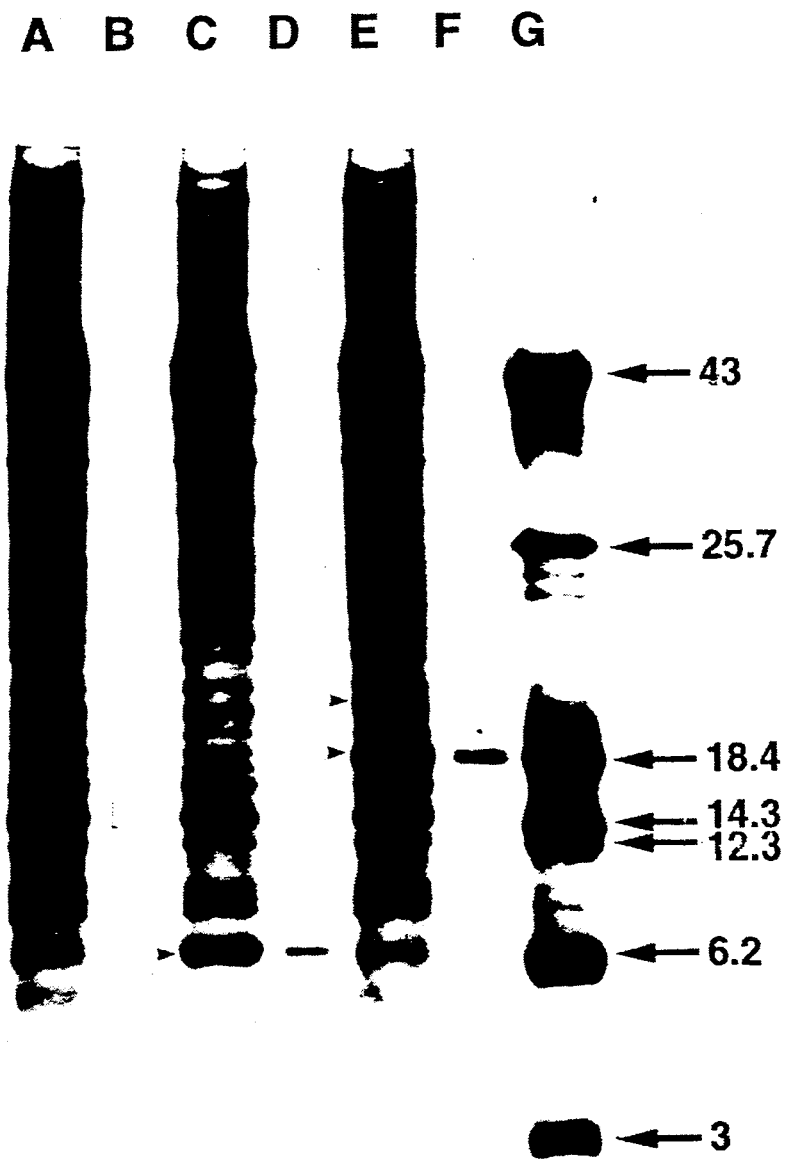
FIG. _14.

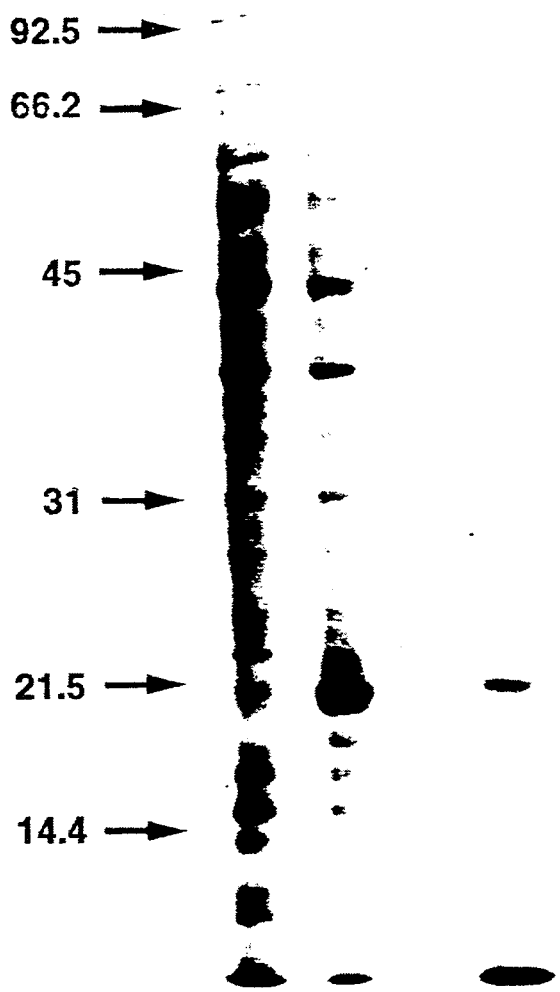
FIG. _15.

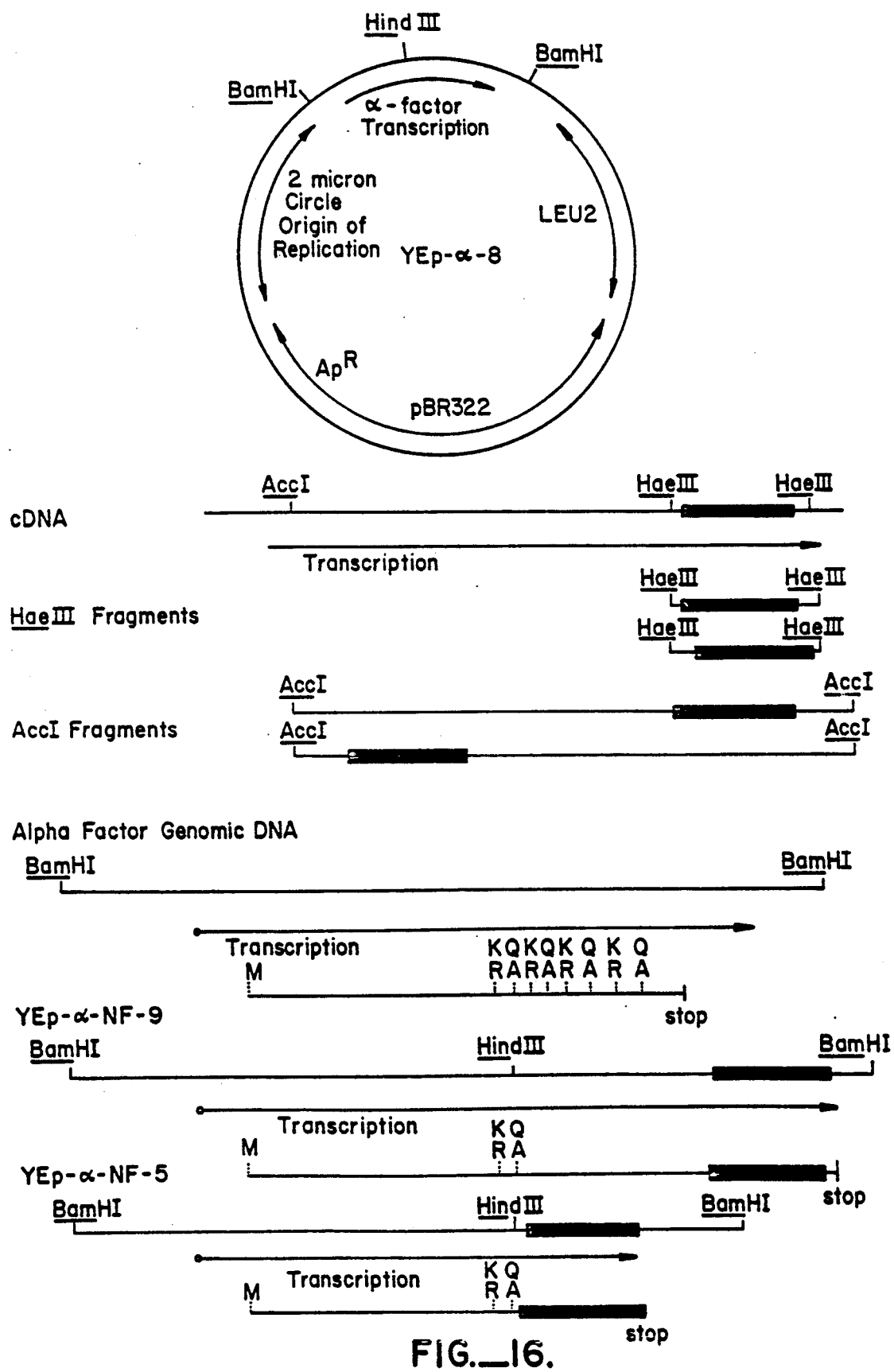
FIG._16.

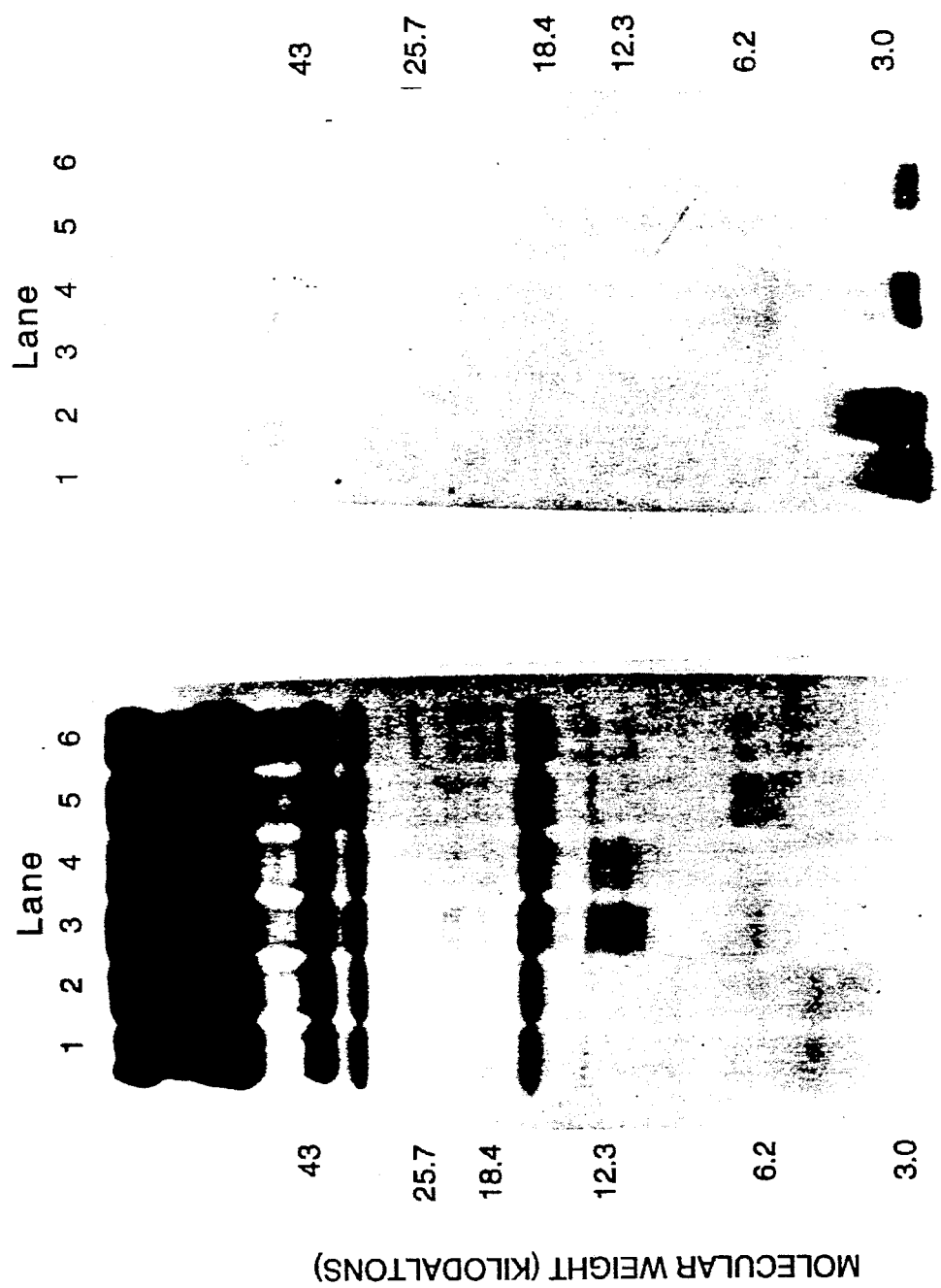
FIG._17A.
FIG._17B.

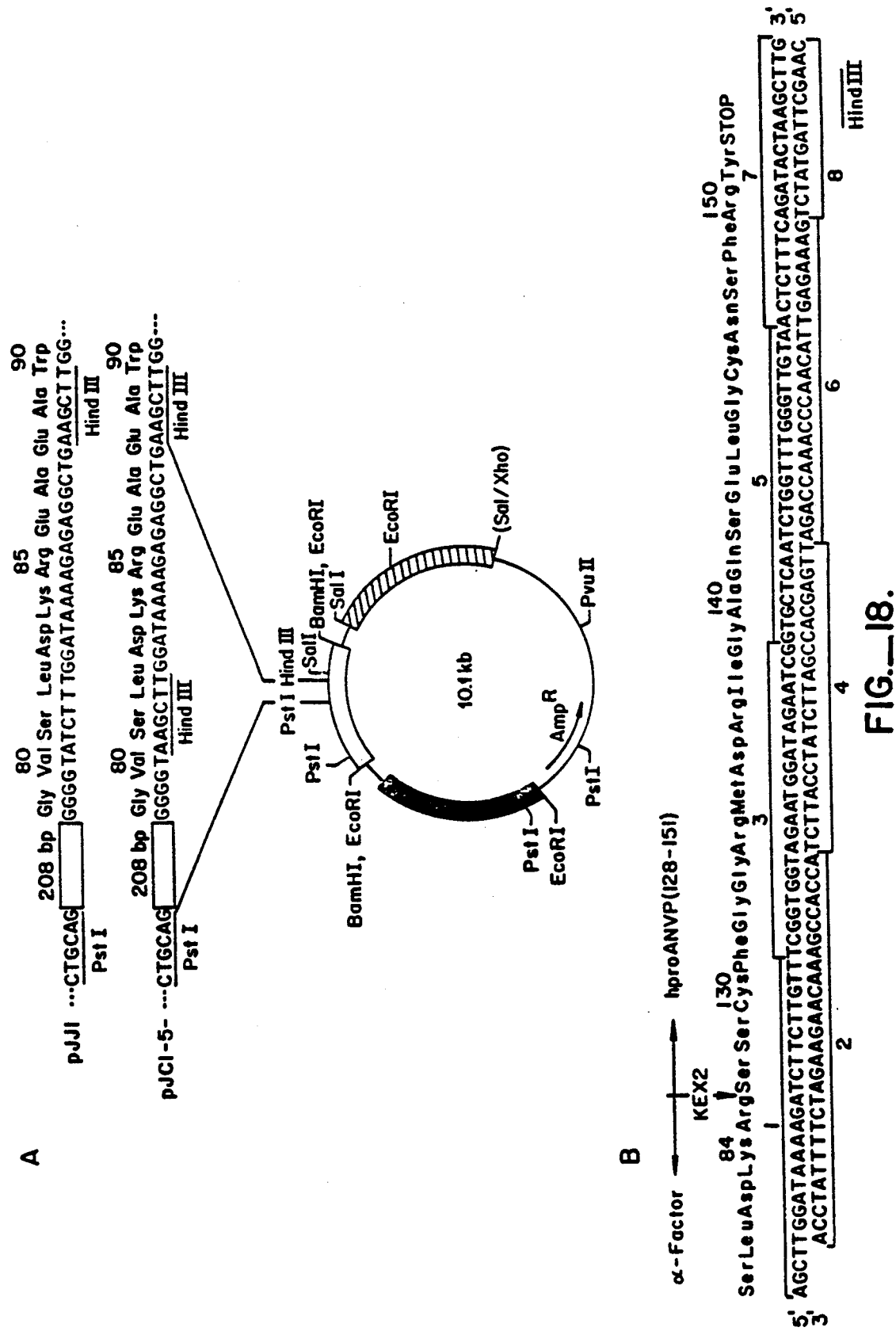
FIG._18.

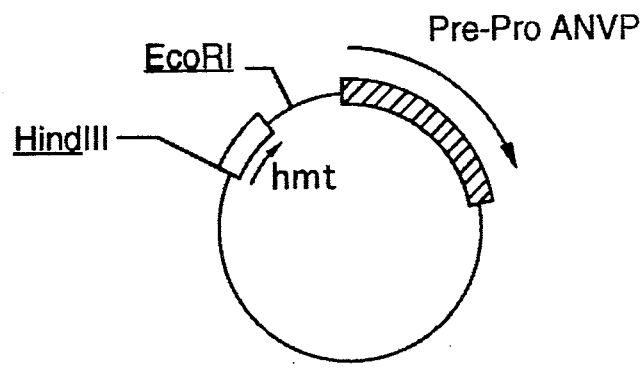
FIG._19A.
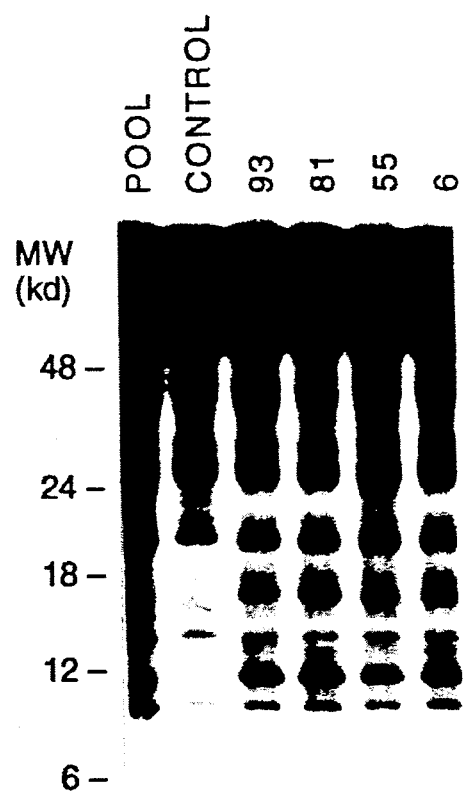
FIG._19B.

ATRIAL NATRIURETIC/VASODILATOR PEPTIDE COMPOUNDS

This application is a continuation-in-part of U.S. Ser. No. 766,030, filed May 8, 1985, now U.S. Pat. No. 4,764,504, which is a continuation-in-part of U.S. Ser. No. 602,117, filed Apr. 19, 1984, now U.S. Pat. No. 4,618,600, and also a continuation-in-part of U.S. Ser. No. 616,488, filed June 1, 1984, which is now abandoned.

DESCRIPTION

1. Technical Field

The present invention relates generally to atrial peptides and more particularly to such peptide compounds and analogs thereof which find use as diuretics, natriuretics and/or vasodilators, or as intermediates for or modulators of such useful compounds, to pharmaceutical compositions containing such useful compounds and to methods for the production and use of such compounds and compositions as therapeutics for mammalian hosts.

2. Background Art

Most multi-cellular organisms are organized into tissues and organs which perform specialized functions. Thus, a system has evolved to transport materials between them. In higher animals, including mammals, this circulatory system is closed to improve the efficiency of transport. The flow of blood fluid through this closed cardiovascular system requires that the fluid be maintained under pressure and the regulation of the systemic arterial blood pressure requires a complex interaction of numerous factors including, e.g., fluid volume and vascular elasticity and caliber.

The maintenance of normal extracellular fluid volume depends primarily on the excretion of sodium (natriuresis) and water (diuresis) by the kidneys. This renal excretion is determined by (1) the rate at which plasma is filtered at the glomerulus (glomerular filtration rate, or GFR) and (2) the degree to which sodium is actively reabsorbed along the renal tubule (with water following passively). The latter process is in part regulated by the adrenal steroid hormone aldosterone. It has been long believed that, in addition to GFR and aldosterone, there must be a "third factor" which also regulates sodium reabsorption. It is now apparent that many of the phenomena which required the postulation of a "third factor" can be explained by the effects of physical forces (e.g. blood pressure, red blood cell concentration and plasma viscosity) on sodium reabsorption. Nonetheless, the search continues for a "natriuretic hormone" which might modulate tubular reabsorption.

There are several candidates for such a hormone, among which are included the natriuretic factor(s) recently isolated from atrial muscle cells. A natriuretic effect has been demonstrated by crude extracts of rat atrial tissue but not ventricular tissue. De Bold, A. J. et al., Life Sciences, 28:89–94 (1981), Garcia, R., Experientia, 38:1071–73 (1982), Currie, M.G. et al., Science 221:71–73 (1983). Various peptides with diuretic and natriuretic properties have been isolated from atrial tissue and sequenced. Flynn, T. G. et al., Biochem. Biophys. Res. Commun. 117:859–865 (1983), Currie, M.G. et al., Science 223:67–69 (1984), Kangawa, K. et al., Biochem. Biophys. Res. Commun. 118:131–139 (1984). The existence of these atrial natriuretic factors strengthens the long-held suspicion that the heart, aside from its obvious influence on renal perfusion, may play an important role in regulating renal sodium and water excretion. Stretching of the atria is known to induce diuresis and natriuresis, and this is possibly mediated by increased release of these factors.

A number of clinically important disease states are characterized by abnormal fluid volume retention. Congestive heart failure, cirrhosis of the liver and the nephrotic syndrome each lead to excessive fluid accumulation on the venous side of the circulation, the presumed common mechanism being under-perfusion of the kidneys leading to a fall in GFR. In addition the reduced renal perfusion stimulates excessive secretion of renin, a proteolytic enzyme whose action in the circulation leads to the formation of angiotensin. Angiotensin is a powerful constrictor of arterioles (which helps to maintain arterial pressure) and also stimulates release of the sodium-retaining hormone aldosterone by the adrenal gland (which further worsens fluid retention). These mechanisms do not, however, fully account for the fluid retention of the so-called "edematous states", and additional factors are likely to be involved. One important possibility is that a relative or absolute deficiency of atrial natriuretic factor might contribute to the fluid retention.

An increase in extracellular fluid volume is also thought to contribute to the development of hypertension in many instances. Hypertension, or chronically elevated blood pressure, is one of the major causes of illness and death worldwide. It is estimated that more than 20 million Americans suffer from this disease whose complications include heart failure, heart attack, stroke and kidney failure. The major observed hemodynamic abnormality in chronic hypertension is increased resistance to the flow of blood through the arterioles. The mechanisms which lead to this increased "peripheral resistance" are, however, incompletely understood. In some cases inappropriate activity of the renin-angiotensin system or sympathetic nervous system may lead to excessive constriction of the arterioles; by "inappropriate" it is meant that the unknown signal(s) leading to this activity are not based upon a physiological need of the organism and thus lead to elevated blood pressure (whereas, in the example cited earlier, the increased renin secretion in the edematous states is a response to reduced arterial pressure and thus helps to restore or maintain normal pressure). In a substantial fraction of hypertensives however, inappropriate sodium and volume retention by the kidney is felt to either initiate or contribute to the elevated blood pressure. The responsible defect in kidney function and the mechanism whereby fluid retention leads to increased peripheral resistance are both unknown. It is certainly possible that deficiency of a natriuretic hormone could be responsible for these observations, particularly if the same substance also normally exerted a relaxant effect on arterioles.

Diuretic therapy is currently a mainstay in the treatment of hypertension, renal failure and the various edematous states (heart failure, etc.). Currently available pharmacological preparations have, however, several important limitations and undesirable effects. While their use may be directed at a specific abnormality (i.e. volume expansion), their multiple actions are undoubtedly not physiological, leading for instance to potassium depletion, increased retention of uric acid and abnormal glucose and lipid metabolism. In addition, all known diuretics profoundly stimulate the renin-angiotensinaldosterone system, which counteracts their volume-depleting and blood pressurelowering effects and leads to other unwanted effects. It would be desirable to provide a pharmacologically effective compound which can regulate blood pressure by providing a complete but controlled range of physiological responses.

However, the isolation of such compounds from atrial tissue is typically a cumbersome process and requires substantial substrate tissue to produce minute quantities of the compounds. While certain of these compounds can be produced by chemical synthesis, it was also considered desirable to apply recombinant deoxyribonucleic acid (rDNA) and related technologies to the production of larger quantities of such compounds to provide material for clinical and therapeutic applications.

Proceeding from the seminal work of Cohen & Boyer, U.S. Pat. No. 4,237,224, rDNA technology has become useful to provide novel DNA sequences and produce large amounts of heterologous proteins in transformed cell cultures. In general, the joining of DNA from different organisms relies on the excision of DNA sequences using restriction endonucleases. These enzymes are used to cut donor DNA at very specific locations, resulting in gene fragments which contain the DNA sequences of interest. These DNA fragments usually contain short single-stranded tails at each end, termed "sticky-ends". These sticky-ended fragments can then be ligated to complementary fragments in expression vehicles which have been prepared, e.g., by digestion with the same restriction endonucleases. Having created an expression vector which contains the structural gene of interest in proper orientation with the control elements, one can use this vector to transform host cells and express the desired gene product with the cellular machinery available. Once expressed, the gene product is generally recovered by lysing the cell culture, if the product is expressed intracellularly, or recovering the product from the medium if it is secreted by the host cell.

Recombinant DNA technology has been used to express entirely heterologous gene products, termed direct expression, or the gene product of interest can be expressed as a fusion protein containing some parts of the amino acid sequence of a homologous protein. This fusion protein is generally processed posttranslationally to recover the native gene product. Many of the techniques useful in this technology can be found in Maniatis, T., *et al.*, *Molecular Cloning: A Laboratory Manual*, Cold Spring Harbor Laboratory, N.Y. (1982).

However, while the general methods are easy to summarize, the construction of an expression vector containing a desired structural gene is a difficult process and the successful expression of the desired gene product in significant amounts while retaining its biological activity is not readily predictable. Frequently gene products are not biologically active when expressed in yeast, bacteria or mammalian cell systems. In these cases, post-translational processing is required to produce biological activity.

DISCLOSURE OF THE INVENTION

Compounds of the present invention useful as natriuretics, diuretics, vasodilators and/or modulators of the renin-angiotensin-aldosterone system include atrial natriuretic/vasodilator peptide (ANVP) compounds substantially free of unrelated atrial tissue or products.

Included are peptide compounds identified by the formula:

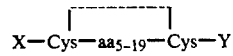

wherein each $aa_n$ is an amino acid residue of the general formula

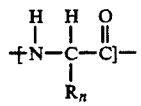

including any of the D-isomer, L-isomer and DL-isomer (racemic mixture) residues; and including compounds having bonds, preferably disulfide bonds, between the cysteine residues, as indicated and wherein $R_n$ is hydrogen or an aliphatic, aromatic or alkaryl group of from one to ten, usually one to six carbon atoms, including groups having substitutions of three or less nitrogen, oxygen or sulfur atoms as amido, thio or oxy, including hydroxy, thiol and ethers, wherein the ether is usually an alkyl ether, generally of one carbon atom, e.g. methyl;

X is hydrogen, amido, acetyl or additionally includes an oligopeptide of up to 125 amino acid residues, including N-acetyl and amido derivatives thereof; and Y is hydroxyl, amido or an oligopeptide of up to 20 amino acid residues, including C-terminal amide derivatives thereof.

Also provided are methods for producing peptide compounds of the present invention as defined by the above-disclosed formula comprising:

a) forming a peptide intermediate having at least 1 protective group or a bond attaching said intermediate to a resin support;

b) removing the protective group or the resin attachment bond from said intermediate to create a peptide compound;

c) optionally oxidizing said peptide intermediate or peptide compound to create a disulfide bridge between the cysteine residues of said intermediate or compound; and d) optionally converting the peptide compound to a physiologically acceptable salt thereof.

Pharmaceutical compositions containing these compounds, and methods for using these compounds and compositions as therapeutic agents are also provided.

BRIEF DESCRIPTION OF THE DRAWINGS

FIG. 1A provides the deoxyribonucleic acid (DNA) sequence of an embodiment of the present invention, namely a gene encoding human pre-proANVP, together with the amino acid sequence of the peptide synthesis directed by this DNA;

FIG. 1B provides the complementary DNA (cDNA) sequence of an embodiment of the present invention, namely cDNA encoding human pre-proANVP, together with the amino acid sequence of the peptide synthesis directed by this DNA;

FIG. 2 provides the DNA sequence of an embodiment of the present invention, namely DNA encoding rat pre-proANVP, together with the amino acid sequence of the peptide synthesis directed by this DNA;

FIGS. 3A–D are graphic representations of the purification of selected atrial natriuretic/vasodilator peptide (ANVP) compounds of the present invention from atrial tissue, in which:

FIG. 3A displays the results of G-50 gel filtration of crude atrial extract;

FIG. 3B displays the results of HPLC (C18 column) purification of refined extract;

FIG. 3C displays the re-chromatography of the product of FIG. 3B; and

FIG. 3D displays the results of HPLC (CN column) purification of the purified active fractions of FIG. 3C;

FIG. 4 portrays sequences of oligonucleotide probes used to identify complementary DNA (cDNA) clones containing nucleic acid compositions of the present invention;

FIG. 5 depicts the sites at which specific restriction endonucleases cleaved the DNA encoding rat pre-proANVP to provide DNA fragments for dideoxynucleotide sequence analysis;

FIG. 6, panel (a) shows the results of Northern blot analysis of atrial and ventricular mRNA in which lane 1 depicts RNA isolated from rat atrial tissue and lane 2 depicts RNA isolated from rat ventricular tissue;

FIG. 6, panels (b), (c), (d) and (e) show the results of two dimensional gel fractionation of cell-free translation products encoded by poly A+ RNA where (b) shows [$^{35}$S]-labeled proteins encoded by atrial poly A+ RNA and (c) shows [$^{35}$S]-labeled proteins encoded by ventricular poly A+ RNA. In vitro translations of poly A+ RNA specifically hybridizing to and eluting from DNA encoding rat pre-proANVP is shown, where (d) depicts poly A+ RNA derived from atrial tissue and (e) depicts poly A+ RNA derived from ventricular tissue;

FIG. 7 shows the sites at which specific restriction endonucleases cleaved human genomic DNA encoding human pre-proANVP to provide DNA fragments for dideoxynucleotide sequence analysis;

FIG. 8 presents a comparison of the vasorelaxant activity of selected purified and synthetic compounds of the present invention;

FIGS. 9A and B portray the binding of [$^{125}$I]-rANVP(126-150) to cultured bovine aortic smooth muscle cells (9A) and aortic endothelial cells (9B). The solid line (—) represents specific binding and the dashed line (---) represents non-specific binding. Analysis of the data by Scatchard plots is shown in the inset;

FIGS. 10A and B depict cyclic GMP levels in cultured bovine vascular smooth muscle (10A) and vascular endothelial cells (10B) in response to various doses of rANVP(126-150) and hANVP(127-151), respectively;

FIGS. 11A and B are dose-response curves depicting the ability of various ANVPs to increase cGMP in cultured bovine aortic smooth muscle cells (11A) and cultured bovine aortic endothelial cells (11B). Data are expressed as the percent maximal response as a function of dose;

FIG. 12 graphically portrays a comparison of the activities of selected compounds of the present invention, in which Panel A depicts a dose response relationship comparing the vasorelaxant properties of rANVP (126-130) and [Ala$^{130}$]rANVP(126-150) and Panel B portrays a comparison of the diuretic activities of the same two peptides following infusion into experimental animals. Urinary flow rates during and post infusion (periods 7-24) were compared to control (baseline) flow rates (periods 1-6) and data are expressed as the percentage of baseline control values;

FIG. 13 is a schematic representation of the bacterial expression plasmids used in the expression of rat and human pro-ANVP and derived fragments, in which FIG. 13A shows plasmid expression vector pKT-52; FIG. 13B shows a segment of DNA derived from the rat pre-proANVP cDNA, shown in FIG. 13C, encoding amino acids 87-152 cloned in plasmid pRNF-6852; FIG. 13D shows a segment of DNA derived from the rat pre-proANVP cDNA of FIG. 13C, encoding amino acids 25-152, cloned in plasmid pRNF-12852; FIG. 13E shows a synthetic DNA sequence containing the tryptophan operon promoter/operator and Shine-Delgarno sequence (SD) used to construct pTRP-233 shown in FIG. 13F; and FIG. 13G a segment of DNA derived from the human preproANVP, cDNA encoding amino acids 26-151, cloned in plasmid phNF-233;

FIG. 14 is a photographic representation of an SDS-polyacrylamide gel showing proteins labeled with L-[$^{35}$S]-cysteine in which E. coli in lane A contained the pKT52 expression vector; in lane C contained pRNF6852 (pKT52 modified to contain DNA encoding amino acids 87-152 of pre-proANVP); in lane E contained pRNF-12852 (pKT52 modified to contain DNA encoding amino acids 25-152 of pre-proANVP); in lanes B, D and F were samples of the products from lanes A, C and E, respectively, that were immunoprecipitated with a specific anti-ANVP antiserum; and in lane G were protein molecular weight standards, with their corresponding molecular sizes labeled. Arrows indicate unique peptide compounds derived from pRNF-6852 and pRNF-12852;

FIG. 15 is a photographic representation of an SDS polyacrylamide gel showing proteins labeled with [$^{35}$S]-cysteine in which E. coli in lane A contained the pTRP-233 expression vector, lane B contained phNF-233 (pTRP-233 modified to contain DNA encoding human pre-proANVP(26-151)) expression product; lanes C and D contained the products from lanes A and B, respectively, that were immunoprecipitated with specific anti-ANVP antiserum. Sizes of molecular weight standards are shown adjacent to lane A;

FIG. 16 depicts a construction for expressing rat pre-proANVP and related peptide compound fragments in Saccharomyces cerevisiae using a specific vector and the yeast α-factor secretion signal;

FIG. 17 is a photographic representation of an SDS polyacrylamide gel showing S. cerevisiae-secreted proteins labeled with [$^{35}$S]-methionine (A) or [$^{35}$S]-cysteine and [$^{35}$S]-methionine (B). In panel A, S. cerevisiae in lanes 1 and 2 contained the YEp-α-8 shuttle vector, in lanes 3 and 4 contained YEp-α-NF-9, and in lanes 5 and 6 contained YEp-α-NF-12. In panel B, the secreted proteins were acetone and methanol extracted. Lanes 1 and 2 represent secreted proteins from S. cerevisiae containing YEp-α-NF-7 and YEp-α-NF-5, respectively; lanes 3 and 4 represent the proteins from these preparations after immunoprecipitation with specific anti-ANVP IgG; lanes 5 and 6 contained secreted proteins from S. cerevisiae containing YEp-α-NF-12 and YEp-α-NF-9, respectively, and show the proteins specifically immunoprecipitated by anti-ANVP IgG;

FIG. 18 depicts a schematic diagram of the yeast expression plasmid and synthetic gene sequence encoding hANVP(128-151). The construction details are presented in Section IV. Panel A depicts sequences of the relevant regions within plasmids JJ-1 and JC1-5.

Representations are: ⊢——⊣ pBR322 sequences; ▬▬ DNA fragment containing the B form of 2μ; ⊨⊨ DNA fragment encoding the α-factor precursor/peptide; and ▭▭ DNA fragment containing the LEU2 gene. Panel B presents a synthetic DNA gene sequence encoding hANVP(128-151), wherein the component oligodeoxynucleotides are numbered 1-8. Amino acid numbering above the nucleotide sequence for α-factor corresponds to the gene sequence described by Kurjan J. and Herskowitz, supra.

FIG. 19A depicts an expression vector construction for expressing rat and human pre-proANVP in Chinese hamster ovary cells; and FIG. 19B is a photographic representation of an SDS-polyacrylamide gel of [$^{35}$S]-methionine labeled protein from Chinese hamster ovary cell media, in which lane 1 shows [$^{35}$S]-methionine labeled proteins from a CHO cell pool containing sequences directing the synthesis of prohANVP(26-151), lane 2 shows [$^{35}$S]-methionine labeled proteins from control CHO cells, lanes 3-6 show [$^{35}$S]-methionine labeled proteins from CHO cells containing sequences directing the synthesis of prohANVP(26-151) where lanes 3-6 represent CHO-8/2-93, CHO-8/2-81, CHO-8/2-55 and CHO-8/2-6 respectively.

BEST MODE FOR PRACTICING THE INVENTION

In accordance with the present invention novel atrial natriuretic/vasodilator peptide (ANVP) compounds are provided for the regulation of fluid volume and blood pressure in host organisms, in which one aspect of the invention provides ANVP compounds comprising the formula:

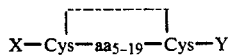

(I)

wherein each $aa_n$ is an amino acid residue of the general formula

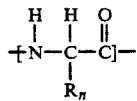

including any of the D-isomer, L-isomer and DL-isomer (racemic mixture) residues; and including compounds having bonds, preferably disulfide bonds, between the cysteine residues, as indicated; and
wherein
  $R_n$ is hydrogen or an aliphatic, aromatic or alkaryl group of from one to ten, usually one to six carbon atoms, including groups having substitutions of three or less nitrogen, oxygen or sulfur atoms as amido, thio or oxy, including hydroxy, thiol and ethers, wherein the ether is usually an alkyl ether, generally of one carbon atom, e.g., methyl;
  X is hydrogen, amido, acetyl or additionally includes an oligopeptide of up to 125 amino acid residues, including N-acetyl and amido derivatives thereof;
  Y is hydroxyl, amino or an oligopeptide of up to 20 amino acid residues, including C-terminal amide derivatives thereof; and including the physiologically acceptable salts, amides and esters thereof.

Certain presently preferred embodiments of the present invention are provided in accordance with formula I wherein
  X is selected from the group consisting of H-Arg-Ser-Ser-, H-Arg-Ser-[D-Ser]-, H-Arg-[D-Ser]-Ser-, H-[D-Arg]-Ser-Ser-, H-Arg- and H-[D-Arg]-; and
  Y is selected from the group consisting of Asn-Ser-Phe-Arg-Tyr-OH, Asn-Ser-Phe-Arg-Tyr-NH2, Asn-[D-Ser]-Phe-Arg-Tyr-OH, Asn-[D-Ser]-Phe-Arg-Tyr-NH2, Asn-Ser-Phe-Arg-OH, Asn-Ser-Phe-Arg-NH2, Asn-[D-Ser]-Phe-Arg-OH, Asn-[D-Ser]-Phe-Arg-NH2, Asn-Ser-Phe-OH, Asn-Ser-Phe-NH2, -OH, and -NH2;

With the proviso that when aa$_{5-19}$ is Phe-Gly-Gly-Arg-Met(Ile)-Asp-Arg-Ile-Gly-Ala-Gln-Ser-Gly-Leu-Gly-and:
  when X is an oligopeptide identified as H-Arg-Ser-Ser-, then either
  Y is not Asn-Ser-Phe-Arg-Tyr-OH or Asn-SerPhe-Arg-OH; or
  when Y is Asn-Ser-Phe-Arg-Tyr-OH or Asn-SerPhe-Arg-OH, then at least one amino acid residue in the compound is a D-isomer.

Also included in the present invention are ANVP compounds having the general formula:

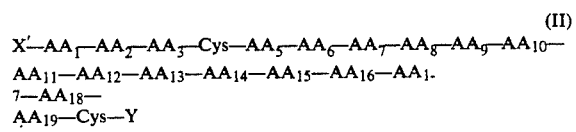

(II)

wherein
  the cysteine residues disclosed above are independently optionally [D-Cys] and also optionally bound by a disulfide bond; and
  $AA_1$ amino acid residue, preferably Arg or [D-Arg];
  $AA_2$ and $AA_3$ are each independently a bond or the same or different neutral polar amino acid residues, preferably where $AA_2$ is Ser, [D-Ser] or des $AA_2$, $AA_3$ is Ser, [D-Ser] or des $AA_3$;
  $AA_5$, $AA_9$, $AA_{12}$, $AA_{14}$ and $AA_{18}$ are each independently the same or different neutral nonpolar amino acid residues, preferably where $AA_5$ is Phe or [D-Phe], $AA_9$ is Ile, [D-Ile], Met, [D-Met], Val or [D-Val], $AA_{12}$ is Ile, [D-Ile], Val or [D-Val], $AA_{14}$ is Ala or [D-Ala] and $AA_{18}$ is Leu or [D-Leu];
  $AA_6$, $AA_7$, $AA_{13}$, $AA_{15}$, $AA_{16}$, $AA_{17}$ and $AA_{19}$ are each independently the same or different neutral amino acid residues, preferably where $AA_6$ is Gly, Ala or [D-Ala], $AA_7$ is Gly, Ala, [D-Ala]or Pro, $AA_{13}$ is Gly, Ala or [D-Ala], $AA_{15}$ is Gln or [D-Gln], $AA_{16}$ is Ser or [D-Ser], $AA_{17}$ is Gly, Ala or [D-Ala] and $AA_{19}$ is Gly, Ala or [D-Ala];
  $AA_8$ and $AA_{11}$ are each independently the same or different basic polar or neutral nonpolar amino acid residues, preferably Arg, [D-Arg], Lys, [D-Lys] or Nle;
  $AA_{10}$ is any acidic polar amino acid residue, preferably Asp or Glu;
  X' is hydrogen, amido, acetyl or additionally includes an oligopeptide of up to 125 amino acid residues, including N-acetyl and amido derivatives thereof; and
  Y is as previously defined.

Generally preferred embodiments of the present invention include compounds identified by the formula:

X'—Arg([D—Arg])—Ser([D—Ser])(desSer)
—Ser([D—Ser])([desSer]—Cys([D—Cys])
—Phe([D—Phe])(Ala)(Leu)—Gly(Ala)([D—Ala])
—Gly(Ala)([D—Ala])(Pro)—Arg(Lys)(Nle)
—Met([D—Met])(Ile)([D—Ile])([D—Val])(Phe)
—Asp([D—Asp])(Asn)(Glu)(Ser)(Val)
—Arg([D—Arg])(Lys)(Nle)—Ile([D—Ile])([D—Val])
—Gly([D—Ala])—Ala([D—Ala])—Gln([D—Gln])
—Ser([D—Ser])—Gly([D—Ala])—Leu([D—Leu)]
—Gly([D—Ala])—Cys([D—Cys])—Y where X' and Y are as defined previously, the cysteine residues are optionally but desirably bound by a disulfide bond and amino acid residues or des residues in parenthesis are alternatives to the non-parenthetical residue immediately preceeding.

Certain presently preferred embodiments included in the above formulae include:

X—Cys—Phe(Ala)—Gly(Ala)—Gly—Arg—Ile(Val)—Asp—
Arg—Ile—Gly(Ala)—Ala—Gln—Ser—Gly(Ala)—Leu—
Gly—Cys—Y
or
X—Cys—Phe(Ala)—Gly(Ala)—Gly—Arg—Met(Val)—Asp—Arg—
Ile—Gly(Ala)—Ala—Gln—Ser—Gly(Ala)—Leu—Gly—Cys—Y wherein amino acid residues in parenthesis are alternatives to the residue immediately preceeding, the cysteine residues are bound by a disulfide bond and X is selected from the group consisting of H-Arg-Ser-Ser, H-[D-Arg]-Ser-Ser, H-Arg-[D-Ser]-Ser, H-Arg-Ser-[D-Ser], H-Arg, H-[D-Arg], COOH— or H—; and Y is selected from the group consisting of Y', Asn-Ser-Phe-Y', Asn-Ser-Phe- Arg-Y' and Asn-Ser-Phe-Arg-Tyr-Y', and where Y' is OH, NH$_2$ or an oligopeptide;

For example, without showing the optional disulfide bond, such compounds include:

H-Arg-Ser-Ser-Cys-Phe-Gly-Gly-Arg-Ile-Asp-Arg-IleGly-Ala-Gln-Ser-Gly-Leu-Gly-Cys-Asn-Ser-Phe-ArgTyr-OH;

H-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-OH;

H-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH;

H-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-OH;

H-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-NH$_2$;

H-Arg-Ser-Ser-Cys-Phe-Gly-Gly-Arg-Met-Asp-Arg-Ile-Gly-Ala-Gln-Ser-Gly-Leu-Gly-Cys-NH$_2$;

H-Arg-Ser-Ser-Cys-Phe-Gly-Gly-Arg-Ile-Asp-Arg-Ile-Gly-Ala-Gln-Ser-[D-Ala]-Leu-Gly-Cys-Asn-Ser-Phe-Arg-Tyr-OH;

H-Arg-Ser-Ser-Cys-Phe-Gly-Gly-Arg-Ile-Asp-Arg-Ile-Gly-Ala-Gln-[D-Ser]-Gly-Leu-Gly-Cys-Asn-Ser-Phe-Arg-Tyr-OH;

H-Arg-Ser-Ser-Cys-Phe-Gly-Gly-Arg-Ile-Asp-Arg-Ile-Gly-Ala-Gln-Ser-Gly-[D-Leu]-Gly-Cys-Asn-Ser-Phe-Arg-Tyr-OH;

H-Arg-Ser-Ser-Cys-Phe-Gly-Gly-Arg-Ile-Asp-Arg-Ile-Gly-Ala-[D-Gln]-Ser-Gly-Leu-Gly-Cys-Asn-Ser-Phe-Arg-Tyr-OH;

H-Arg-Ser-Ser-Cys-Phe-Gly-Gly-Arg-Ile-Asp-Arg-Ile-[D-Ala]-Ala-Gln-Ser-Gly-Leu-Gly-Cys-Asn-Ser-Phe-Arg-Tyr-OH;

H-Arg-Ser-Ser-Cys-Phe-Gly-Gly-Arg-Ile-Asp-Arg-Ile-Gly-[D-Ala]-Gln-Ser-Gly-Leu-Gly-Cys-Asn-Ser-Phe-Arg-Tyr-OH;

H-Arg-Ser-Ser-Cys-Phe-[D-Ala]-Gly-Arg-Ile-Asp-Arg-Ile Gly-Ala-Gln-Ser-Gly-Leu-Gly-Cys-Asn-Ser-Phe-Arg-Tyr-OH;

H-Arg-Ser-Ser-Cys-Phe-Gly-Gly-[D-Arg]-Ile-Asp-Arg-Ile-Gly-Ala-Gln-Ser-Gly-Leu-Gly-Cys-Asn-Ser-Phe-Arg-Tyr-OH;

H-Arg-Ser-Ser-Cys-Phe-Gly-Gly-Arg-[D-Val]-Asp-Arg-Ile-Gly-Ala-Gln-Ser-Gly-Leu-Gly-Cys-Asn-Ser-Phe-Arg-Tyr-OH;

H-Arg-Ser-Ser-Cys-[D-Phe]-Gly-Gly-Arg-Ile-Asp-Arg-Ile-Gly-Ala-Gln-Ser-Gly-Leu-Gly-Cys-Asn-Ser-Phe-Arg-Tyr-OH;

H-Arg-Ser-Ser-[D-Cys]-Phe-Gly-Gly-Arg-Ile-Asp-Arg-Ile-Gly-Ala-Gln-Ser-Gly-Leu-Gly-Cys-Asn-Ser-Phe-Arg-Tyr-OH;

H-Arg-Ser-Ser-Cys-Phe-Gly-[D-Ala]-Arg-Ile-Asp-Arg-Ile-Gly-Ala-Gln-Ser-Gly-Leu-Gly-Cys-Asn-Ser-Phe-Arg-Tyr-OH;

H-Arg-Ser-Ser-Cys-Phe-Gly-Gly-Arg-[D-Met]-Asp-Arg-Ile-Gly-Ala-Gln-Ser-Gly-Leu-Gly-Cys-Asn-Ser-Phe-Arg-Tyr-OH;

H-Arg-Ser-Ser-Cys-Phe-Gly-Gly-Arg-Ile-Asp-[D-Arg]-Ile-Gly-Ala-Gln-Ser-Gly-Leu-Gly-Cys-Asn-Ser-Phe-Arg-Tyr-OH;

H-Arg-Ser-Ser-Cys-Phe-Gly-Gly-Arg-Ile-Asp-Arg-[D-Val]-Gly-Ala-Gln-Ser-Gly-Leu-Gly-Cys-Asn-Ser-Phe-Arg-Tyr-OH;

H-Arg-Cys-Phe-Gly-Gly-Arg-Ile-Asp-Arg-Ile-Gly-Ala-Gln-Ser-Gly-Leu-Gly-Cys-Asn-Ser-Phe-Arg-Tyr-OH;

H-Arg-Cys-Phe-Gly-Gly-Arg-Ile-Asp-Arg-Ile-Gly-Ala-Gln-Ser-Gly-Leu-Gly-Cys-Asn-Ser-Phe-Arg-OH;

H-Arg-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH;

H-Arg-Cys-Phe-Gly-Gly-Arg-Met-Asp-Arg-Ile-Gly-Ala-Gln-Ser-Gly-Leu-Gly-Cys-Asn-Ser-Phe-Arg-OH;

H-Arg-Cys-Phe-Gly-Gly-Arg-Ile-Asp-Arg-Ile-Gly-Ala-Gln-Ser-Gly-Leu-Gly-Cys-Asn-Ser-Phe-NH$_2$;

H-Arg-Cys-Phe-Gly-Gly-Arg-Met-Asp-Arg-Ile-Gly-Ala-Gln-Ser-Gly-Leu-Gly-Cys-NH$_2$;

H-Arg-Cys-Phe-Gly-Gly-Arg-Ile-Asp-Arg-Ile-Gly-Ala-Gln-Ser-[D-Ala]-Leu-Gly-Cys-Asn-Ser-Phe-Arg-Tyr-OH;

H-Arg-Cys-Phe-Gly-Gly-Arg-Ile-Asp-Arg-Ile-Gly-Ala-Gln-[D-Ser]-Gly-Leu-Gly-Cys-Asn-Ser-Phe-Arg-Tyr-OH;

H-Arg-Cys-Phe-Gly-Gly-Arg-Ile-Asp-Arg-Ile-Gly-Ala-Gln-Ser-Gly-[D-Leu]-Gly-Cys-Asn-Ser-Phe-Arg-Tyr-OH;

H-Arg-Cys-Phe-Gly-Gly-Arg-Ile-Asp-Arg-Ile-Gly-Ala-[D-Gln]-Ser-Gly-Leu-Gly-Cys-Asn-Ser-Phe-Arg-Tyr-OH;

H-Arg-Cys-Phe-Gly-Gly-Arg-Ile-Asp-Arg-Ile-[D-Ala]-Ala-Gln-Ser-Gly-Leu-Gly-Cys-Asn-Ser-Phe-Arg-Tyr-OH;

H-Arg-Cys-Phe-Gly-Gly-Arg-Ile-Asp-Arg-Ile-Gly-[D-Ala]-Gln Ser-Gly-Leu-Gly-Cys-Asn-Ser-Phe-Arg-Tyr-OH;

H-Arg-Cys-Phe-[D-Ala]-Gly-Arg-Ile-Asp-Arg-Ile-
Gly-Ala-Gln-Ser-Gly-Leu-Gly-Cys-Asn-Ser-Phe-
Arg-Tyr-OH;

H-Arg-Cys-Phe-Gly-Gly-[D-Arg]-Ile-Asp-Arg-Ile-
Gly-Ala-Gln-Ser-Gly-Leu-Gly-Cys-Asn-Ser-Phe-
Arg-Tyr-OH;

H-Arg-Cys-Phe-Gly-Gly-Arg-[D-Val]-Asp-Arg-Ile-
Gly-Ala-Gln-Ser-Gly-Leu-Gly-Cys-Asn-Ser-Phe-
Arg-Tyr-OH;

H-Arg-Cys-[D-Phe]-Gly-Gly-Arg-Ile-Asp-Arg-Ile-
Gly-Ala-Gln-Ser-Gly-Leu-Gly-Cys-Asn-Ser-Phe-
Arg-Tyr-OH;

H-Arg-[D-Cys]-Phe-Gly-Gly-Arg-Ile-Asp-Arg-Ile-
Gly-Ala-Gln-Ser-Gly-Leu-Gly-Cys-Asn-Ser-Phe-
Arg-Tyr-OH;

H-Arg-Cys-Phe-Gly-[D-Ala]-Arg-Ile-Asp-Arg-Ile-
Gly-Ala-Gln-Ser-Gly-Leu-Gly-Cys-Asn-Ser-Phe-
Arg-Tyr-OH;

H-Arg-Cys-Phe-Gly-Gly-Arg-[D-Met]-Asp-Arg-Ile-
Gly-Ala-Gln-Ser-Gly-Leu-Gly-Cys-Asn-Ser-Phe-
Arg-Tyr-OH;

H-Arg-Cys-Phe-Gly-Gly-Arg-Ile-Asp-[D-Arg]-Ile-
Gly-Ala-Gln-Ser-Gly-Leu-Gly-Cys-Asn-Ser-Phe-
Arg-Tyr-OH; and H-Arg-Cys-Phe-Gly-Gly-Arg-Ile-Asp-Arg-[D-Val]-
Gly-Ala-Gln-Ser-Gly-Leu-Gly-Cys-Asn-Ser-Phe-
Arg-Tyr-OH.

The nomenclature used to describe ANVP compounds of the present invention follows the conventional practice wherein the amino group is presented to the left and the carboxy group to the right of each amino acid residue. In the formulae representing embodiments of the present invention, the Amino- and Carboxyterminal groups, when not specifically shown, will be understood to be in the form they would assume at physiologic pH values, unless otherwise specified.

In the amino acid sequence formulae each residue is specified by the conventional practice of using three letters from the trivial name of the amino acid and wherein the L form of any amino acid having an optical isomer is intended unless otherwise expressly indicated, for example by the symbol "[D-aa$_n$]".

Neutral nonpolar amino acid residues are taken to mean those residues with hydrophobic R groups at physiologic pH values, generally aliphatic or aromatic hydrocarbons of from zero to ten, usually one to six carbon atoms, which may be substituted with two or less nitrogen, oxygen or sulfur atoms, including such amino acids as Alanine (Ala), Valine (Val), Leucine (Leu), Isoleucine (Ile), Norleucine (Nle), Proline (Pro), Methionine (Met), Phenylalanine (Phe) and Tryptophan (Trp).

Neutral polar amino acid residues are taken to mean those residues with hydrophilic, uncharged R groups at physiologic pH values, including such amino acids as Glycine (Gly), Serine (Ser), Threonine (Thr), Cysteine (Cys), Tyrosine (Tyr), Asparagine (Asn) and Glutamine (Gln).

Acidic polar amino acid residues are taken to mean those residues with hydrophilic, negatively charged R groups at physiologic pH values, includinq such amino acids as Aspartic acid (Asp) and Glutamic acid (Glu).

Basic polar amino acid residues are taken to mean those residues with hydrophilic, positively charged R groups at physiologic pH values, including such amino acids as Lysine (Lys), Arginine (Arg) and Histidine (His)

Compounds within the scope of the present invention can also be obtained by modifying the above recited formulae in numerous ways while preserving the activity of the ANVP compounds thus obtained. For example, while the amino acids of these compounds are normally in the natural L form, one or more, usually two or less and preferably one amino acid may be replaced with the optical isomer D form, or a DL-racemic mixture, as demonstrated in certain of the illustrative examples included in the present application.

Amino acid residues contained within the compounds, and particularly at the Carboxy- or Aminoterminus, can also be modified by amidation, acetylation or substituted with other chemical groups which can, for example, change the solubility of the compounds without effecting their activity. In particular, it has been discovered that amide ANVP analog compounds are particularly potent and therefore preferred embodiments of the present invention. For example, the Carboxy-terminal residue will have a carbonyl carbon which has been substituted with an amino group to form a Carboxy-terminal amido group. In general, the nitrogen of the amido group, covalently bound to the carbonyl carbon, will have two substituent groups, each of which can be hydrogen, alkyl, a benzylic group (substituted or unsubstituted), and any one of which can be a nitrogen containing moiety such as hydrazide and the other can be hydrogen, or either group can be a basic or neutral dipeptide and the other can be hydrogen or an alkyl group. Representative among such amido groups are: $-NH_2$, $-NHCH_3$, $-N(CH_3)_2$, among others.

In forming amidated analogs of the present invention, the analog compound can be synthesized directly, for example using BOC-AA-pMBHA- Resin or Boc-AA-BHA-Resin, wherein AA is the selected Carboxy-terminal amino acid of the desired analog compound as described in further detail below. Alternatively, the analog compounds of the present invention can be chemically amidated subsequent to peptide synthesis using means well known to the art, or enzymatically amidated.

In addition, one or more amino acid residues can be replaced by functionally equivalent residues; for example basic polar amino acids can be replaced with other basic polar amino acids and acidic polar amino acids can be replaced with other acidic polar amino acids. However, the replacement of certain nonpolar hydrophobic amino acids, particularly cysteine, is considered less desirable due to the likelihood of interfering with the cystine disulfide bridge.

The ANVP compounds of the present invention can also be modified by extending, decreasing or substituting in the compounds' amino acid sequence, e.g., by the addition or deletion of amino acids or oligopeptides on either the N-terminal or C-terminal end, or both, of the sequences disclosed above. Particularly, Y' can be amide or an amino acid or oligopeptide of not more than about 20, more usually 8, and desirably 5 or less amino acids and X' can be N-acetyl or an amino acid or oligopeptide of not more than about 125, usually less than 10 and desirably about 3 amino acids, provided the modifications do not adversely effect all of the natriuretic, diuretic and/or vasorelaxant activities of the subject compounds.

Furthermore, compounds of the present invention can be mixed with, bonded to or conjugated with compounds having the same or a complementary range of biologic activities to obtain the benefits of the present invention.

Certain ANVP compounds of the present invention have been isolated from atrial tissue substantially free of unrelated atrial tissue or products. Generally, acetic acid extracts of atrial tissue are subjected to gel filtration, and reversed phase high performance liquid chromatography (using $C_{18}$ and CN columns), while assaying for the natriuretic and vasorelaxant activity of the fractions.

Compounds within the scope of the present invention can be isolated and purified from biological tissue sources, notably mammalian atrial tissue sources, or can be synthesized chemically by means well-known in the art such as, e.g., solid phase synthesis. The synthesis is commenced from the C-terminal end of the peptide using an alpha-amino protected amino acid. t-Butyloxycarbonyl (Boc) protective groups can be used for all amino groups even though other protective groups are suitable. For example, Boc-Arg-OH or Boc-Tyr-OH (i.e., selected C-terminal amino acids) can be esterified to chloromethylated polystyrene resin supports The polystyrene resin support is preferably a copolymer of styrene with about 0.5 to 2% divinyl benzene as a cross-linking agent which causes the polystyrene polymer to be completely insoluble in certain organic solvents. See Stewart et al., Solid-Phase Peptide Synthesis, W. H. Freeman Co., San Francisco (1969) and Merrifield, J. Am. Chem. Soc. 85:2149-2154 (1963).

Conveniently, ANVP compounds may be synthesized using manual techniques or automatically employing, for example, an Applied BioSystems 430A Peptide Synthesizer (Foster City, California) or a Biosearch SAM II automatic peptide synthesizer (Biosearch, Inc. San Rafael, Calif.) following the procedures provided in the instruction manual supplied by the manufacturer.

Alternatively, compounds of the present invention can be produced by expression of recombinant DNA constructs. Such production can be desirable to provide large quantities or alternative embodiments of such compounds.

A further aspect of the invention provides nucleic acid sequences capable of directing the synthesis of ANVPs, proANVPs (the precursor forms of the mature ANVP expression product compounds) and pre-proANVPs (proANVPs with intact signal peptides), and fragments derived therefrom, such nucleic acid sequences comprising the DNA sequences of FIGS. 1A, 1B and 2, including oligonucleotide sequences contained therein, and allowing for the replacement of codons with other codons capable of directing the synthesis of the same or functionally equivalent amino acid sequences, such equivalent amino acids including the alternative residues disclosed in the examples provided.

More particularly, modifications in the amino acid sequence of the various forms of pre-proANVP, proANVP and ANVP compounds can be effected by various changes in the nucleotide sequence of the cloned structural gene used to direct the synthesis of the compounds. Included within such modification of the DNA sequence are the replacement of various codons with other codons which, due to the degeneracy of the genetic code, direct the synthesis of the same amino acid.

In addition, by codon substitution, one or more amino acid residues can be replaced by functionally equivalent residues, as disclosed above.

Compounds of the present invention are shown to have natriuretic and diuretic activity in the intact mammal and in the kidney isolated from a mammal. Furthermore, compounds of the present invention including synthetic compounds, possess vasorelaxant activity, and inhibit the release of aldosterone, which has been shown to be enhanced by oxidation and diminished by reduction, indicating that the presence of a disulfide bridge between the cysteine residues contained in the general formulae disclosed herein is desirable for a substantial amount of the biological activity described above.

Compounds of the present invention which are shown to have the above recited physiological effects can find use in numerous therapeutic applications, such as, e.g., inducing natriuresis, diuresis, and/or vasodilatation. Thus these compounds can find use as therapeutic agents in the treatment of various edematous states such as, for example, congestive heart failure, nephrotic syndrome and hepatic cirrhosis, in addition to hypertension and renal failure due to ineffective renal perfusion or reduced glomerular filtration rate.

These compounds can be administered to mammals for veterinary use such as with domestic animals, and clinical use in humans in a manner similar to other therapeutic agents, that is, as a composition which includes one or more ANVP compounds together with a physiologically acceptable carrier. In general the dosage will range from about 0.01 to 100 $\mu$g/kg, more usually 0.1 to 10 $\mu$g/kg of the host body weight. Alternatively, dosages within these ranges can be administered by constant infusion over an extended period of time, usually exceeding 24 hours, until the desired therapeutic benefits have been obtained.

These compounds can be administered neat, as mixtures with other physiologically acceptable active or inactive materials, or with physiologically suitable carriers such as, for example, water or normal saline. The compounds can be administered orally, nasally or parenterally, for example, by injection. Injection can be subcutaneous, intravenous, or by intramuscular injection.

These compounds are desirably administered in pharmaceutically effective amounts and often as pharmacologically acceptable salts such as acid addition salts. Such salts can include, e.g., hydrochloride, hydrobromide, phosphate, sulphate, acetate, benzoate, malate, among others.

Compounds of the present invention can also be used for preparing antisera for use in immunoassays employing labelled reagents, usually antibodies. Conveniently, the peptide compounds can be conjugated to an antigen by means of dialdehydes, particularly from 4 to 6 carbon atoms and aliphatic, or carbodiimide. These compounds and immunologic reagents may be labelled with a variety of labels such as chromophores, fluorophores such as, e.g., fluorescein or rhodamine, radioisotopes such as $^{125}I$, $^{35}S$, $^{14}C$, or $^3H$, or magnetized particles, by means well known in the art.

These labeled compounds and reagents, or labeled reagents capable of recognizing and specifically binding to them, can find use as, e.g., diagnostic reagents. Samples derived from biological specimens can be assayed for the presence or amount of substances having a common antigenic determinant with compounds of the present invention. In addition, monoclonal antibodies can be prepared by methods known in the art, which antibodies can find therapeutic use, e.g., to neutralize overproduction of immunologically related compounds in vivo.

The following examples are provided by way of illustration, rather than implying any limitation of the subject invention.

EXPERIMENTAL

In the experimental disclosure which follows, pre-proANVPs, proANVPs and ANVPs derived from rat and human DNA sequences have amino acid residues numbered 1-152 and 1-151 respectively to indicate differences in the disclosed amino acid sequences. The amino acid sequence of chemically synthesized ANVPs are numbered from the arginine residue found at position 126 in the rat-derived sequence and position 127 in the human-derived sequence (see FIGS. 1 and 2).

I. ISOLATION AND PURIFICATION OF ATRIAL

Natriuretic/Vasodilator Peptide Compounds

Compounds within the scope of the present invention have been isolated from atrial tissue in accordance with the following protocol. These compounds and their synthetic peptide analogs are included in the collective term ANVPs.

A peptide compound was isolated from an acetic acid extract of atrial tissue, and was purified substantially free from unrelated tissue and products. Atria from 1400 male Wistar rats were homogenized in 8 volumes of 1 N acetic acid containing 1 mM phenylmethylsulfonyl fluoride (PMSF)(Sigma Chemical Co., St. Louis, Mo.), 3 mM ethylenediaminetetraacetic acid (EDTA) and 5 $\mu$M pepstatin A (pepsin and renin inhibitor, Sigma Chemical Co., St. Louis, Mo.). This homogenate was centrifuged at 10,800×g for 30 minutes and the pellet was rehomogenized in 4 volumes of the original buffer. The supernates from the extracts were pooled and neutralized with ammonium hydroxide. The neutralized supernatants were then centrifuged at 10,000×g for 20 minutes and lyophilized.

The lyophilized atrial extract was reconstituted in 6 ml buffer, centrifuged and loaded on a 2.5×45 cm gel filtration column of Sephadex ® G-50 (fine, Pharmacia Fine Chemicals, Piscataway, N.J.) previously equilibrated with 1 N acetic acid. Aliquots from each fraction were dried (Savant Speed-Vac concentrator), reconstituted in phosphate buffered saline (PBS) and assayed for natriuretic activity in intact rat and for vasorelaxant activity using rabbit aortic rings.

The results of this chromatographic step were as shown in FIG. 3A, and the regions contained in horizontal bracket were lyophilized, reconstituted with 0.1 % aqueous trifluoroacetic acid (TFA), pooled and centrifuged.

The pooled material was adjusted to 15% acetonitrile ($CH_3CN$) and applied to a 0.39×30.0 centimeter $\mu$-Bondapak $C_{18}$ column (Waters, Inc., Milford, MA), using a Waters U6K injector and solvent delivery system (Waters, Inc., Milford, Mass.). Bound material was eluted with a linear gradient of solvents A (0.1% TFA): B ($CH_3CN$) from 85:15 to 45:55 over 40 minutes.

Aliquots of the fractions were assayed for natriuresis in the isolated kidney and vasorelaxant activity as described subsequently. A broad region of coincident natriuretic and vasorelaxant activity was eluted and these fractions were pooled and dried.

The material obtained and dried was reconstituted in A:B, 78:22, and rechromatographed (in 12 separate applications) at 1.0 ml/min. using a gradient of 22 to 34% B over 48 minutes. Aliquots of the fractions were tested for natriuretic and vasorelaxant activities as described. The results were as displayed in FIG. 3B. Fractions from the three active peaks were pooled and dried overnight.

The combined fractions from the second peak (indicated by bracketed area in FIG. 3B) were reconstituted in A:B, 77:23, applied to a C18 column and eluted using a gradient of 23 to 29% B over 90 minutes. The results of this rechromatography were as shown in FIG. 3C, where the bracketed area indicates fractions with vasorelaxant activity. Active fractions from 6 applications were pooled.

The pooled material thus obtained was applied to a 0.39×30 cm $\mu$-Bondapak CN column (Waters, Inc., Milford, Mass.). The solvent system used was A (0.1% TFA in water) and B (0.055% TFA in $CH_3CN$). The sample was reconstituted in A:B, 90:10, and chromatographed in three separate applications at 0.6 ml/min. using a gradient of 10 to 30% B over 60 minutes. Vasorelaxant activity was determined by the reduction in tension produced in histamine-contracted aortic rings as described subsequently.

The most active peak, indicated by the bracket in FIG. 3D, was dried and sequenced. The sequence was determined from one nanomole of protein using the Applied Biosystems 470A gas-phase sequencer (Applied Biosystems Inc., Foster City, CA) in accordance with the instructions of the manufacturer. PTH amino acids were identified with a Beckman 334 T HPLC, using a 0.46×25 cm IBM CN-column. The gradient applied was as indicated in Hunkapiller, N. W. and L. E. Hood, *Methods in Enzymology*, 91:486–492 (Academic Press, N.Y.) (1983), with the following modifications: The binary gradient system was replaced by a ternary gradient system in which acetonitrile and methanol were pumped by separate pumps and the ratio of the two varied with time over the course of the gradient, with appropriate modification of the gradient program; the Permaphase ETH+ guard column was replaced with a 5×0.46 centimeter IBM CN analytical "mini-column", and the analytical column was heated to 28° C.

The compound, isolated substantially free from unrelated rat atrial tissue and products has the sequence
H-Arg-Ile-Asp-Arg-Ile-Gly-Gly-Arg-Ile-Asp-Arg-Ile-
  Gly-Ala-Gln-Ser-Gly-Leu-Gly-Cys-Asn-Ser-Phe-
  Arg-X where X=OH or Tyr-OH To provide comparison with the amino acid sequences of rat and human pre-proANVPs and proANVPs deduced from nucleotide sequences described below, the compounds are referred to as rANVp (126-149) where X=OH and rANVP (126-150) where X=Tyr-OH The human equivalents of these ANVPs, derived from the corresponding human DNA sequences described below, are referred to as hANVP (127-150) and hANVP (127-151), respectively. ANVP compounds of the present invention are numbered with the Amino-terminal arginine residue, disclosed above, numbered as described (i.e. 126-rat and 127-human).

The methods used to assay the products of the purification procedure ensure that natriuretic and vasorelaxant activity is an inherent property of the isolated and purified ANVP material.

II. RECOMBINANT DNA CLONING OF ATRIAL

Natriuretic/Vasodilator Peptides

In the examples that follow, deoxyribonucleic acid (DNA) sequences encoding rat and human derived preproANVPs and proANVPs are described. It is to be appreciated that numerous alternative sequences can be constructed which will direct the expression of peptide compound embodiments of the present invention.

A. CLONING OF RAT PRE-PROATRIAL NATRIURETIC/VASODILATOR PEPTIDE cDNA

Isolation of Rat Atrial mRNA

Total RNA was isolated from rat atria by the 5 method of Chirgwin, J. M. et al., Biochemistry 18:5294-299 (1979). The atrial tissue was homogenized in a solution of 6 M guanidine thiocyanate, 0.005 M sodium citrate, pH 7.0, 0.1 M β-Mercaptoethanol, 0.5% Sarcrosyl. This homogenate was made 2.0 M in CsCl and layered over a 5.7 M CsCl cushion in 0.1 M EDTA. The RNA was pelleted through this cushion by centrifugation at 115,000×g for 16 hours. The RNA was then dissolved in 0.01 M Tris buffer, pH 7.4, 0.005 M EDTA, 1.0% sodium dodecylsulfate (SDS), extracted with a 4:1 mixture of chloroform and 1-butanol, and precipitated from 70% ethanol.

The polyadenylated RNA (poly A+ RNA) fraction was obtained by affinity chromatography using oligo (dT) cellulose as described by Aviv, H. and P. Leder, Proc. Natl. Acad. Sci. USA 69:1408-1412 (1972). The poly A+ RNA was bound to the oligo (dT) cellulose matrix in a solution of 0.02 M Tris, pH 7.6, 0.001 M EDTA, 0.1% SDS, containing 0.5 M NaCl. The non-polyadenylated RNA was removed by washing the column with this solution. The poly A+ RNA was then eluted in the same solution minus NaCl, and precipitated from 70% ethanol. With these techniques, 100 µg of polyadenylated RNA was isolated from 10 gm of atrial tissue.

2. Generation of Rat Atrial cDNA Library

Double-stranded cDNA was synthesized and prepared for insertion into the plasmid vector pUC8 (Vieira, J. and J. Messing, Gene 19:259-268, 1982) using the sequential addition of EcoRI and SalI oligonucleotide linkers as described by Helfman, D. M. et al., Proc. Natl. Acad. Sci. USA 80:31-35 (1983).

First strand cDNA was synthesized by the RNA-dependent DNA polymerase from Avian Myeloblastosis Virus primed with oligo(dT)12-18 The RNA template was then removed by base hydrolysis. Second strand DNA was synthesized by RNA-dependent DNA polymerase, relying on self-priming at the 3'-end of the first strand molecule, thereby forming a double-stranded hairpin DNA. These molecules were blunt-ended at the openended termini using the large fragment of DNA polymerase I of E. coli to fill in single-stranded regions. EcoRI oligonucleotide linkers were added to the open-end using T4-DNA ligase. The hairpin loop was cleaved open with S₁ nuclease from Aspergillus oryzae and the termini of the molecules were again blunt-ended as before. SalI oligonucleotide linkers were then added, using T4-DNA ligase. SalI and EcoRI "sticky ends" were released by cleavage with these restriction endonucleases. These double-stranded double-linkered cDNA molecules were then ligated into EcoRI and SalI digested pUC8 and transferred into E. coli MC1061 by the CaCl₂-treatment described by Casabaden, M. and S. Cohen, J. Mol. Biol. 138:179-207 (1980).

Five µg of rat atrial poly A+ RNA yielded about 25 ng of cDNA, size selected to greater than 300 base pairs, and gave a library of about 200,000 independent recombinants. These recombinants were plated on nitrocellulose filters, replica plated and the library stored frozen on glycerol impregnated filters at −70° C. with the protocol of Hanahan, D. and M. Meselson, Gene 10:63-67 (1980) and Hanahan, D. and M. Meselson, *Methods in Enzymology*, Academic Press, N.Y., pp. 333-342 (1983).

3. Screening of the Rat Atrial cDNA Library

Amino acid sequences for native rat ANVNPs, as determined in Section I, were used to design oligonucleotide probes to screen the rat atrial cDNA library, as described in Wallace, R. B. et al., Nucleic Acids Res. 9:879-894 (1981)). Due to the degeneracy of the genetic code, two oligonucleotide pools were synthesized for each region. Region 1 was covered by two tetradecamer oligonucleotide pools, probe a and probe b, each consisting of 64 base sequences. Region 2 was covered by another two tetradecamer pools, probe c and probe d, each consisting of 72 sequences. The sequence and location of these oligonucleotide probes are shown in FIG. 4. The sequence of amino acids 4-13 of native rat ANVP is shown along with the sequence of the four oligonucleotide mixtures, probes a and b for region 1, and probes c and d for region 2, wherein R=A or G, Y=T or C, N=A,G,T or C. Each oligonucleotide mixture was synthesized on a Biosearch SAM I oligonucleotide synthesizer (Biosearch, Inc., San Rafael, Cal.) by a modification of the standard phosphotriester method using mesitylenesulfonyl chloride in the presence of N-methylimidazole as condensing reagents as described by Efimov, V. A. et al., Nuc. Acids Res. 10:6875-6894 (1982) and purified by polyacrylamide gel electrophoresis.

The cDNA library was then screened by colony hybridization using these probes. Four replica filters were prepared from each filter, so that each colony could be screened with each oligonucleotide probe pool.

The filters were baked for 2 hrs. at 80° C. under vacuum and then washed overnight at 68° C. with shaking in a large volume of 3X SSC (where 1X SSC is 0.15 M NaCl, 0.15 M sodium citrate, pH 7.5) 0.1% SDS. The filters were prehybridized in 6X SSC, 0.1% SDS, 1 mM EDTA, 5x Denhardt's solution, (0.1% Ficoll polyvinylpyrrolidone, 0.1% bovine serum albumin) 0.05% sodium pyrophosphate at 50° C. for a minimum of 2 hrs. Filters were then hybridized with 2.5×10⁶ cpm ³²P-labeled oligonucleotide probe mixture (phosphorylated in accordance with Maniatis, T. et.al., *Molecular Cloning*, Cold Spring Harbor Laboratories, 1982, pp. 122-123) per filter in 10 ml hybridization solution containing 100 µg/ml tRNA at 45° C. in a shaking water bath. After 1 hr., the thermostat was lowered to 25° C. and the bath allowed to equilibrate for 12 hrs. The filters were washed twice in 6X SSC, 0.1% SDS at room temperature for 15 mins., then washed in 6X SSC, 0.1% SDS at 35° C. (for probes c and d) or 39° C. (for probes a and b) for 1-2 mins. The final washing temperature was obtained from the empirical formula of Suggs, S. V. et al., *Developmental Biology Using Purified Genes* (ed.

D. D. Brown and C. F. Fox) Academic Press, N.Y. pp. 683-693, that is $T_d=4(G+C)+2(A+T)$. The hybridized filters were then dried and autoradiographed on Kodak® XAR film with Dupont® Cronex intensifying screens until complete exposures were obtained.

A colony was considered positive if it hybridized with one probe from region number 1 and one probe from region number 2. One colony was chosen which hybridized strongly to the oligonucleotide probes (pools a and c) and hybridized to a random primed atrial cDNA probe but not a ventricular cDNA probe. Sequencing of this clone demonstrated that it encoded rat pre-proANVPs. This clone is referred to as pNF1.

4. Complete Sequencing of the Rat Pre-proatrial Natiuretic/Vasodilator Peptides cDNA The purified DNA insert, obtained from pNF1, was prepared using small miniprep methods (Maniatis et al., supra at p. 366) and isolated on acrylamide gels. The intact DNA insert was then subcloned into bacteriophage M13 (a single stranded phage designed specifically for DNA sequencing using the dideoxynucleotide method as described by Messing J. and J. Vieira, Gene 19:259-268 (1982)), via the EcoRI and SalI sites on the 5' and 3' ends, respectively (FIG. 5). An initial reading of the entire sequence was then obtained from these clones using the Sanger dideoxynucleotide sequencing technique, Sanger, F. et al., Proc. Nat. Acad. Sci. USA 74:5463-5469 (1977). In order to confirm this initial sequence, a separate reading of the other DNA strand was necessary. For this, the HincII site at base 340 was used. The prepared insert was cleaved with endonuclease HincII, and the resulting digest was cloned into M13 mp9 cleaved with SmaI plus EcoRI (arrow 5) and M13 mp8 digested with SalI plus SmaI (arrow 6). A similar approach was taken using the PstI site at base 647 to obtain additional confirmation (arrows 3 and 4). Although the initial clone used for sequencing (pNF1) terminated at base 784 of the sequence (see FIG. 2), another clone (pNF4) extended further 3', containing the final 22 bases plus the 3' poly A tail. The sequence of the 3' end of this clone was obtained using M13 clones containing the PstI to SalI portion of the insert (arrow 7) and is shown in FIG. 2 as bases 785-806. Finally, the very 5'-terminal nucleotides of the DNA were determined by Maxam and Gilbert sequencing (Maxam, A. and W. Gilbert, Proc. Nat. Acad. Sci. USA 74:560-564 (1977)) of a 32P-labelled single-stranded DNA made complementary to the 5' region using the BglII fragment spanning bases 1-186. The sequence determined thereby was included in FIG. 2 as bases 1-22. Thus, nucleotide sequence analysis confirmed that clone pNF1, which includes bases 23-784 of FIG. 2, encodes an ANVP precursor, pre-proANVP. When the atrial cDNA library was re-screened with the cDNA insert, approximately 0.5% of the colonies hybridized. This indicates that pre-proANVP mRNA is a major species in the rat atrial mRNA population.

The amino acid sequence of native rat pre-proANVP was determined from the cDNA nucleotide sequence. A single open reading frame encoding a 152 amino acid sequence was disclosed, extending from the initiation codon ATG at base 85 to the termination codon TAA at position 541. Biologically active ANVPs (see FIG. 5) can be identified in the amino acid sequences of human and rat pre-proANVPs (see FIG. 1 and FIG. 2, respectively).

5. Determination of Atrial Specificity

Atrial and ventricular poly A+ RNA was subject to Northern blot analysis after fractionation by electrophoresis on a 1.4% agarose gel containing methylmercuric hydroxide by the method of Bailey, J. M. and N. Davidson, Anal. Biochem. 70:75-85 (1976). Northern blot analysis results, using nick translated pNF1 DNA, are shown in FIG. 6a where lane 1 contains atrial poly A+ RNA and lane 2 ventricular poly A+ RNA. As indicated in FIG. 6a, pNF1 hybridizes to an atrial mRNA of approximately 800-900 nucleotides in length. It does not hybridize with ventricular mRNA.

The cDNA sequence for pre-proANVP, determined above, indicates that pre-proANVP has a molecular weight of approximately 16,500 daltons. To determine the actual precursor size, atrial mRNA encoding pre-proANVP was purified by hybrid selection (Goldberg, M. L. et al., Methods in Enzymology 68:206-220, Academic Press, N.Y.), by immobilizing 5 μg pNF1 DNA on 1 cm² nitrocellulose discs and hybridizing with 5 μg of poly A+ RNA for 3 hrs. at 50° C. in 20 mM PIPES, pH 6.4, 1 mM EDTA, 65% formamide, 5X SSC, 0.1% SDS. The filters were washed extensively with 10 mM Tris-HCl, pH 7.5, 0.15 M NaCl, 1 mM EDTA, 0.1% SDS at 70° C. Thereafter filters were washed in the same buffer but without SDS. Hybridized RNA was eluted in H20 at 100° C. in the presence of 50 μg yeast tRNA for 1 min. and quickly frozen at −70° C. After thawing, the RNA was ethanol precipitated using 2 volumes of absolute ethanol.

Hybrid selected RNA and total poly A+ RNA was translated using a rabbit reticulocyte lysate system (Bethesda Research Labs, Gaithersburg, Md.) in the presence of 250 μCi/ml [35S]-methionine. Translation products were fractionated by 2-dimensional gel electrophoresis by loading 1×10⁶ cpm of acid-precipitable radioactivity per sample. The first dimension was an isoelectric focusing gel using a gradient from pH 3.5-10 (O'-Farrell, P. Z. et al., Cell 12:113-1142 (1977)). The results of t.he isoelectric focusing were subject to electrophoresis in an SDS-PAGE using a 15% gel. Following sodium salicylate equilibration, the gel was dried and then fluorgraphed at 70° C. for 24 hrs.

The results were as indicated in FIGS. 6b and 6c, where the position of several atrial-specific translation products having molecular weights between 12,000 and 30,000 daltons are marked by arrows. Translation products encoded by pNF1 hybrid-selected atrial RNA are indicated in FIG. 6d, which shows at least 3 related protein species having molecular weight between 18,000 and 20,000 daltons which are major atrial-specific species. FIG. 6e shows that hybrid selection does not recognize any ventricular-specific proteins. Because the proteins in FIG. 6d were hybrid selected, are atrial specific and are of the correct molecular weight range, they represent pre-proANVPs.

B. CLONING OF THE HUMAN GENE ENCODING PREPROATRIAL NATRIURETIC/VASODILATOR PEPTIDES

1. Isolation of the human native pre-proatrial natriuretic/vasodilator peptide gene The cDNA (isolated from pNF1) encoding rat pre-proANVP provided a probe for identifying the human gene. A human genomic clone library in bacteriophage Charon 4A (Lawn, R.M. et al , Cell 15:1157-1174

(1978)) was obtained from Dr. T. Maniatis, Harvard University. Approximately 106 phage were grown on *E. coli* K803, and plaque lysates were transferred to nitrocellulose filters as described by Benton, W. D. and R. W. Davis, Science 196:180-182 (1977). These filters were hybridized with the rat cDNA which had been radioactively labeled with $^{32}$P by the nick-translation method of Rigby, P. W. J. et al., J. Mol. Biol. 113:237-251 (1977). Filters were pre-washed in hybridization buffer (0.75 M NaCl, 0.75 M sodium nitrate, 40% formamide, 0.05% SDS, 0.02% bovine serum albumin, 0.02% Ficoll-400,000, 0.02% polyvinyl pyrollidone, 0.1% sodium pyrophosphate, 20 μg/ml denatured sheared salmon sperm DNA) at 42° C. for 1 hr. $5 \times 10^5$ cpm of $^{32}$P-labelled boiled rat pre-proANVP cDNA was added per ml of fresh hybridization buffer and the filters were incubated in this buffer at 42° C. for 16 hrs. Filters were then washed in 0.3 M NaCl, 0.3 M sodium nitrate and 05% SDS three times at 50° C., and exposed for autoradiography overnight. Six clones containing sequences hybridizing to rat native pre-proANVP cDNA were purified.

The size of the native human pre-proANVP gene was determined to permit identification of a full length clone. Two mg of high-molecular weight DNA was prepared from 20 gm of rat liver by the method of Blin, N. and D. Stafford, Nuc. Acid Res. 2303-2308 (1976). This DNA was digested with the restriction endonucleases BamHI, BglII, KpnI, and SacI, alone and in combination with EcoRI, electrophoresed on 1% agarose gels, and transferred to nitrocellulose filters by the method of Southern, E. M., J. Mol. Biol. 98:503-517 (1975). These filters were probed for sequences homologous to native rat pre-proANVPs by the same conditions used to identify the clones. In this manner a unique 2,600 base pair EcoRI-BamHI DNA fragment was identified which appeared to span the entire gene.

The six human genomic clones that hybridized to rat pre-proANVPs cDNA were then analyzed for the presence of a similarly sized fragment and one of them, designated λHG6, contained such a fragment.

λHG6 DNA was then digested with EcoRI and BamHI and DNA fragments were ligated into pBR322 previously digested with the same endonucleases. Ligation products were transfered into *E. coli* MC1061 cells as previously described. Plasmid pHGRBI was thusly generated among the clones to the other fragments, and identified by the colony hybridization procedure of Grunstein, M. and D. Hogness, Proc. Natl. Acad. Sci. USA 72:3961-3965 (1975). Hybridizations were performed as described above. pHGRBl was then sequenced and shown to contain the entire gene sequence for native human pre-proANVP.

2. Sequencing of the Human Native Ore-proatrial Natriuretic/Vasodilator Peptide Gene For the human gene, the 2589 base pair fragment shown to hybridize with the rat cDNA was prepared from a large-scale plasmid prep by 4% polyacrylamide gel electrophoresis. Before sequencing could proceed, the large size of the DNA segment dictated that several useful restriction endonuclease cleavage sites be determined which would break the sequence into smaller fragments. Particularly useful sites were found at positions 586 (SstI), 984 and 1839 (AvaI), and 1581 and 2374 (PstI). These sites are shown in FIG. 7 which portrays the human gene sequencing strategy consistent with methods described for rat cDNA in Section II.A.4. Several M13 subclones were prepared spanning the DNA segments between these sites in order to cover these regions on both DNA strands. The DNA fragments generated by restriction endonuclease cleavage and M13 subcloning are indicated in FIG. 7 by arrows 1-10. The resulting sequence is shown in FIG. 1A. The sequence information obtained was analyzed using various Intelligenetics (Palo Alto, California) computer programs in accordance with &he instructions of the manufacturer.

The regions containing the signal peptide, precursor sequence and mature peptide were identified by comparison to the rat native pre-proANVP cDNA. The entire coding region is contained within the BamHI to EcoRI fragment, and the coding region for the gene contains 2 introns of 122 and 1095 bases, and 3 exons spanning approximately bases 577-696, 819-1145 and 2241-2536. Putative control signals for both transcriptional initiation (bases 347-354 and 446-452) and termination (bases 2515-2520) were also localized within the fragment. The human equivalents of the rANVP isolated in Section I can be deduced within the second and third exons of the human gene.

C. Cloning Of Human Pre-proatrial Natriuretic/Vasodilator Peptide cDNA

1. Isolation of Human Fetal Heart mRNA

A human fetal heart, obtained at 26 weeks of gestation, was used to prepare poly A+ mRNA, as described in section II. From a total of 1.7 gm of heart tissue 60 μg of poly A+ mRNA was isolated.

2. Generation of Human Fetal Heart cDNA Library

Double stranded cDNA was prepared as described in Maniatis, T. et al., Molecular Cloning, Cold Spring Harbor Laboratories, 1982, pp. 212-246. Ten μg of the template RNA was copied into the first strand cDNA using AMV reverse transcriptase, primed with oligo dT$_{12-18}$. The RNA template was then removed by base hydrolysis and then double stranded. DNA was synthesized by AMV reverse transcriptase relying on self priming by the hairpin loop found naturally at the 3'-end of the first strand cDNA. The resulting double-stranded hairpin DNA was then treated with the S$_1$-nuclease from *Aspergqillus oryzae* to remove the hairpin loop, and the resulting molecules were treated with the large fragment of *E. coli* DNA polymerase I to make them blunt ended. EcoRI oligonucleotide linkers were added to the cDNA molecules using T$_4$-DNA ligase and the cohesive EcoRI ends were released by cleavage with the restriction enzyme EcoRI The resulting double stranded, EcoRI-linkered cDNA was then size fractionated on a Biogel A-50m column (BioRad, Richmond, CA) and 10 ng of cDNA greater than 500 bp long was recovered.

The size fractionated cDNA was then cloned into the bacteriophage λ-vector, λgt10, as described by Huynh, T. V. *et al., cDNA Cloning Technigues: A Practical Approach*, ed. D. Glover (IRL, Oxford) (1984) in press. DNA was prepared from λgt10 and digested with EcoRI. This DNA was ligated to the EcoRI-linkered human fetal heart cDNA and packaged in vitro using the packaging kit obtained from Amersham. The resulting phage were then plated on the *E. coli* strain BNN102 described by Huynh, T.V. et al., supra. In this way, a human fetal heart library of about 200,000 individual members was obtained and amplified for storage and subsequent screening.

3. Screening of the Human Fetal Heart cDNA Library

The cDNA library was screened by plaque hybridization as described by Maniatis, T. et al., supra, pp. 320-321. The hybridization probe was the EcoRI-SalI insert from the rat pre-proANVP, cDNA clone pNF1 (see Section II.A.3). This purified DNA fragment was labeled with $^{32}$P by nick translation using a kit available from Bethesda Research Laboratories, Bethesda, Md.

Using the amplified human fetal heart cDNA library, prepared as previously described, phage were plated out using the host strain BNNIC2. Nitrocellulose filters were lifted from these plates, baked for 2 hours at 80° C. under vacuum, and hybridized to $5 \times 10^5$ cpm of [$^{32}$P]-labelled rat pre-proANVP cDNA, pNF1 insert. Hybridization was performed in 40% formamide, 50 mM sodium phosphate, pH 6.5, 5X Denhardts solution (0.1% Ficoll, 0.14 M polyvinylpyridine, 0.1 % bovine serum albumin), 5X SSC, 50 μg/ml salmon sperm DNA and 50 μg/ml yeast RNA for 16 hours at 42° C. The filters were washed twice for 30 minutes in 1X SSC, 0.1% SDS at 50° C. and autoradiographed as previously described. A total of twenty hybridizing phage corresponding to human pre-proANVP cDNA clones were then identified.

4. Sequence Analysis of the Human Pre-proANVP cDNA Clone

Twelve of the hybridization-positive phage were chosen and purified to homogeneity by replating. Phage DNA preparations were made from these human pre-proANVP cDNA clones and the DNA was digested with EcoRI to determine the size of the cDNA insert. One clone, identified as number 6, was determined to have an insert of about 700 base pairs and was chosen for DNA sequence analysis.

The EcoRI insert of clone number 6 was subcloned into phage M13 vector (Messing J. & Vieira, J., Gene 19: 259-268 (1982)) and sequenced by the dideoxynucleotide chain termination method as described by Sanger, F. et al., supra.

The nucleotide sequence of the human pre-proANVP cDNA clone number 6 is shown in FIG. 1B. The clone was compared to the rat pre-proANVP cDNA to confirm that it corresponds to human pre-proANVP. This cDNA clone extends from the region corresponding to amino acid 15 through the human pre-proANVP coding region and contains all of the 3'-untranslated region. It therefore contains all of the sequences coding for the biologically active components of human proANVP and is suitable for expression in foreign systems.

III. Chemical Synthesis of Atrial Natriuretic/Vasodilatory Peptides

A. Synthesis Procedures

Compounds of the present invention having the general formula

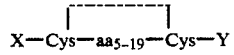

wherein each aa$_n$ is an amino acid residue of the general formula

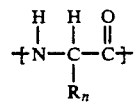

including any of the D-isomer, L-isomer and DL-isomer (racemic mixture) residues; and wherein R$_n$ is hydrogen or an aliphatic, aromatic or alkaryl group of from one to ten, usually one to six carbon atoms, including groups having substitutions of two or less nitrogen, oxygen or sulfur atoms as amido, thio or oxy, including hydroxy, thiol and ethers, wherein the ether is usually an alkyl ether, generally of one carbon atom, e.g. methyl;

X is hydrogen, amido, acetyl or additionally includes an oligopeptide of up to 125 amino acid residues, including N-acetyl and amido derivatives thereof;

Y is hydroxyl, amido or an oliqopeptide of up to 20 amino acid residues, including C-terminal amide derivatives thereof; and compounds of the present invention having the general formula:

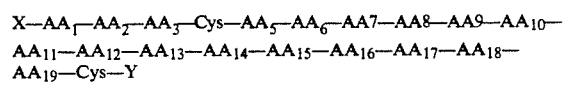

wherein

AA$_1$ is a basic polar amino acid residue, preferably selected from the group consisting of Arg and [D-Arg];

AA$_2$ and AA$_3$ are each independently a bond or the same or different neutral polar amino acid residues, preferably selected from the group consisting of Ser, [D-Ser], des AA$_2$ and des AA$_3$;

AA$_5$, AA$_9$, AA$_{12}$, AA$_{14}$ and AA$_{18}$ are each independently the same or different neutral nonpolar amino acid residues, preferably where AA$_5$ is selected from the group consisting of Phe, [D-Phe], Ala and Leu, AA$_9$ is selected from the group consisting of Ile, [D-Ile], Met, [D-Met], Val and [D-Val], AA$_{12}$ is selected from the group consisting of Ile, [D-Ile], Val and [D-Val], AA$_{14}$ is selected from the group consisting of Ala and [D-Ala], and AA$_{18}$ is selected from the group consisting of Leu and [D-Leu];

AA$_6$, AA$_7$, AA$_{13}$, AA$_{15}$, AA$_{16}$, AA$_{17}$ and AA$_{19}$ are each independently the same or different neutral amino acid residues, preferably where AA$_6$ is selected from the group consisting of Gly, Ala and [D-Ala], AA$_7$ is selected from the group consisting of Gly, Ala, D-Ala and Pro, AA$_{13}$ is selected from the group consisting of Gly, Ala and [D-Ala], AA$_{15}$ is selected from the group consisting of Gln and [D-Gln], AA$_{16}$ is selected from the group consisting of Ser and [D-Ser], AA$_{17}$ is selected from the group consisting of Gly, Ala and [D-Ala], and AA$_{19}$ is selected from the group consisting of Gly, Ala and [D-Ala];

AA$_8$ and AA$_{11}$ are each independently the same or different basic polar or neutral nonpolar amino acid residues, preferably selected from the group consisting of Arg, [D-Arg], Lys, [D-Lys] and Nle;

AA$_{10}$ is any acidic polar amino acid residues preferably selected from the group consisting of Asp and Glu; and X and Y are as previously defined,
were synthesized by solid-phase techniques. Syntheses were performed manually or, alternatively, on a Biosearch SAM II automated peptide synthesizer (Biosearch, San Rafael, Calif.) using t-Boc amino acids in accordance with the instructions of the manufacturer.

In accordance with the above description, the following procedures were used for the chemical synthesis of novel ANVPs.

PROCEDURE A

Preparation of Boc-AA$_1$ ... AA$_{n-1}$-AA$_n$-Resin

Hydroxymethyl Polystyrene Ester

One gm of Boc-AA$_n$-0-Polystyrene-Resin (0.2–0.6 mmole/g resin) is treated according to schedule A for incorporation of the Boc-AA$_{n-1}$-OH.

| | Schedule A |
|---|---|
| 1) | Wash 3× with dichloromethane (CH$_2$Cl$_2$); |
| 2) | Treat for 1 min. with TFA:CH$_2$Cl$_2$:ethane dithiol (EDT) (45:50:5 by volume); |
| 3) | Treat for 20 min. with TFA:CH$_2$Cl$_2$:EDT (45:50:5 by volume); |
| 4) | Wash 3× with CH$_2$Cl$_2$; |
| 5) | Treat 2× for 1 min. with 10% (V/V) Diisopropylethylamine (DIPEA) in CH$_2$Cl$_2$; |
| 6) | Wash 2× with CH$_2$Cl$_2$; |
| 7) | Wash 2× with methanol (MeOH); |
| 8) | Repeat (5-7) once; |
| 9) | Wash 3× with CH$_2$Cl$_2$; |
| 10) | Add 1-6 equivalents of preformed symmetrical anhydride of the suitably protected Boc-amino acid dissolved in CH$_2$Cl$_2$ or dimethyl formamide (DMF)/CH$_2$Cl$_2$ (50:50 volume) (Boc-Asn-OH and Boc-Ala-OH are coupled with active esters of N-hydroxybenzotriazole); |
| 11) | Wash 2× with CH$_2$Cl$_2$; |
| 12) | Wash 2× with 10% DIPEA in CH$_2$Cl$_2$ |
| 13) | Wash 2× with CH$_2$Cl$_2$; |
| 14) | Wash 2× with MeOH; |
| 15) | Wash 2× with CH$_2$Cl$_2$; |
| 16) | Repeat steps (11-15) once; |
| 17) | Test by ninhydrin reaction according to Kaiser et al., Annal. Biochem. 34:595 (1970). If the coupling reaction was incomplete, repeats steps (10-16) or, alternatively, cap synthesis using N-acetyl imidazole (0.30 M in DMF) or an excess of acetic anhydride in CH$_2$Cl$_2$. |

Procedure B

Preparation of Boc-AA$_n$-p-Methylbenzhydrylamine Resin

Boc-AA$_n$-OH is attached to a p-Methylbenzhydrylamine (pMBHA) resin via N,N'-dicyclohexylcarbodiimide, as described below.

| | Schedule B |
|---|---|
| 1) | Wash the p-MBHA.HCl resin; |
| 2) | Wash the resin 2× with 10% (V/V) DIPEA in CH$_2$Cl$_2$; |
| 3) | Wash 2× with CH$_2$Cl$_2$; |
| 4) | Wash 2× with MeOH; |
| 5) | Wash 2× with CH$_2$Cl$_2$; |
| 6) | Add 1-6 equivalents of preformed symmetrical anhydride of the suitably protected Boc-amino acid dissolved in CH$_2$Cl$_2$, with a reaction time of from approximately 0.5–24 hrs. |

Unreacted amino groups are acetylated with 0.30 M N-acetylimidazole:DMF, or acetic anhydride:CH$_2$Cl$_2$ The first two examples demonstrate the chemical synthesis of ANVP peptides that were originally isolated from rat atria (see Section I).

Example III.A.1: rANVP(126-150)

H-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr-OH

One gm of Boc L-Tyr(BrZ)0-Resin (0.54 meq/gm, Peninsula Labs Inc., Belmont, Calif.) was subjected to procedure A with the required sequence of amino acids (introduced in order as Boc-Arg(Tos)OH, Boc-PheOH, Boc-Ser(Bzl)OH, Boc-AsnOH, Boc-Cys(4-CH$_3$Bzl)OH, Boc-GlyOH, Boc-LeuOH.H$_2$O, Boc-GlyOH, Boc-Ser(Bzl)OH, Boc-GlnOH, BocAlaOH, Boc-GlyOH, Boc-IleOH.½H$_2$O, Boc-Arg(Tos)OH, Boc-Asp(OBzl)OH, Boc-IleOH.½H$_2$O, Boc-Arg(Tos)OH, Boc-GlyOH, Boc-GlyOH, Boc-PheOH, Boc-Cys(4CH$_3$Bzl)OH, Boc-Ser(Bzl)OH, Boc-Ser(Bzl)OH, Boc-Arg(Tos)OH). The protected peptidyl resin was treated with TFA:CH$_2$Cl$_2$:EDT (45:50:5, v/v/v) for 1 min., then 20 min. and washed 3 times with CH$_2$Cl$_2$, 2 times with MeOH to give the TFA salt of the peptidyl resin and dried in vacuo.

The peptidyl resin was then suspended in anhydrous hydrogen fluoride (HF) containing 10% anisole, 2% ethyl methyl sulfide for 30 min. at $-10°$ C., and 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once with diethylether. The peptide was extracted from the mixture with 2.0 M acetic acid, diluted with H$_2$O and lyophilized, to give the unoxidized dihydro peptide.

The crude peptide was dissolved in deoxygenated 0.01 M ammonium acetate (NH$_4$OAc), pH 8, to 0.5 mg/ml and then oxidized by dropwise additior of a slight excess of 0.01 M potassium ferricyanide (KCN) solution stirred 20 minutes and adjusted to pH 5 with acetic acid. The peptide solution was treated with DOWEX AG3X4 anion exchange resin, filtered, diluted with H$_2$O and lyophilized to give the crude cyclized peptide.

Purification of the peptide was achieved by desalting on Sephadex ® G-25F using 0.5 M AcOH as eluant, followed by ion exchange chromatography on CM-Sepharose ® (Pharmacia Fine Chemicals) or CM-cellulose (Whatman) using an elution gradient generated by addition of 300 mM NH$_4$OAc, to a solution of 0.01 M NH$_4$OAc, pH 4.5. Fractions were collected having a minimum 97% purity, as judged by reversed phase HPLC, then pooled and lyophilized from H$_2$O several times to yield the purified rANVP(126-150) acetate salt.

Example III.A.2: rANVP(126-149)

H-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-OH 1.2 gm of Boc-Arg(Tos)0-Resin (Biosearch, Inc., San Rafael, Calif.) was subjected to procedure A with the required sequence of amino acids (introduced in order as Boc-PheOH, Boc-Ser(Bzl)OH, Boc-AsnOH, Boc-Cys(4-CH3Bzl)OH, Boc-GlyOH, Boc-LeuOH.H$_2$O, Boc-GlyOH, Boc-Ser(Bzl)OH, Boc-GlnOH, BocAlaOH, Boc-GlyOH, Boc-IleOH.1/2H20, Boc-Arg(Tos)OH, Boc-Asp(OBzl)OH, Boc-IleOH.1/2H$_2$O, Bcc- Arg(Tos)OH, Boc-GlyOH, Boc-GlyOH, Boc-PheOH, Boc-Cys(4CH3Bzl)OH, Boc-Ser(Bzl)OH, Boc-Ser(Bzl)OH, Boc-Arg(Tos)OH). The protected peptidyl resin was treated with TFA:CH2Cl2:EDT (45:50:5, v/v/v) for 1 min., then 20 min. and washed 3 times with CH2Cl2, 2 times with MeOH to give the TFA salt of the peptidyl resin and dried in vacuo.

The peptidyl resin was then suspended in anhydrous HF containing 10% anisole, 2% ethyl methyl sulfide for 30 min. at −10° C., and 30 min. at 0° C. The removed by evaporation under vacuum and the peptide/resin mixture was suspended in diethyl ether. The peptide/resin mixture was washed twice with diethyl ether, twice with chloroform, and twice with diethyl ether. The peptide was extracted with 2.0 M acetic acid and lyophilized, to give the unoxidized dihydro peptide.

The crude peptide was dissolved in 2.0 M acetic acid, 10 mM β-mercaptoethanol and was chromatographed on a Sephadex ® G-25SF column in the same solution. The peptide was then lyophillized and resuspended in a solution of 0.1 M NH4HCO3, pH 8.0 at a peptide concentration of 100 μg/ml. The suspended peptide was exposed to air for 48 hours to promote slow reoxidation. The peptide was then lyophillized.

Example III.A.3: hANVP(127-151)

H-Arg-Ser-Ser-Cys-Phe-Gly-Gly-Arg-Met-Asp-Arg-
Ile-Gly-Ala-Gln-Ser-Gly-Leu-Gly-Cys-Asn-Ser-
Phe-Arg-Tyr-OH

One gm of Boc-L-Tyr(BrZ)0-Resin (0.54 meg/gm, Peninsula Labs Inc., Belmont, Calif.) was subjected to procedure A with the required sequence of amino acids (introduced in order as Boc-Arg(Tos)OH, Boc-PheOH, Boc-Ser(Bzl)OH, Boc-AsnOH, Boc-Cys(4-CH3Bzl)OH, Boc-GlyOH, Boc-LeuOH.H2O, Boc-GlyOH, Boc-Ser(Bzl)OH, Boc-GlnOH, BocAlaOH, Boc-GlyOH, Boc-IleOH.1/2H2O, Boc-Arg(Tos)OH, Boc-Asp(OBzl)OH, Boc-MetOH.1/2H2O, Boc-Arg(Tos)OH, Boc-GlyOH, Boc-GlyOH. Boc-PheOH, Boc-Cys(4CH3Bzl)OH, Boc-Ser(Bzl)OH, Boc-Ser(Bzl)OH, Boc-Arg(Tos)OH). The protected peptidyl resin was treated with TFA:CH2Cl2 EDT (45:50:5, v/v/v) for 1 min., then 20 min. and washed 3 times with CH2Cl2 and twice with MeOH to give the TFA salt of the peptidyl resin and dried in vacuo.

The peptidyl resin was then suspended in anhydrous HF containing 10% anisole, 2% ethyl methyl sulfide for 30 min. at −10° C., and 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once with diethyl ether. The peptide was extracted from the mixture with 2.0 M acetic acid, diluted with H20 and lyophilized, to give the unoxidized dihydro peptide.

The crude peptide was dissolved in deoxygenated 0.01 M NH4OAc, pH 8, to 0.5 mg/ml and then oxidized by dropwise addition of a slight excess of 0.01 M potassium ferricyanide (KCN) solution stirred 20 minutes and adjusted to pH 5 with acetic acid. The peptide solution was treated with DOWEX AG3X4 anion exchange resin, filtered, diluted wi&:h H20 and lyophilized to give the crude cyclized peptide.

Purification of the peptide was achieved by desalting on Sephadex ® G-25F using 0.5 M AcOH as eluant, followed by ion exchange chromatography on CM-Sepharose ® or CM-cellulose (Whatman) using an elution gradient generated by addition of 300 mM NH4OAc, to a solution of 0.01 M NH4OAc, pH 4.5. Fractions were collected having a minimum 97% purity, as judged by reversed phase HPLC, then pooled and lyophilized from H2O several times to yield the purified hANVP(127-151) acetate salt.

* Example III.A.4: rANVP (126–148)-$NH_2$

H-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-$NH_2$

One gm of Boc-Phe-pMBHA-Resin was obtained using schedule B, and was subjected to procedure A with the required sequence of amino acids (introduced in order as Boc-Ser(Bzl)OH, Boc-AsnOH, Boc-Cys(4-CH3Bzl)OH, Boc-GlyOH, Boc-LeuOH.$H_2O$, Boc-GlyOH, Boc-Ser(Bzl)OH, Boc-GlnOH, Boc-AlaOH, Boc-GlyOH, Boc-IleOH.1/2$H_2O$, Boc-Arg(Tos)OH, Boc-Asp(OBzl)OH, Boc-IleOH.1/2$H_2O$, Boc-Arg(Tos)OH, Boc-GlyOH, Boc-GlyOH, Boc-PheOH, Boc-Cys(4-CH3Bzl)OH Boc-Ser(Bzl)OH, Boc-Ser(Bzl)OH, Boc-Arg(Tos)OH).

The peptidyl resin was then suspended in anhydrous HF containing 10% anisole, 2% ethyl xethyl sulfide for 30 min. at −10° C., and 30 min. at 0° C. The HF was removed by evaporation under vacuum and the peptide/resin mixture was suspended in diethyl ether. The peptide/resin mixture was washed twice with diethyl ether, once with chloroform, once with diethyl ether, once with chloroform and once with diethylether. The peptide was extracted from the mixture with 2.0 M acetic acid, diluted with $H_2O$ and lyophilized, to give the unoxidized dihydro peptide.

The crude peptide was dissolved in deoxygenated 0.01 M $NH_4OAc$, pH 8, to 0.5 mg/ml and then oxidized by dropwise addition of a slight excess of 0.01 M KCN solution, stirred 20 minutes and adjusted to pH 5 with acetic acid. The peptide solution was treated with DOWEX AG3X4 anion exchange resin, filtered, diluted with $H_2O$ and lyophilized to give the crude cyclized peptide.

Purification of the peptide was achieved by desalting on Sephadex ® G-25F using 0.5 M AcOH as eluant, followed by ion exchange chromatography on CM-Sepharose ® or CM-cellulose (Whatman) using a gradient elution generated by addition of 300 mM NH40Ac to a solution of 0.01 M $NH_4OAc$, pH 4.5. Fractions were collected having a minimum 97% purity, as judged by reversed phase HPLC, then pooled and lyophilized from $H_2O$ several times to yield the purified rANVP(126-148) acetate salt.

Following the procedures outlined in Examples III A.1-4, with appropriate modification, the following ANVP compounds are synthesized:

* Ex. III.A.5; rANVP(126—150)—HN₂

H-Arg-Ser-Ser-Cys-Phe-Gly-Gly-Arg-Ile-Asp-Arg-Ile-Gly-Ala-Gln-Ser-Glyn-Leu-Gly-Cys-Asn-Ser-Phe-Arg-Tyr-$NH_2$ Ex. III.A.6: hANVP(127—151)-$NH_2$ H-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr-$NH_2$ \* Ex. III.A.7: nANVP(127-150)

A-Arg-Ser-Ser-Cys-Phe-Gly-Gly-Arg-Met-Asp-Arg-
Ile-Gly-Ala-Gln-Ser-Gly-Leu-Gly-Cys-Asn-Ser-
Phe-Arg-OH

Ex. III.A.8: hANVP(127—150)—NH$_2$

H-Arg-Ser-Ser-Cys-Phe-Gly-Gly-Arg-Met-Asp-Arg-
Ile-Gly-Ala-Gln-Ser-Gly-Leu-Gly-Cys-Asn-Ser-
Phe-Arg-NH$_2$

Ex. III.A.9: rANVP(126—149)—NH$_2$

H-Arg-Ser-Ser-Cys-Phe-Gly-Gly-Arg-Ile-Asp-Arg-
Ile-Gly-Ala-Gln-Ser-Gly-Leu-Gly-Cys-Asn-Ser-
Phe-Arg-NH$_2$

\* Ex. III.A.10: rANVP(126—145)—NH$_2$

H-Arg-Ser-Ser-Cys-Phe-Gly-Gly-Arg-Ile-Asp-Arg-
Ile-Gly-Ala-Gln-Ser-Gly-Leu-Gly-Cys-NH$_2$

\* Ex. III.A.11: rANVP(126-145)

H-Arg-Ser-Ser-Cys-Phe-Gly-Gly-Arg-Ile-Asp-Arg-
Ile-Gly-Ala-Gln-Ser-Gly-Leu-Gly-Cys-OH

\* Ex. III.A.12: hANVP(127-149)

A-Arg-Ser-Ser-Cys-Phe-Gly-Gly-Arg-Met-Asp-Arg-
Ile-Gly-Ala-Gln-Ser-Gly-Leu-Gly-Cys-Asn-Ser-
Phe-OH

\* Ex. III.A.13: hANVP(127—149)—NH$_2$

H-Arg-Ser-Ser-Cys-Phe-Gly-Gly-Arg-Met-Asp-Arg-
Ile-Gly-Ala-Gln-Ser-Gly-Leu-Gly-Cys-Asn-Ser-
Phe-NH$_2$

\* Ex. III.A.14: hANVP(127-146)

H-Arg-Ser-Ser-Cys-Phe-Gly-Gly-Arg-Met-Asp-Arg-
Ile-Gly-Ala-Gln-Ser-Gly-Leu-Gly-Cys-OH

Ex. III.A.15: hANVP: hANVP(127-146)-NH$_2$

H-Arg-Ser-Ser-Cys-Phe-Gly-Gly-Arg-Met-Asp-Arg-
Ile-Gly-Ala-Gln-Ser-gly-Leu-Gly-Cys-NH$_2$ \* Ex. III.A.16: [D-Cys$^{129}$]rANVP(126-150)

H-Arg-Ser-Ser-[D-Cys]-Phe-Gly-Gly-Arg-Ile-Asp-
Arg-Ile-Gly-Ala-Gln-Ser-Gly-Leu-Gly-Cys-Asn-
Ser-Phe-Arg-Tyr-OH

Ex. III.A.17: [D-Cys$^{129}$]rANVP(126-150)-NH$_2$

H-Arg-Ser-Ser-[D-Cys]-Phe-Gly-Gly-Arg-Ile-Asp-
Arg-Ile-Gly-Ala-Gln-Ser-gly-Leu-Gly-Cys-Asn-Ser-
Phe-Arg-Tyr-NH$_2$ Ex. III.A.18: [D-Cys$^{129}$]rANVP(126-149)

H-Arg-Ser-Ser-[D-Cys]-Phe-Gly-Gly-Arg-Met-Asp-
Arg-Ile-Gly-Ala-Gln-Ser-Gly-Leu-Gly-Cys-Asn-
Ser-Phe-Arg-OH

Ex. III.A.19: [D-Cys$^{129}$]rANVP(126-149)-NH$_2$

H-Arg-Ser-Ser-[D-Cys]-Phe-Gly-Gly-Arg-Ile-Asp-
Arg-Ile-Gly-Ala-Gln-Ser-Gly-Leu-Gly-Cys-Asn-
Ser-Phe-Arg-NH$_2$

Ex. III.A.20: [D-Cys$^{129}$]rANVP(126-148)-NH$_2$

H-Arg-Ser-Ser-[D-Cys]-Phe-Gly-Gly-Arg-Ile-Asp-
Arg-Ile-Gly-Ala-Gln-Ser-Gly-Leu-Gly-Cys-Asn-
Ser-Phe-Phe-NH$_2$

Ex. III.A.21: [D-Cys$^{129}$]rANVP(126—145)—NH$_2$

H-Arg-Ser-Ser-[D-Cys]-Phe-Gly-Gly-Arg-Ile-Asp-
Arg-Ile-Gly-Ala-Gln-Ser-gly-Leu-Gly-Cys-NH$_2$ Ex. III.A.22: [D-Cys$^{130}$]hANVP(127-151)

H-Arg-Ser-Ser-[D-Cys]-Phe-Gly-Gly-Arg-Met-Asp-
Arg-Ile-Gly-Ala-Gln-Ser-Gly-Leu-Gly-Cys-Asn-
Ser-Phe-Arg-Tyr-OH

Ex. III.A.23: [D-Cys$^{130}$]hANVP(127—151)—NH$_2$

H-Arg-Ser-Ser-[D-Cys]-Phe-Gly-Gly-Arg-Met-Asp-
Arg-Ile-Gly-Ala-Gln-Ser-Gly-Leu-Gly-Cys-Asn-
Ser-Phe-Arg-Tyr-NH$_2$

Ex. III.A.24: [D-Cys$^{130}$]hANVP(127-150)

H-Arg-Ser-Ser-[D-Cys]-Phe-Gly-Gly-Arg-Met-Asp-
Arg-Ile-Gly-Ala-Gln-Ser-Gly-Leu-Gly-Cys-Asn-
Ser-Phe-Arg-OH

Ex. III.A.25: [D-Cys$^{130}$]hANVP(127—150)—NH$_2$

H-Arg-Ser-Ser-[D-Cys]-Phe-Gly-Gly-Arg-Met-Asp-
Arg-Ile-Gly-Ala-Gln-Ser-Gly-Leu-Gly-Cys-Asn-
Ser-Phe-Arg-NH$_2$

Ex. III.A.26: [D-Cys$^{130}$]hANVP(127—149)—NH$_2$

H-Arg-Ser-Ser-[D-Cys]-Phe-Gly-Gly-Arg-Met-Asp-
Arg-Ile-Gly-Ala-Gln-Ser-Gly-Leu-Gly-Cys-Asn-
Ser-Phe-NH$_2$

Ex. III.A.27: [D-Cys$^{130}$]hANVP(127—146)—NH$_2$

H-Arg-Ser-Ser-[D-Cys]-Phe-Gly-Gly-Arg-Met-Asp-
Arg-Ile-Gly-Ala-Gln-Ser-Gly-Leu-Gly-Cys-NH$_2$

\* Ex. III.A.28: [D-Phe130]rANVP(126-150)

H-Arg-Ser-Ser-Cys-[D-Phe]-Gly-Gly-Arg-Ile-Asp-
Arg-Ile-Gly-Ala-Gln-Ser-Gly-Leu-Gly-Cys-Asn-
Ser-Phe-Arg-Tyr-OH

\* Ex. III.A.29: [D-Ala$^{131}$]rANVP(126-150)

H-Arg-Ser-Ser-Cys-Phe-[D-Ala]-Gly-Arg-Ile-Asp-
Arg-Ile-Gly-Ala-Gln-Ser-Gly-Leu-Gly-Cys-Asn-
Ser-Phe-Arg-Tyr-OH

Ex. III.A.30: [D-Ala$^{131}$]rANVP(126—150)—NH$_2$

H-Arg-Ser-Ser-Cys-Phe-[D-Ala]-Gly-Arg-Ile-Asp-
Arg-Ile-Gly-Ala-Gln-Ser-Gly-Leu-Gly-Cys-Asn-
Ser-Phe-Arg-Tyr-NH$_2$

Ex. III.A.31: [D-Ala$^{131}$]rANVP(126-149)

H-Arg-Ser-Ser-Cys-Phe-[D-Ala]-Gly-Arg-Ile-Asp-
Arg-Ile-Gly-Ala-Gln-Ser-Gly-Leu-Gly-Cys-Asn-
Ser-Phe-Arg-OH

Ex. III.A.32: [D-Ala$^{131}$]rANVP(126—149)—NH$_2$

H-Arg-Ser-Ser-Cys-Phe-[D-Ala]-Gly-Arg-Ile-Asp-
Arg-Ile-Gly-Ala-Gln-Ser-Gly-Leu-Gly-Cys-Asn-
Ser-Phe-Arg-NH$_2$

\* Ex. III.A.33: [D-Ala$^{131}$]rANVP(126—148)—NH$_2$

H-Arg-Ser-Ser-Cys-Phe-[D-Ala]-Gly-Arg-Ile-Asp-
Arg-Ile-Gly-Ala-Gln-Ser-Gly-Leu-Gly-Cys-Asn-
Ser-Phe-NH$_2$

Ex. III.A.34: [D-Ala$^{131}$]rANVP(126—145)—NH$_2$

H-Arg-Ser-Ser-Cys-Phe-[D-Ala]-Gly-Arg-Ile-Asp-
Arg-Ile-Gly-Ala-Gln-Ser-Gly-Leu-Gly-Cys-NH$_2$

Ex. III.A.35: [D-Ala$^{132}$]hANVP(127-151)

H-Arg-Ser-Ser-Cys-Phe-[D-Ala]-Gly-Arg-Met-Asp-
Arg-Ile-Gly-Ala-Gln-Ser-Gly-Leu-Gly-Cys-Asn-
Ser-Phe-Arg-Tyr-OH

Ex. III.A.36: [D-Ala$^{132}$]hANVP(127—151)—NH$_2$

H-Arg-Ser-Ser-Cys-Phe-[D-Ala]-Gly-Arg-Met-Asp-
Arg-Ile-Gly-Ala-Gln-Ser-Gly-Leu-Gly-Cys-Asn-
Ser-Phe-Arg-Tyr-NH$_2$

Ex. III.A.37: [D-Ala$^{132}$]hANVP(127-150)

H-Arg-Ser-Ser-Cys-Phe-[D-Ala]-Gly-Arg-Met-Asp-
Arg-Ile-Gly-Ala-Gln-Ser-Gly-Leu-Gly-Cys-Asn-
Ser-Phe-Arg-OH

Ex. III.A.38: [D-Ala$^{132}$]hANVP(127—150)—NH$_2$

H-Arg-Ser-Ser-Cys-Phe-[D-Ala]-Gly-Arg-Met-Asp-
Arg-Ile-Gly-Ala-Gln-Ser-Gly-Leu-Gly-Cys-Asn-
Ser-Phe-Arg-NH$_2$

Ex. III.A.39: [D-Ala$^{132}$]hANVP(127—149)—NH$_2$

H-Arg-Ser-Ser-Cys-Phe-[D-Ala]-Gly-Arg-Met-Asp-
Arg-Ile-Gly-Ala-Gln-Ser-Gly-Leu-Gly-Cys-Asn-
Ser-Phe-NH$_2$

Ex. III.A.40: [D-Ala$^{132}$]hANVP(127—146)—NH$_2$

H-Arg-Ser-Ser-Cys-Phe-[D-Ala]-Gly-Arg-Met-Asp-
Arg-Ile-Gly-Ala-Gln-Ser-Gly-Leu-Gly-Cys-NH$_2$

* Ex. III.A.41: [D-Ala$^{132}$]rANVP(126-150)

H-Arg-Ser-Ser-Cys-Phe-Gly-[D-Ala]-Arg-Ile-Asp-
Arg-Ile-Gly-Ala-Gln-Ser-Gly-Leu-Gly-Cys-Asn-
Ser-Phe-Arg-Tyr-OH

Ex. III.A.42: [D-Ala$^{132}$]rANVP(126—150)—NH$_2$

H-Arg-Ser-Ser-Cys-Phe-Gly-[D-Ala]-Arg-Ile-Asp-
Arg-Ile-Gly-Ala-Gln-Ser-Gly-Leu-Gly-Cys-Asn-
Ser-Phe-Arg-Tyr-NH$_2$

Ex. III.A.43: [D-Ala$^{132}$]rANVP(126-149)

H-Arg-Ser-Ser-Cys-Phe-Gly-[D-Ala]-Arg-Ile-Asp-
Arg-Ile-Gly-Ala-Gln-Ser-Gly-Leu-Gly-Cys-Asn-
Ser-Phe-Arg-OH

Ex. III.A.44: [D-Ala$^{132}$]rANVP(126-149)—NH$_2$

H-Arg-Ser-Ser-Cys-Phe-Gly-[D-Ala]-Arg-Ile-Asp-
Arg-Ile-Gly-Ala-Gln-Ser-Gly-Leu-Gly-Cys-Asn-
Ser-Phe-Arg-NH$_2$

Ex. III.A.45: [D-Ala$^{132}$]rANVP(126—148)—NH$_2$

H-Arg-Ser-Ser-Cys-Phe-Gly-[D-Ala]-Arg-Ile-Asp-
Arg-Ile-Gly-Ala-Gln-Ser-Gly-Leu-Gly-Cys-Asn-
Ser-Phe-NH$_2$

Ex. III.A.47: [D-Ala$^{132}$]rANVP(126—145)—NH$_2$

H-Arg-Ser-Ser-Cys-Phe-Gly-[D-Ala]-Arg-Ile-Asp-
Arg-Ile-Gly-Ala-Gln-Ser-Gly-Leu-Gly-Cys-NH$_2$

Ex. III.A.47: [D-Ala$^{133}$]hANVP(127-151)

H-Arg-Ser-Ser-Cys-Phe-Gly-[D-Ala]-Arg-Met-Asp-
Arg-Ile-Gly-Ala-Gln-Ser-Gly-Leu-Gly-Cys-Asn-
Ser-Phe-Arg-Tyr-OH

Ex. III.A.48: [D-Ala$^{133}$]hANVP(127—151)—NH$_2$

H-Arg-Ser-Ser-Cys-Phe-Gly-[D-Ala]-Arg-Met-Asp-
Arg-Ile-Gly-Ala-Gln-Ser-Gly-Leu-Gly-Cys-Asn-
Ser-Phe-Arg-Tyr-NH$_2$

Ex. III.A.49: [D-Ala$^{133}$]hANVP(127-150)

H-Arg-Ser-Ser-Cys-Phe-Gly-[D-Ala]-Arg-Met-Asp-
Arg-Ile-Gly-Ala-Gln-Ser-Gly-Leu-Gly-Cys-Asn-
Ser-Phe-Arg-OH

Ex. III.A.50: [D-Ala$^{133}$]hANVP(127—150)—NH$_2$

H-Arg-Ser-Ser-Cys-Phe-Gly-[D-Ala]-Arg-Met-Asp-
Arg-Ile-Gly-Ala-Gln-Ser-Gly-Leu-Gly-Cys-Asn-
Ser-Phe-Arg-NH$_2$

Ex. III.A.51: [D-Ala$^{133}$]hANVP(127—194)—NH$_2$

H-Arg-Met-Asp-Arg-Ile-Gly-[D-Ala]Arg-Met-Asp-
Arg-Ile-Gly-Ala-Gln-Ser-Gly-Leu-Gly-Cys-Asn-
Ser-Phe-NH$_2$

Ex. III.A.52: [D-Ala$^{133}$]hANVP(127—146)—NH$_2$

H-Arg-Ser-Ser-Cys-Phe-Gly-[D-Ala]-Arg-Met-Asp-
Arg-Ile-Gly-Ala-Gln-Ser-Gly-Leu-Gly-Cys-NH$_2$

* Ex. III.A. 53: [D-Arg$^{133}$]rANVP(126-150)

H-Arg-Ser-Ser-Cys-Phe-Gly-[D-Ala]-Ile-Asp-Arg-Ile-
Gly-Ala-Gln-Ser-Gly-Leu-Gly-Cys-Asn-Ser-Phe-
Arg-Tyr-OH

Ex. III.A.54: [D-Met$^{135}$]hANVP(127-151)

H-Arg-Ser-Ser-Cys-Phe-Gly-Arg-[D-Met]-Asp-Arg-
Ile-Gly-Ala-Gln-Ser-Gly-Leu-Gly-Cys-Asn-Ser-
Phe-Arg-Tyr-OH

* Ex. III.A.55: [D-Val$^{134}$]rANVP(126-150)

H-Arg-Ser-Ser-Cys-Phe-Gly-Arg-[D-Val]-Asp-Arg-
Ile-Gly-Ala-Gln-Ser-Gly-Leu-Gly-Cys-Asn-Ser-
Phe-Arg-Tyr-OH

* Ex. III.A.56: [D-Arg$^{136}$]rANVP(126-150)

H-Arg-Ser-Ser-Cys-Phe-Gly-Arg-Met-Asp[D-Arg]-
Ile-Gly-Ala-Gln-Ser-Gly-Leu-Gly-Cys-Asn-Ser-
Phe-Arg-Tyr-OH

* Ex. III.A.57: [D-Val$^{137}$]rANVP(126-150)

H-Arg-Ser-Ser-Cys-Phe-Gly-Gly-Arg-Ile-Asp-Arg-
[D-Val]-Gly-Ala-Gln-Ser-Gly-Leu-Gly-Cys-Asn-
Ser-Phe-Arg-Tyr-OH

* Ex. III.A.58: [D-Ala$^{138}$]rANVP(126-150)

H-Arg-Ser-Ser-Cys-Phe-Gly-Gly-Arg-Ile-Asp-Arg-
Ile-[D-Ala]-Ala-Gln-Ser-Gly-Leu-Gly-Cys-Asn-Ser-
Phe-Arg-Tyr-OH

* Ex. III.A.59: [D-Ala$^{139}$]rANVP(126-150)

H-Arg-Ser-Ser-Cys-Phe-Gly-Gly-Arg-Met-Asp-Arg-
Ile-Gly[D-Ala]-Gln-Ser-Gly-Leu-Gly-Cys-Asn-Ser-
Phe-Arg-Tyr-OH

* Ex. III.A.60: [D-Gln¹⁴⁰]rANVP(126-150)

H-Arg-Ser-Ser-Cys-Phe-Gly-Gly-Arg-Ile-Gly-Ala-[D-Gln]-Ser-Gly-Leu-Gly-Cys-Asn-Ser-Phe-Arg-tyr-OH

* Ex. III.A.61: [D-Ser¹⁴¹]rANVP(126-150)

H-Arg-Ser-Ser-Cys-Phe-Gly-Gly-Arg-Ile-Asp-Arg-Ile-Gly-Ala-Gln-[D-Ser]-Gly-Leu-Gly-Cys-Asn-Ser-Phe-Arg-Tyr-OH

* Ex. III.A.62: [D-Val¹⁴²]rANVP(126-150)

H-Arg-Ser-Ser-Cys-Phe-Gly-Gly-Arg-Ile-Asp-Arg-Ile-Gly-Ala-gln-Ser-[D-Ala]-Leu-Gly-Cys-Asn-Ser-Phe-Arg-Tyr-OH Ex. III.A.63: [D-Ala¹⁴²]rANVP(126—150)—NH₂

H-Arg-Ser-Ser-Cys-Phe-Gly-Gly-Arg-Ile-Asp-Arg-Ile-Gly-Ala-gln-Ser-[D-Ala]-Leu-Gly-Cys-Asn-Ser-Phe-Arg-Tyr-NH₂

Ex. III.A.64: [D-Ala¹⁴²]rANVP(126-149)

H-Arg-Ser-Ser-Cys-Phe-Gly-Gly-Arg-Ile-Asp-Arg-Ile-Gly-Ala-Gln-Ser-[D-Ala]-Leu-Gly-Cys-Asn-Ser-Phe-Arg-OH

Ex. III.A.65: [D-Ala¹⁴²]rANVP(126—149)—NH₂

H-Arg-Ser-Ser-Cys-Phe-Gly-Gly-Arg-Ile-Asp-Arg-Ile-Gly-Ala-Gln-Ser-[D-Ala]-Leu-Gly-Cys-Asn-Ser-Phe-Arg-NH₂

Ex. III.A.66: [D-Ala¹⁴²]rANVP(126—148)—NH₂

H-Arg-Ser-Ser-Cys-Phe-Gly-Gly-Arg-Ile-Asp-Arg-Ile-Gly-Ala-gln-Ser-[D-Ala]-Leu-Gly-Cys-Asn-Ser-Phe-NH₂

Ex. III.A.67: [D-Ala¹⁴²]rANVP(126—145)—NH₂

H-Arg-Ser-Ser-Cys-Phe-Gly-Gly-Arg-Ile-Asp-Arg-Ile-Gly-Ala-Gln-Ser-[D-Ala]-Leu-Gly-Cys-NH₂

Ex. III.A.68: [D-Ala¹⁴³⁷]rANVP(127-151)

H-Arg-Ser-Ser-Cys-Phe-Gly-Gly-Arg-Met-Asp-Arg-Ile-Gly-Ala-Gln-Ser-[D-Ala]-Leu-Gly-Cys-Asn-Ser-Phe-Arg-tyr-OH Ex. III.A.69 : [D-Ala¹⁴³]rANVP(127—151)—NH₂

H-Arg-Ser-Ser-Cys-Phe-Gly-Gly-Arg-Met-Asp-Arg-Ile-Gly-Ala-Gln-Ser-[D-Ala]-Leu-Gly-Cys-Asn-Ser-Phe-Arg-Tyr-NH₂

Ex. III.A.70: [D-Ala¹⁴³]rANVP(127-150)

H-Arg-Ser-Ser-Cys-Phe-Gly-Gly-Arg-Met-Asp-Arg-Ile-Gly-Ala-Gln-Ser-[D-Ala]-Leu-Gly-Cys-Asn-Ser-Phe-Arg-OH

Ex. III.A.71: [D-Ala¹⁴³]rANVP(127—150)—NH₂

H-Arg-Ser-Ser-Cys-Phe-Gly-Gly-Arg-Met-Asp-Arg-Ile-Gly-Ala-Gln-Ser-[D-Ala]-Leu-Gly-Cys-Asn-Ser-Phe-Arg-NH₂

Ex. III.A.72: [D-Ala¹⁴³]rANVP(127-149)-NH₂

H-Arg-Ser-Ser-Cys-Phe-Gly-Gly-Arg-Met-Asp-Arg-Ile-Gly-Ala-Gln-Ser-[D-Ala]Leu-Gly-Cys-NH₂

Ex. III.A.73: [D-Ala¹⁴³]rANVP(127—146)—NH₂

H-Arg-Ser-Ser-Cys-Phe-Gly-Gly-Arg-Met-Asp-Arg-Ile-Gly-Ala-Gln-Ser-[D-Ala]-Leu-Gly-Cys-NH₂

* Ex. III.A.74: [D-Leu¹⁴³]rANVP(126-150)

H-Arg-Ser-Ser-Cys-Phe-Gly-Gly-Arg-Met-Asp-Arg-Ile-Gly-Ala-Gln-Ser-Gly-[D-Leu]-Gly-Cys-Asn-Ser-Phe-Arg-Tyr-OH

* Ex. III.A.75: [D-Ala¹⁴⁴]rANVP(126-150)

H-Arg-Ser-Ser-Cys-Phe-Gly-Gly-Arg-Ile-Asp-Arg-Ile-Gly-Ala-Gln-Ser-Gly-Leu-[D-Ala]-Cys-Asn-Ser-Phe-Arg-Tyr-OH

Ex. III.A.76: [D-Ala¹⁴⁴]rANVP(126—150)—NH₂

H-Arg-Ser-Ser-Cys-Phe-Gly-Gly-Arg-Ile-Asp-Arg-Ile-Gly-Ala-Gln-Ser-Gly-Leu-[D-Ala]-Cys-Asn-Ser-Phe-Arg-Tyr-NH₂

Ex. III.A.77: [D-Ala¹⁴⁴]rANVP(126-149)

H-Arg-Ser-Ser-Cys-Phe-Gly-Gly-Arg-Ile-Asp-Arg-Ile-Gly-Ala-Gln-Ser-Gly-Leu-[D-Ala]-Cys-Asn-Ser-Phe-Arg-OH

Ex. III.A.78: [D-Ala¹⁴⁴]rANVP(126—149)—NH₂

H-Arg-Ser-Ser-Cys-Phe-Gly-Gly-Arg-Ile-Asp-Arg-Ile-Gly-Ala-gln-Ser-Gly-Leu-[D-Ala]-Cys-Asn-Ser-Phe-Arg-NH₂

Ex. III.A.79: [D-Ala¹⁴⁴]rANVP(126—148)—NH₂

H-Arg-Ser-Ser-Cys-Phe-Gly-Gly-Arg-Ile-Asp-Arg-Ile-Gly-Ala-Gln-Ser-Gly-Leu-[D-Ala]-Cys-Asn-Ser-Phe-NH₂

Ex. III.A.80: [D-Ala¹⁴⁴]rANVP(126—145)—NH₂

H-Arg-Ser-Ser-Cys-Phe-Gly-Gly-Arg-Ile-Asp-Arg-Ile-Gly-Ala-Gln-Ser-Gly-Leu-[D-Ala]-Cys-NH₂

Ex. III.A.81: [D-Ala¹³⁷]rANVP(127-151)

H-Arg-Ser-Ser-Cys-Phe-Gly-Gly-Arg-Met-Asp-Arg-Ile-Gly-Ala-Gln-Ser-Gly-Leu-[D-Ala]-Cys-Asn-Ser-Phe-Arg-Tyr-OH

Ex. III.A.82: [D-Ala¹⁴⁵]rANVP(127—151)—NH₂

H-Arg-Ser-Ser-Cys-Phe-Gly-Gly-Arg-Met-Asp-Arg-Ile-Gly-Ala-gln-Ser-Gly-Leu-[D-Ala]-Cys-Asn-Ser-Phe-Arg-Tyr-NH₂

Ex. III.A.83: [D-Ala¹⁴⁵]rANVP(127-150)

H-Arg-Ser-Ser-Cys-Phe-Gly-Gly-Arg-Met-Asp-Arg-Ile-Gly-Ala-Gln-Ser-Gly-Leu-[D-Ala]-Cys-Asn-Ser-Phe-Arg-OH

Ex. III.A.84: [D-Ala¹⁴⁵]rANVP(127—150)—NH₂

H-Arg-Ser-Ser-Cys-Phe-Gly-Gly-Arg-Met-Asp-Arg-Ile-Gly-Ala-Gln-Ser-Gly-Leu-[D-Ala]-Cys-Asn-Ser-Phe-Arg-NH₂

Ex. III.A.85: [D-Ala¹⁴⁵]rANVP(127—149)—NH₂

H-Arg-Ser-Ser-Cys-Phe-Gly-Gly-arg-Met-Asp-Arg-Ile-Gly-Ala-gln-Ser-Gly-Leu-[D-Ala]-Cys-Asn-Ser-Phe-NH₂

Ex. III.A.86: [D-Ala¹⁴⁵]rANVP(127—146)—NH₂

H-Arg-Ser-Ser-Cys-Phe-Gly-Gly-Arg-Met-Asp-Arg-
Ile-Gly-Ala-Gln-Ser-Gly-Leu-[D-Ala]-Cys-NH₂

* Ex. III.A.87: [D-Cys¹⁴⁵]rANVP(126-150)

H-Arg-Ser-Ser-Cys-Phe-Gly-Gly-Arg-Ile-Asp-Arg-
Ile-Gly-Ala-Gln-Ser-Gly-Leu-Gly-[D-Cys]-Asn-Ser-
Phe-Arg-Tyr-OH

Ex. III.A.88: [D-Cys¹⁴⁵]rANVP(126—150)—NH₂

H-Arg-Ser-Ser-Cys-Phe-Gly-Gly-Arg-Ile-Asp-Arg-
Ile-Gly-Ala-gln-Ser-Gly-Leu-Gly-[D-Cys]-Asn-Ser-
Phe-Arg-Tyr-NH₂

Ex. III.A.89: [D-Cys¹⁴⁵]rANVP(126-149)

H-Arg-Ser-Ser-Cys-Phe-Gly-Gly-Arg-Ile-Asp-Arg-
Ile-Gly-Ala-Gln-Ser-Gly-Leu-Gly-[D-Cys]-Asn-Ser-
Phe-Arg-OH

Ex. III.A.90: [D-Cys¹⁴⁵]rANVP(126-149)-NH₂

H-Arg-Ser-Ser-Cys-Phe-Gly-Gly-Arg-Ile-Asp-Arg-
Ile-Gly-Ala-gln-Ser-Gly-Leu-Gly-[D-Cys]-Asn-Ser-
Phe-Arg-NH₂

Ex. III.A.91: [D-Cys¹⁴⁵]rANVP(126—148)—NH₂

H-Arg-Ser-Ser-Cys-Phe-Gly-Gly-Arg-Ile-Asp-Arg-
Ile-Gly-Ala-Gln-Ser-Gly-Leu-Gly-[D-Cys]-Asn-Ser-
Phe-NH₂

Ex. III.A.92: [D-Cys¹⁴⁵]rANVP(126—145)—NH₂

H-Arg-Ser-Ser-Cys-Phe-Gly-Gly-Arg-Ile-Asp-Arg-
Ile-Gly-Ala-Gln-Ser-Gly-Leu-Gly-[D-Cys]-NH₂

Ex. III.A.93: [D-Cys¹⁴⁶]hANVP(127-151)

H-Arg-Ser-Ser-Cys-Phe-Gly-Gly-Arg-Met-Asp-Arg-
Ile-Gly-Ala-gln-Ser-Gly-Leu-Gly-[D-Cys]-Asn-Ser-
Phe-Arg-Tyr-OH Ex. III.A.94: [D-Cys¹⁴⁶]hANVP(127—151)—NH₂

H-Arg-Ser-Ser-Cys-Phe-Gly-Gly-Arg-Met-Asp-Arg-
Ile-Gly-Ala-gln-Ser-Gly-Leu-Gly-[D-Cys]-Asn-Ser-
Phe-Arg-Tyr-NH₂

Ex. III.A.95: [D-Cys¹⁴⁶]hANVP(127-150)

H-Arg-Ser-Ser-Cys-Phe-Gly-Gly-Arg-Met-Asp-Arg-
Ile-Gly-Ala-Gln-Ser-Gly-Leu-Gly-[D-Cys]-Asn-Ser-
Phe-Arg-OH

Ex. III.A.96: [D-Cys¹⁴⁶]hANVP(127—150)—NH₂

H-Arg-Ser-Ser-Cys-Phe-Gly-Gly-Arg-Met-Asp-Arg-
Ile-Gly-Ala-Gln-Ser-Gly-Leu-Gly-[D-Cys]-Asn-Ser-
Phe-Arg-NH₂

Ex. III.A.97: [D-Cys¹⁴⁶]hANVP(127—149)—NH₂

H-Arg-Ser-Ser-Cys-Phe-Gly-Gly-Arg-Met-Asp-Arg-
Ile-Gly-Ala-Gln-Ser-Gly-Leu-Gly-[D-Cys]-Asn-Ser-
Phe-NH₂

Ex. III.A.98: [D-Cys¹⁴⁶]hANVP(127—146)—NH₂

H-Arg-Ser-Ser-Cys-Phe-Gly-Gly-Arg-Met-Asp-Arg-
Ile-Gly-Ala-Gln-Ser-Gly-Leu-Gly-[D-Cys]-NH₂

Ex. III.A.99: [D-Asn¹⁴⁶]rANVP(126-150)

H-Arg-Ser-Ser-Cys-Phe-Gly-Gly-Arg-Ile-Asp-Arg-
Ile-Gly-Ala-gln-Ser-Gly-Leu-Gly-Cys-[D-Asn]-Ser-
Phe-Arg-Tyr-OH Ex. III.A.100: [D-Asn¹⁴⁷]rANVP(127-151)

H-Arg-Ser-Ser-Cys-Phe-Gly-Gly-Arg-Met-Asp-Arg-
Ile-Gly-Ala-gln-Ser-Gly-Leu-Gly-Cys-[D-Asn]-Ser-
Phe-Arg-Tyr-OH

* Ex. III.A.101: [D-Ser¹⁴⁷]rANVP(126-150)

H-Arg-Ser-Ser-Cys-Phe-Gly-Gly-Arg-Ile-Asp-Arg-
Ile-Gly-Ala-Gln-Ser-Gly-Leu-Gly-Cys-Asn-[D-Ser]-
Phe-Arg-Tyr-OH

Ex. III.A.102: [D-Ser¹⁴⁷]rANVP(126—150)—NH₂

H-Arg-Ser-Ser-Cys-Phe-Gly-Gly-Arg-Ile-Asp-Arg-
Ile-Gly-Ala-Gln-Ser-Gly-Leu-Gly-Cys-Asn-[D-Ser]-
Phe-Arg-tyr-NH₂

Ex. III.A.103: [D-Ser¹⁴⁷]rANVP(126-149)

H-Arg-Ser-Ser-Cys-Phe-Gly-Gly-Arg-Ile-Asp-Arg-
Ile-Gly-Ala-Gln-Ser-Gly-Leu-Gly-Cys-Asn-[D-Ser]-
Phe-Arg-OH

Ex. III.A.104: [D-Ser¹⁴⁷]rANVP(126—149)—NH₂

H-Arg-Ser-Ser-Cys-Phe-Gly-Gly-Arg-Ile-Asp-Arg-
Ile-Gly-Ala-Gln-Ser-Gly-Leu-Gly-Cys-Asn-[D-Ser]-
Phe-Arg-NH₂

Ex. III.A.105: [D-Ser¹⁴⁷]rANVP(126—148)—NH₂

H-Arg-Ser-Ser-Cys-Phe-Gly-Gly-Arg-Ile-Asp-Arg-
Ile-Gly-Ala-Gln-Ser-Gly-Leu-Gly-Cys-Asn-[D-Ser]-
Phe-NH₂

Ex. III.A.106: [D-Ser¹⁴⁸]hANVP(127-151)

H-Arg-Ser-Ser-Cys-Phe-Gly-Gly-Arg-Met-Asp-Arg-
Ile-Gly-Ala-gln-Ser-Gly-Leu-Gly-Cys-Asn-[D-Ser]-
Phe-Arg-Tyr-OH Ex. III.A.107: [D-Ser¹⁴⁸]rANVP(127—151)—NH₂

H-Arg-Ser-Ser-Cys-Phe-Gly-Gly-Arg-Met-Asp-Arg-
Ile-Gly-Ala-Gln-Ser-Gly-Leu-Gly-Cys-Asn-[D-Ser]-
Phe-Arg-Tyr-NH₂

Ex. III.A.108: [D-Ser¹⁴⁸]hANVP(127-150)

H-Arg-Ser-Ser-Cys-Phe-Gly-Gly-Arg-Met-Asp-Arg-
Ile-Gly-Ala-Gln-Ser-Gly-Leu-Gly-Cys-Asn-[D-Ser]-
Phe-Arg-OH

Ex. III.A.109: [D-Ser¹⁴⁸]hANVP(127—150)—NH₂

H-Arg-Ser-Ser-Cys-Phe-Gly-Gly-Arg-Met-Asp-Arg-
Ile-Gly-Ala-Gln-Ser-Gly-Leu-Gly-Cys-Asn-[D-Ser]-
Phe-Arg-NH₂

Ex. III.A.110: [D-Ser¹⁴⁸]hANVP(127—149)—NH₂

H-Arg-Ser-Ser-Cys-Phe-Gly-Gly-Arg-Met-Asp-Arg-
Ile-Gly-Ala-gln-Ser-Gly-Leu-Gly-Cys-Asn-[D-Ser]-
Phe-NH₂

Ex. III.A.111: [D-Phe¹⁴⁸]rANVP(126-150)

H-Arg-Ser-Ser-Cys-Phe-Gly-Gly-Arg-Ile-Asp-Arg-
Ile-Gly-Ala-Gln-Ser-Gly-Leu-Gly-Cys-Asn-Ser-[D-
Phe]-Arg-Tyr-OH

Ex. III.A.112: [D-Phe[149]]hANVP(127-151)

H-Arg-Ser-Ser-Cys-Phe-Gly-Gly-Arg-Met-Asp-Arg-Ile-Gly-Ala-Gln-Ser-Gly-Leu-Gly-Cys-Asn-Ser-[D-Phe]-Arg-Tyr-OH

Ex. III.A.113: [D-Arg[126]]rANVP(126-150)

H-[D-Arg]-Ser-Ser-Cys-Phe-Gly-Gly-Arg-Ile-Asp-Arg-Ile-Gly-Ala-gln-Ser-Gly-Leu-Gly-Cys-Asn-Ser-Phe-Arg-Tyr-OH Ex. III.A.114: [D-Arg[126]]rANVP(126—150)—NH$_2$ H-[D-Arg]-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-tyr-NH$_2$ Ex. III.A.115: [D-Arg[126]]rANVP(126-149)

H-[D-Arg]-Ser-Ser-Cys-Phe-Gly-Gly-Arg-Ile-Asp-Arg-Ile-Gly-Ala-gln-Ser-Gly-Leu-Gly-Cys-Asn-Ser-Phe-Arg-OH Ex. III.A.116: [D-Arg[126]]rANVP(126—149)—NH$_2$ H-[D-Arg]-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-NH$_2$ Ex. III.A.117: [D-Arg[126]]rANVP(126—148)—NH$_2$ H-[D-Arg]-Ser-Ser-Cys-Phe-Gly-Gly-Arg-Ile-Asp-Arg-Ile-Gly-Ala-Gln-Ser-Gly-Leu-Gly-Cys-Asn-Ser-Phe-NH$_2$ Ex. III.A.118: [D-Arg[126]]rANVP(126—145)—NH$_2$ H-[D-Arg]-Ser-Ser-Cys-Phe-Gly-Gly-Arg-Ile-Asp-Arg-Ile-Gly-Ala-Gln-Ser-Gly-Leu-Gly-Cys-NH$_2$ Ex. III.A.119: [D-Arg[127]]hANVP(127-151)

H-[D-Arg]-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH

Ex. III.A.120: [D-Arg[127]]hANVP(127—151)—NH$_2$

H-[D-Arg]-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr-NH$_2$

Ex. III.A.121: [D-Arg[127]]rANVP(127-150)

H-[D-Arg]-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-OH

Ex. III.A.122: [D-Arg[127]]hANVP(127—150)—NH$_2$

H-[D-Arg]-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-NH$_2$

Ex. III.A.123: [D-Arg[127]]hANVP(127—149)—NH$_2$

H-[D-Arg]-Ser-Ser-Cys-Phe-Gly-Gly-Arg-Met-Asp-Arg-Ile-Gly-Ala-Gln-Ser-Gly-Leu-Gly-Cys-Asn-Ser-Phe-NH$_2$

Ex. III.A.124: [D-Arg[127]]hANVP(127—146)—NH$_2$

H-[D-Arg]-Ser-Ser-Cys-Phe-Gly-Gly-Arg-Met-Asp-Arg-Ile-Gly-Ala-Gln-Ser-Gly-Leu-Gly-Cys-NH$_2$

Ex. III.A.125: [D-Ser[127]]rANVP(126-150)

H-Arg-[D-Ser]-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH

Ex. III.A.126: [D-Ser[128]]hANVP(127-151)

H-Arg-[D-Ser]-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH

Ex. III.A.127: [D-Ser[128]]rANVP(126-150)

H-Arg-Ser-[D-Ser]-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH

Ex. III.A.128: [D-Ser[129]]hANVP(127-151)

H-Arg-Ser-[D-Ser]-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH

Ex. III.A.129: [D-Ala[131]][D-Ala[142]]rANVP(126-150)

H-Arg-Ser-Ser-Cys-Phe-[D-Ala]Gly-Arg-Ile-Asp-Arg-Ile-Gly-Ala-Gln-Ser-[D-Ala]-Leu-Gly-Cys-Asn-Ser-Phe-Arg-Tyr-OH

Ex. III.A.130: [D-Ala[131]][D-Ala[142]]rANVP(126-150)—NH$_2$

H-Arg-Ser-Ser-Cys-Phe-[D-Ala]-Gly-Arg-Ile-Asp-Arg-ILe-Gly-Ala-Gln-ser-[D-Ala]-Leu-Gly-Cys-Asn-Ser-Phe-Arg-Tyr-NH$_2$ Ex. III.A.131: [D-Ala[131]][D-Ala[142]]rANVP(126-149)

H-Arg-Ser-Ser-Cys-Phe-[D-Ala]-Gly-Arg-Ile-Asp-Arg-Ile-Gly-Ala-Gln-Ser-[D-Ala]-Leu-Gly-Cys-Asn-Ser-Phe-Arg-OH

Ex. III.A.132: [D-Alal[131]][D-Ala[142]]rANVP(126—149)—NH$_2$

H-Arg-Ser-Ser-Cys-Phe-[D-Ala]Gly-Arg-Ile-Asp-Arg-Ile-Gly-Ala-gln-Ser-[D-Ala]-Leu-Gly-Cys-Asn-Ser-Phe-Arg-NH$_2$ Ex. III.A.133: [D-Ala[131]][D-Ala[142]]rANVP(126—148)—NH$_2$ H-Arg-Ser-Ser-CysPhe-[D-Ala]-Gly-Arg-Ile-Asp-Arg-Ile-Gly-Ala-Gln-Ser-[D-Ala]-Leu-Gly-Cys-Asn-Ser-Phe-NH$_2$ Ex. III.A.134: [D-Ala[131]][D-Ala[142]]rANVP(126—145)—NH$_2$ H-Arg-Ser-Ser-Cys-Phe-[D-Ala]-Gly-Arg-Ile-Asp-Arg-Ile-Gly-Ala-gln-Ser-[D-Ala]-Leu-Gly-Cys-NH$_2$ Ex. III.A.135: [D-Ala[132]][D-Ala[143]]hANVP(127-151)

H-Arg-Ser-Ser-Cys-Phe-[D-Ala]-Gly-Arg-Met-Asp-Arg-Ile-Gly-Ala-gln-Ser-[D-Ala]-Leu-Gly-Cys-Asn-Ser-Phe-Arg-Tyr-OH Ex. III.A.136: [D-Ala[132]][D-Ala[143]]hANVP(127—151)—NH$_2$ H-Arg-Ser-Ser-Cys-Phe-[D-Ala]-Gly-Arg-Met-Asp-Arg-Ile-Gly-Ala-Gln-Ser-[D-Ala]-Leu-Gly-Cys-Asn-Ser-Phe-Arg-Tyr-NH$_2$ Ex. III.A.137: [D-Ala¹³²][D-Ala¹⁴³]hANVP(127-150)

H-Arg-Ser-Ser-Cys-Phe-[D-Ala]-Gly-Arg-Met-Asp-
Arg-Ile-Gly-Ala-Gln-Ser-[D-Ala]-Leu-Gly-Cys-
Asn-Ser-Phe-Arg-OH

Ex. III.A.138:
[D-Ala¹³²][D-Ala¹⁴³]rANVP(127-150)—NH₂

H-Arg-Ser-Ser-Cys-Phe-[D-Ala]-Gly-Arg-Met-Asp-
Arg-Ile-Gly-Ala-Gln-Ser-[D-Ala]-Leu-Gly-Cys-
Asn-Ser-Phe-Arg-NH₂

Ex. III.A.139:
[D-Ala¹³²][D-Ala¹⁴³]hANVP(127-149)—NH₂

H-Arg-Ser-Ser-Cys-Phe-[D-Ala]-Gly-Arg-Met-Asp-
Arg-Ile-Gly-Ala-Gln-Ser-[D-Ala]-Leu-Gly-Cys-
Asn-Ser-Phe-NH₂

Ex. III.A.140:
[D-Ala¹³²][D-Ala¹⁴³]hANVP(127—146)—NH₂

H-Arg-Ser-Ser-Cys-Phe-[D-Ala]-Gly-Arg-Met-Asp-
Arg-Ile-Gly-Ala-Gln-Ser-[D-Ala]-Leu-Gly-Cys-
NH₂

Ex. III.A.141: [D-Ala¹³¹][D-Cys¹⁴⁵]rANVP(126-150)

H-Arg-Ser-Ser-Cys-Phe-[D-Ala)-Gly-Arg-Ile-Asp-
Arg-Ile-Gly-Ala-Gln-Ser-Gly-Leu-Gly-[D-Cys]-
Asn-Ser-Phe-Arg-Tyr-OH

Ex. III.A.142:
[D-Ala¹³¹][D-Cys¹⁴⁵]rANVP(126—150)—NH₂

H-Arg-Ser-Ser-Cys-Phe-[D-Ala]-Gly-Arg-Ile-Asp-
Arg-Ile-Gly-Ala-Gln-Ser-Gly-Leu-Gly-[D-Cys]-
Asn-Ser-Phe-Arg-Tyr-NH₂

Ex. III.A.143: [D-Ala¹³¹][D-Cys¹⁴⁵]rANVP(126-149)

H-Arg-Ser-Ser-Cys-Phe-[D-Ala]-Gly-Arg-Ile-Asp-
Arg-Ile-Gly-Ala-Gln-Ser-Gly-Leu-Gly-[D-Cys]-
Asn-Ser-Phe-Arg-OH

Ex. III.A.144:
[D-Ala¹³¹][D-Cys¹⁴⁸]rANVP(126—149)—NH₂

H-Arg-Ser-Ser-Cys-Phe-[D-Ala]-Gly-Arg-Ile-Asp-
Arg-Ile-Gly-Ala-gln-Ser-Gly-Leu-Gly-[D-Cys]-Asn-
Ser-Phe-Arg-NH₂

Ex. III.A.145:
[D-Ala¹³¹][D-Cys¹⁴⁵]rANVP(126—148)—NH₂

H-Arg-Ser-Ser-Cys-Phe-[D-Ala]-Gly-Arg-Ile-Asp-
Arg-Ile-Gly-Ala-Gln-Ser-Gly-Leu-Gly-[D-Cys]-
Asn-Ser-Phe-NH₂

Ex. III.A.146:
[D-Ala¹³¹][D-Cys¹⁴⁵]rANVP(126—145)—NH₂

H-Arg-Ser-Ser-Cys-Phe-[D-Ala]-Gly-Arg-Ile-Asp-
Arg-Ile-Gly-Ala-gln-Ser-Gly-Leu-Gly-[D-Cys]-NH₂

Ex. III.A.147: [D-Ala¹³²]hANVP(127-151)

H-Arg-Ser-Ser-Cys-Phe-[D-Ala]-Gly-Arg-Met-Asp-
Arg-Ile-Gly-Ala-gln-Ser-Gly-Leu-Gly-[D-Cys]-Asn-
Ser-Phe-Arg-Tyr-OH Ex. III.A.148:
[D-Ala¹³²][D-Cys¹⁴⁶]rANVP(127—151)—NH₂

H-Arg-Ser-Ser-Cys-Phe-[D-Ala]-Gly-Arg-Met-Asp-
Arg-Ile-Gly-Ala-Gln-Ser-Gly-Leu-Gly-[D-Cys]-
Asn-Ser-Phe-Arg-Tyr-NH₂

Ex. III.A.149: [D-Ala¹³²][D-Cys¹⁴⁶]hANVP(127-150)

H-Arg-Ser-Ser-Cys-Phe-[D-Ala]-Gly-Arg-Met-Asp-
Arg-Ile-Gly-Ala-Gln-Ser-Gly-Leu-Gly-[D-Cys]-
Asn-Ser-Phe-Arg-OH

Ex. III.A.150:
[D-Ala¹³²[[D-Cys¹⁴⁶]hANVP(126—150)—NH₂

H-Arg-Ser-Ser-Cys-Phe-[D-Ala]-Gly-Arg-Met-Asp-
Arg-Ile-Gly-Ala-Gln-Ser-Gly-Leu-Gly-[D-Cys]-
Asn-Ser-Phe-Arg-NH₂

Ex. III.A.151:
[D-Ala¹³²][D-Cys¹⁴⁶]hANVP(127—149)—NH₂

H-Arg-Ser-Ser-Cys-Phe-[D-Ala]-Gly-Arg-Met-Asp-
Arg-Ile-Gly-Ala-gln-Ser-Gly-Leu-Gly-[D-Cys]-Asn-
Ser-Phe-NH₂

Ex. III.A.152:
[D-Ala¹³²][D-Cys¹⁴⁶]hANVP(127—146)—NH₂

H-Arg-Ser-Ser-Cys-Phe-[D-Ala]Gly-Arg-Met-Asp-
Arg-Ile-Gly-Ala-Gln-Ser-Gly-Leu-Gly-[D-Cys]-
NH₂

Ex. III.A.153: [D-Cys¹²⁹][D-Ala¹³¹]rANVP(126-150)

H-Arg-Ser-Ser-[D-Cys]-Phe-[D-Ala]Gly-Arg-Ile-Asp-
Arg-Ile-Gly-Ala-gln-Ser-Gly-Leu-Gly-Cys-Asn-Ser-
Phe-Arg-Tyr-OH Ex. III.A.154:
[D-Cys¹²⁹][D-Ala¹³¹]rANVP(126—150)—NH₂

H-Arg-Ser-Ser-[D-Cys]-Phe-[D-Ala]-Gly-Arg-Ile-Asp-
Arg-Ile-Gly-Ala-Gln-Ser-Gly-Leu-Gly-Cys-Asn-
Ser-Phe-Arg-Tyr-NH₂

Ex. III.A.155: [D-Cys¹²⁹][D-Ala¹³¹]rANVP(126-149)

H-Arg-Ser-Ser-[D-Cys]-Phe-[D-Ala]-Gly-Arg-Ile-Asp-
Arg-Ile-Gly-Ala-gln-Ser-Gly-Leu-Gly-Cys-Asn-Ser-
Phe-Arg-OH Ex. III.A.156:
[D-Cys¹²⁹][D-Ala¹³¹]rANVP(126—149)—NH₂

H-Arg-Ser-Ser-[D-Cys]-Phe-[D-Ala]-Gly-Arg-Ile-Asp-
Arg-Ile-Gly-Ala-Gln-Ser-Gly-Leu-Gly-Cys-Asn-
Ser-Phe-Arg-NH₂

Ex. III.A.157:
[D-Cys¹²⁹][D-Ala¹³¹]rANVP(126—148)—NH₂

H-Arg-Ser-Ser-[D-Cys]-Phe-[D-Ala]-Gly-Arg-Ile-Asp-
Arg-Ile-Gly-Ala-gln-Ser-Gly-Leu-Gly-Cys-Asn-Ser-
Phe-NH₂

Ex. III.A.158:
[D-Cys¹²⁹][D-Ala¹³¹]rANVP(126—145)—NH₂

H-Arg-Ser-Ser-[D-Cys]-Phe-[D-Ala]-Gly-Arg-Ile-Asp-
Arg-Ile-Gly-Ala-Gln-Ser-Gly-Leu-Gly-Cys-NH₂

Ex. III.A.159: [D-Cys$^{130}$][D-Ala$^{132}$]hANVP(127-151)

H-Arg-Ser-Ser-[D-Cys]-Phe-[D-Ala]-Gly-Arg-Met-
Asp-Arg-Ile-Gly-Ala-Gln-Ser-Gly-Leu-Gly-Cys-
Asn-Ser-Phe-Arg-Tyr-OH

Ex. III.A.160:
[D-Cys$^{130}$][D-Ala$^{132}$]hANVP(127—151)—NH$_2$

H-Arg-Ser-Ser-[D-Cys]-Phe-[D-Ala]-Gly-Arg-Met-
Asp-Arg-Ile-Gly-Ala-Gln-Ser-Gly-Leu-Gly-Cys-
Asn-Ser-Phe-Arg-Tyr-NH$_2$

Ex. III.A.161: [D-Cys$^{130}$][D-Ala$^{132}$]hANVP(127-150)

H-Arg-Ser-Ser-[D-Cys]-Phe-[D-Ala]-Gly-Arg-Met-
Asp-Arg-Ile-Gly-Ala-Gln-Ser-Gly-Leu-Gly-Cys-
Asn-Ser-Phe-Arg-OH

Ex. III.A.162:
[D-Cys$^{130}$][D-Ala$^{132}$]hANVP(127—150)—NH$_2$

H-Arg-Ser-Ser-[D-Cys]-Phe-[D-Ala]-Gly-Arg-Met-
Asp-Arg-Ile-Gly-Ala-Gln-Ser-Gly-Leu-Gly-Cys-
Asn-Ser-Phe-Arg-NH$_2$

Ex. III.A.163:
[D-Cys$^{130}$][D-Ala$^{132}$]hANVP(127—149)—NH$_2$

H-Arg-Ser-Ser-[D-Cys]-Phe-[D-Ala]-Gly-Arg-Met-
Asp-Arg-Ile-Gly-Ala-Gln-Ser-Gly-Leu-Gly-Cys-
Asn-Ser-Phe-NH$_2$

Ex. III.A.164:
[D-Cys$^{130}$][D-Ala$^{132}$hANVP(127—146)—NH$_2$

H-Arg-Ser-Ser-[D-Cys]-Phe-[D-Ala]-Gly-Arg-Met-
Asp-Arg-Ile-Gly-Ala-Gln-Ser-Gly-Leu-Gly-Cys-
NH$_2$

Ex. III.A.165: [D-Ala$^{131}$][D-Ser$^{147}$]rANVP(126-150)

H-Arg-Ser-Ser-Cys-Phe-Gly-[D-Ala]-Gly-Arg-Ile-
Asp-Arg-Ile-Gly-Ala-gln-Ser-Gly-Leu-Gly-Cys-
Asn-[D-Ser]-Phe-Arg-Tyr-OH Ex. III.A.166:
[D-Ala$^{131}$][D-Ser$^{147}$]rANVP(126—150)—NH$_2$ H-Arg-Ser-Ser-Cys-Phe-[D-Ala]Gly-Arg-Ile-Asp-Arg-
Ile-Gly-Ala-gln-Ser-Gly-Leu-Gly-Cys-Asn-[D-Ser]-
Phe-Arg-Tyr-NH$_2$ Ex. III.A.167: [D-Ala$^{131}$][D-Ser$^{147}$]rANVP(126-149)

H-Arg-Ser-Ser-Cys-Phe-[D-Ala]-Gly-Arg-Ile-Asp-
Arg-Ile-Gly-Ala-Gln-Ser-Gly-Leu-Gly-Cys-Asn-[D-
Ser]-Phe-Arg-OH

Ex. III.A.168:
[D-Ala$^{131}$[D-Ser$^{147}$]rANVP(126—149)—NH$_2$

H-Arg-Ser-Ser-Cys-Phe-[D-Ala]-Gly-Arg-Ile-Asp-
Arg-Ile-Gly-Ala-Gln-Ser-Gly-Leu-Gly-Cys-Asn-[D-
Ser]-Phe-Arg-NH$_2$

Ex. III.A.169:
[D-Ala$^{131}$][D-Ser$^{147}$]rANVP(126—148)—NH$_2$

H-Arg-Ser-Ser-Cys-Phe-[D-Ala]-Gly-Arg-Ile-Asp-
Arg-Ile-Gly-Ala-GLn-Ser-Gly-Leu-Gly-Cys-Asn-
[D-Ser]-Phe-NH$_2$

Ex. III.A.170: [D-Ala$^{132}$][D-Ser$^{148}$]hANVP(127-151)

H-Arg-Ser-Ser-Cys-Phe-[D-Ala]-Gly-Arg-Met-Asp-
Arg-Ile-Gly-Ala-gln-Ser-Gly-Leu-Gly-Cys-Asn-[D-
Ser]-Phe-Arg-Tyr-OH Ex. III.A.171:
[D-Ala$^{132}$][D-Ser$^{148}$]hANVP(127-151)—NH$_2$ H-Arg-Ser-Ser-Cys-Phe-[D-Ala]-Gly-Arg-Met-Asp-
Arg-Ile-Gly-Ala-Gln-Ser-Gly-Leu-Gly-Cys-Asn-[D-
Ser]-Phe-Arg-Tyr-NH$_2$ Ex. III.A.172: [D-Ala$^{132}$][D-Ser$^{148}$]hANVP(127-150)

H-Arg-Ser-Ser-Cys-Phe-[D-Ala]-Gly-Arg-Met-Asp-
Arg-Ile-Gly-Ala-Gln-Ser-Gly-Leu-Gly-Cys-Asn-[D-
Ser]-Phe-Arg-OH

Ex. III.A.173:
[D-Ala$^{132}$][D-Ser$^{148}$]hANVP(127-150)—NH$_2$

H-Arg-Ser-Ser-Cys-Phe-[D-Ala]-Gly-Arg-Met-Asp-
Arg-Ile-Gly-Ala-Gln-Ser-Gly-Leu-Gly-Cys-Asn-[D-
Ser]-Phe-NH$_2$

Ex. III.A.174:
[D-Ala$^{132}$][D-Ser$^{148}$]hANVP(127—149)—NH$_2$

H-Arg-Ser-Ser-Cys-Phe-[D-Ala]-Gly-Arg-Met-Asp-
Arg-Ile-Gly-Ala-Gln-Ser-Gly-Leu-Gly-Cys-Asn-[D-
Ser]-Phe-NH$_2$

* Ex. III.A.175: [D-Asn$^{135}$]rANVP(126-150)

H-Arg-Ser-Ser-Cys-Phe-Gly-Gly-Arg-Ile-Asn-Arg-
Ile-Gly-Ala-Gln-Ser-Gly-Leu-Gly-Cys-Asn-Ser-
Phe-Arg-Tyr-OH

Ex. III.A.176: [Asn$^{135}$]rANVP(126—150)—NH$_2$

H-Arg-Ser-Ser-Cys-Phe-Gly-Gly-Arg-Ile-Asn-Arg-
Ile-Gly-Ala-Gln-Ser-Gly-Leu-Gly-Cys-Asn-Ser-
Phe-Arg-Tyr-NH$_2$

Ex. III.A.177: [Asn$^{135}$]rANVP(126-149)

H-Arg-Ser-Ser-Cys-Phe-Gly-Gly-Arg-Ile-Asn-Arg-
Ile-Gly-Ala-Gln-Ser-Gly-Leu-Gly-Cys-Asn-Ser-
Phe-Arg-OH

Ex. III.A.178: [Asn$^{135}$rANVP(126—149)—NH$_2$

H-Arg-Ser-Ser-Cys-Phe-Gly-Gly-Arg-Ile-Asn-Arg-
Ile-Gly-Ala-Gln-Ser-Gly-Leu-Gly-Cys-Asn-Ser-
Phe-Arg-NH$_2$

Ex. III.A.179: [Asn$^{135}$]rANVP(126—148)—NH$_2$

H-Arg-Ser-Ser-Cys-Phe-Gly-Gly-Arg-Ile-Asn-Arg-
Ile-Gly-Ala-Gln-Ser-Gly-Leu-Gly-Cys-Asn-Ser-
Phe-NH$_2$

Ex. III.A.180: [Asn$^{135}$]rANVP(126—150)—NH$_2$

H-Arg-Ser-Ser-Cys-Phe-Gly-Gly-Arg-Ile-Asn-Arg-
Ile-Gly-Ala-Gln-Ser-Gly-Leu-Gly-Cys-NH$_2$

Ex. III.A.181: [Asn$^{136}$]hANVP(127-151)

H-Arg-Ser-Ser-Cys-Phe-Gly-Gly-Arg-Met-Asn-Arg-
Ile-Gly-Ala-Gln-Ser-Gly-Leu-Gly-Cys-Asn-Ser-
Phe-Arg-Tyr-OH

Ex. III.A.182: [Asn¹³⁶]hANVP(127—150)—NH₂

H-Arg-Ser-Ser-Cys-Phe-Gly-Gly-Arg-Met-Asn-Arg-
Ile-Gly-Ala-Gln-Ser-Gly-Leu-Gly-Cys-Asn-Ser-
Phe-Arg-Tyr-NH₂

Ex. III.A.183: [Asn¹³⁶]hANVP(127-150)

H-Arg-Ser-Ser-Cys-Phe-Gly-Gly-Arg-Met-Asn-Arg-
Ile-Gly-Ala-Gln-Ser-Gly-Leu-Gly-Cys-Asn-Ser-
Phe-Arg-OH

Ex. III.A.184: [Asn¹³⁶]hANVP(127—150)—NH₂

H-Arg-Ser-Ser-Cys-Phe-Gly-Gly-Arg-Met-Asn-Arg-
Ile-Gly-Ala-Gln-Ser-Gly-Leu-Gly-Cys-Asn-Ser-
Phe-Arg-NH₂

Ex. III.A.185: [Asn¹³⁶]hANVP(127—149)—NH₂

H-Arg-Ser-Ser-Cys-Phe-Gly-Gly-Arg-Met-Asn-Arg-
Ile-Gly-Ala-Gln-Ser-Gly-Leu-Gly-Cys-Asn-Ser-
Phe-NH₂

Ex. III.A.186: [Asn¹³⁶]hANVP(127—146)—NH₂

H-Arg-Ser-Ser-Cys-Phe-Gly-Gly-Arg-Met-Asn-Arg-
Ile-Gly-Ala-Gln-Ser-Gly-Leu-Gly-Cys-NH₂

* Ex. III.A.187: [Phe¹³⁴]rANVP(126-150) or
[Phe¹³⁵]hANVP(127-151)

H-Arg-Ser-Ser-Cys-Phe-Gly-Gly-Arg-Phe-Asp-Arg-
Ile-Gly-Ala-Gln-Ser-Gly-Leu-Gly-Cys-Asn-Ser-
Phe-Arg-Tyr-OH

Ex. III.A.188: [Phe¹³⁴]rANVP(126—150)—NH₂ or
[Phe¹³⁵]hANVP(127—151)—NH₂

H-Arg-Ser-Ser-Cys-Phe-Gly-Gly-Arg-Phe-Asp-Arg-
Ile-Gly-Ala-Gln-Ser-Gly-Leu-Gly-Cys-Asn-Ser-
Phe-Arg-Tyr-NH₂

Ex. III.A.189: [Phe¹³⁴]rANVP(126-149) or
[Phe¹³⁵]hANVP(127-150)

H-Arg-Ser-Ser-Cys-Phe-Gly-Gly-Arg-Phe-Asp-Arg-
Ile-Gly-Ala-Gln-Ser-Gly-Leu-Gly-Cys-Asn-Ser-
Phe-Arg-OH

Ex. III.A.190: [Phe¹³⁴]rANVP(126—149)—NH₂ or
[Phe¹³⁵]hANVP(127—150)—NH₂

H-Arg-Ser-Ser-Cys-Phe-Gly-Gly-Arg-Phe-Asp-Arg-
Ile-Gly-Ala-Gln-Ser-Gly-Leu-Gly-Cys-Asn-Ser-
Phe-Arg-NH₂

Ex. III.A.191: [Phe¹³⁴rANVP(126—148)—NH₂ or
[Phe¹³⁵]hANVP(127—149)—NH₂

H-Arg-Ser-Ser-Cys-Phe-Gly-Gly-Arg-Phe-Asp-Arg-
Ile-Gly-Ala-Gln-Ser-Gly-Leu-Gly-Cys-Asn-Ser-
Phe-NH₂

Ex. III.A.192: [Phe¹³⁴]rANVP(126—145)—NH₂ or
[Phe¹³⁵]hANVP(127—146)—NH₂

H-Arg-Ser-Ser-Cys-Phe-Gly-Gly-Arg-Phe-Asp-Arg-
Ile-Gly-Ala-Gln-Ser-Gly-Leu-Gly-Cys-NH₂

Ex. III.A.193: [Pro¹³²]rANVP(126-150)

H-Arg-Ser-Ser-Cys-Phe-Gly-Pro-Arg-Ile-Asp-Arg-Ile-
Gly-Ala-GLn-Ser-Gly-Leu-Gly-Cys-Asn-Ser-Phe-
Arg-Tyr-OH

* Ex. III.A.194: [Pro¹³²]rANVP(126—150)—NH₂

H-Arg-Ser-Ser-Cys-Phe-Gly-Pro-Arg-Ile-Asp-Arg-Ile-
Gly-Ala-Gln-Ser-Gly-Leu-Gly-Cys-Asn-Ser-Phe-
Arg-Tyr-NH₂

Ex. III.A.195: [Pro¹³²]rANVP(126-149)

H-Arg-Ser-Ser-Cys-Phe-Gly-Pro-Arg-Ile-Asp-Arg-Ile-
Gly-Ala-gln-Ser-Gly-Leu-Gly-Cys-Asn-Ser-Phe-
Arg-OH Ex. III.A.196: [Pro¹³²]rANVP(126-149)—NH₂

H-Arg-Ser-Ser-Cys-Phe-Gly-Pro-Arg-Ile-Asp-Arg-Ile-
Gly-Ala-Gln-Ser-Gly-Leu-Gly-Cys-Asn-Ser-Phe-
Arg-NH₂

Ex. III.A.197: [Pro¹³²]rANVP(126—150)—NH₂

H-Arg-Ser-Ser-Cys-Phe-Gly-Pro-Arg-Ile-Asp-Arg-Ile-
Gly-Ala-Gln-Ser-Gly-Leu-Gly-Cys-Asn-Ser-Phe-
NH₂

Ex. III.A.198: [Pro¹³²]rANVP(126—145)—NH₂

H-Arg-Ser-Ser-Cys-Phe-Gly-Pro-Arg-Ile-Asp-Arg-Ile-
Gly-Ala-Gln-Ser-Gly-Leu-Gly-Cys-NH₂

* Ex. III.A.199: [Pro¹³⁵]hANVP(127-151)

H-Arg-Ser-Ser-Cys-Phe-Gly-Pro-Arg-Met-Asp-Arg-
Ile-Gly-Ala-gln-Ser-Gly-Leu-Gly-Cys-Asn-Ser-Phe-
Arg-Tyr-OH Ex. III.A.200: [Pro¹³³]hANVP(127—151)—NH₂

H-Arg-Ser-Ser-Cys-Phe-Gly-Pro-Arg-Met-Asp-Arg-
Ile-Gly-Ala-gln-Ser-Gly-Leu-Gly-Cys-Asn-Ser-Phe-
Arg-Tyr-NH₂

Ex. III.A.201: [Pro¹³³]hANVP(127-150)

H-Arg-Ser-Ser-Cys-Phe-Gly-Pro-Arg-Met-Asp-Arg-
Ile-Gly-Ala-Gln-Ser-Gly-Leu-Gly-Cys-Asn-Ser-
Phe-Arg-OH

Ex. III.A.202: [Pro¹³³]hANVP(127—150)—NH₂

H-Arg-Ser-Ser-Cys-Phe-Gly-Pro-Arg-Met-Asp-Arg-
Ile-Gly-Ala-Gln-Ser-Gly-Leu-Gly-Cys-Asn-Ser-
Phe-Arg-NH₂

Ex. III.A.203: [Pro¹³³]hANVP(127—149)—NH₂

H-Arg-Ser-Ser-Cys-Phe-Gly-Pro-Arg-Met-Asp-Arg-
Ile-Gly-Ala-Gln-Ser-Gly-Leu-Gly-Cys-Asn-Ser-
Phe-NH₂

Ex. III.A.204: [Pro¹³³]hANVP(127—146)—NH₂

H-Arg-Ser-Ser-Cys-Phe-Gly-Pro-Arg-Met-Asp-Arg-
Ile-Gly-Ala-Gln-Ser-Gly-Leu-Gly-Cys-NH₂

* Ex. III.A.205: [Ala¹³²]rANVP(126-150)

H-Arg-Ser-Ser-Cys-Phe-Gly-Ala-Arg-Ile-Asp-Arg-Ile-
Gly-Ala-GLn-Ser-Gly-Leu-Gly-Cys-Asn-Ser-Phe-
Arg-Tyr-OH

Ex. III.A.206: [Ala¹³³]hANVP(127-151)

H-Arg-Ser-Ser-Cys-Phe-Gly-Ala-Arg-Met-Asp-Arg-
Ile-Gly-Ala-Gln-Ser-Gly-Leu-Gly-Cys-Asn-Ser-
Phe-Arg-Tyr-OH

Ex. III.A.207: [Ala$^{131}$]rANVP(126-150)

H-Arg-Ser-Ser-Cys-Phe-Ala-Gly-Arg-Ile-Asp-Arg-Ile-Gly-Ala-gln-Ser-Gly-Leu-Gly-Cys-Asn-Ser-Phe-Arg-Tyr-OH Ex. III.A.208: [AlaI$^{132}$]hANVP(127-151)

H-Arg-Ser-Ser-Cys-Phe-Ala-Gly-Arg-Met-Asp-Arg-Ile-Gly-Ala-Gln-Ser-Gly-Leu-Gly-Cys-Asn-Ser-Phe-Arg-Tyr-OH

Ex. III.A.209: [Arg$^{128}$]rANVP(129-150)

H-Arg-Cys-Phe-Gly-Gly-Arg-Ile-Asp-Arg-Ile-Gly-Ala-GLn-Ser-Gly-Leu-Gly-Cys-Asn-Ser-Phe-Arg-Tyr-OH

Ex. III.A.210: [Arg$^{128}$]rANVP(129-149)

H-Arg-Cys-Phe-Gly-Gly-Arg-Ile-Asp-Arg-Ile-Gly-Ala-Gln-Ser-Gly-Leu-Gly-Cys-Asn-Ser-Phe-Arg-OH

Ex. III.A.211: [Arg$^{139}$]rANVP(130-151)

H-Arg-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH

Ex. III.A.212: [Arg$^{128}$]rANVP(129—148)—NH$_2$

H-Arg-Cys-Phe-Gly-Gly-Arg-Ile-Asp-Arg-Ile-Gly-Ala-gln-Ser-Gly-Leu-Gly-Cys-Asn-Ser-Phe-NH$_2$ Ex. III.A.213: [Arg$^{129}$]hANVP(130-146)

H-Arg-Cys-Phe-Gly-Gly-Arg-Met-Asp-Arg-Ile-Gly-Ala-Gln-Ser-Gly-Leu-Gly-Cys-OH

Ex. III.A.214: [Arg$^{129}$]hANVP(130—151)—NH$_2$

H-Arg-Cys-Phe-Gly-Gly-Arg-Met-Asp-Arg-Ile-Gly-Ala-Gln-Ser-Gly-Leu-Gly-Cys-Asn-Ser-Phe-Arg-Tyr-NH$_2$

Ex. III.A.215: [Arg$^{129}$]hANVP(130-150)

H-Arg-Cys-Phe-Gly-Gly-Arg-Met-Asp-Arg-Ile-Gly-Ala-Gln-Ser-Gly-Leu-Gly-Cys-Asn-Ser-Phe-Arg-OH

Ex. III.A.216: [Arg$^{129}$]hANVP(130—150)—NH$_2$

H-Arg-Cys-Phe-Gly-Gly-Arg-Met-Asp-Arg-Ile-Gly-Ala-Gln-Ser-Gly-Ala-Gln-Ser-Gly-Leu-Gly-Cys-Asn-Ser-Phe-Arg-NH$_2$

Ex. III.A.217: [Arg$^{128}$]rANVP(129—150)—NH$_2$

H-Arg-Cys-Phe-Gly-Gly-Arg-Ile-Asp-Arg-Ile-Gly-Ala-Gln-Ser-Gly-Leu-Gly-Cys-Asn-Ser-Phe-Arg-Tyr-NH$_2$

Ex. III.A.218: [Arg$^{128}$]rANVP(129—145)—NH$_2$

H-Arg-Cys-Phe-Gly-Gly-Arg-Met-Asp-Arg-Ile-Gly-Ala-Gln-Ser-Gly-Leu-Gly-Cys-NH$_2$

Ex. III.A.219: [Arg$^{128}$]rANVP(129-145)

H-Arg-Cys-Phe-Gly-Gly-Arg-Ile-Asp-Arg-Ile-Gly-Ala-Gln-Ser-Gly-Leu-Gly-Cys-OH

Ex. III.A.220: [Arg$^{129}$]hANVP(130-149)

H-Arg-Cys-Phe-Gly-Gly-Arg-Met-Asp-Arg-Ile-Gly-Ala-Gln-Ser-Gly-Leu-Gly-Cys-Asn-Ser-Phe-Arg-OH

Ex. III.A.221: [Arg$^{129}$]hANVP(130—149)—NH$_2$

H-Arg-Cys-Phe-Gly-Gly-Arg-Met-Asp-Arg-Ile-Gly-Ala-Gln-Ser-Gly-Leu-Gly-Cys-Asn-Ser-Phe-NH$_2$

Ex. III.A.222: [Arg$^{129}$]hANVP(130-146)

H-Arg-Cys-Phe-Gly-Gly-Arg-Met-Asp-Arg-Ile-Gly-Ala-Gln-Ser-Gly-Leu-Gly-Cys-OH

Ex. III.A.223: [Arg$^{129}$]hANVP(130—146)—NH$_2$

H-Arg-Cys-Phe-Gly-Gly-Arg-Met-Asp-Arg-Ile-Gly-Ala-Gln-Ser-Gly-Leu-Gly-Cys-NH$_2$

Ex. III.A.224: [Arg$^{128}$][D-Cys$^{129}$]rANVP(129-150)

H-Arg-[D-Cys]-Phe-Gly-Gly-Arg-Ile-Asp-Arg-Ile-Gly-Ala-Gln-Ser-Gly-Leu-Gly-Cys-Asn-Ser-Phe-Arg-Tyr-OH

Ex. III.A.225: [Arg$^{128}$][D-Cys$^{129}$]rANVP(129—148)—NH$_2$

H-Arg-[D-Cys]-Phe-Gly-Gly-Arg-Ile-Asp-Arg-Ile-Gly-Ala-Gln-Ser-Gly-Leu-Gly-Cys-Asn-Ser-Phe-NH$_2$

Ex. III.A.226: [Arg$^{128}$][D-Cys$^{129}$]rANVP(129—150)—NH$_2$

H-Arg-[D-Cys]-Phe-Gly-Gly-Arg-Met-Asp-Arg-Ile-Gly-Ala-Gln-Ser-Gly-Leu-Gly-Cys-Asn-Ser-Phe-Arg-Tyr-NH$_2$

Ex. III.A.227: [Arg$^{129}$][D-Cys$^{130}$]hANVP(130-151)

H-Arg-[D-Cys]-Phe-Gly-Gly-Arg-Met-Asp-Arg-Ile-Gly-Ala-Gln-Ser-Gly-Leu-Gly-Cys-Asn-Ser-Phe-Arg-Tyr-OH

Ex. III.A.228: [Arg$^{129}$][D-Cys$^{130}$]hANVP(130—149)—NH$_2$

H-Arg-[D-Cys]-Phe-Gly-Gly-Arg-Met-Asp-Arg-Ile-Gly-Ala-Gln-Ser-Gly-Leu-Gly-Cys-Asn-Ser-Phe-NH$_2$

Ex. III.A.229: [Arg$^{129}$][D-Cys$^{130}$]hANVP(130—146)—NH$_2$

H-Arg-[D-Cys]-Phe-Gly-Gly-Arg-Met-Asp-Arg-Ile-Gly-Ala-Gln-Ser-Gly-Leu-Gly-Cys-NH$_2$

Ex. III.A.230: [Arg$^{128}$][D-Phe$^{130}$]rANVP(129-150)

H-Arg-Cys-[D-Phe]-Gly-Gly-Arg-Ile-Asp-Arg-Ile-Gly-Ala-gln-Ser-Gly-Leu-Gly-Cys-Asn-Ser-Phe-Arg-Tyr-OH Ex. III.A.231: [Arg$^{128}$][D-Ala$^{131}$]rANVP(129-150)

H-Arg-Cys-Phe-[D-Ala]-Gly-Arg-Ile-Asp-Arg-Ile-Gly-Ala-Gln-Ser-Gly-Leu-Gly-Cys-Asn-Ser-Phe-Arg-Tyr-OH

Ex. III.A.232: [Arg$^{128}$][D-Ala$^{131}$]rANVP(129—148)—NH$_2$

H-Arg-Cys-Phe-[D-Ala]-Gly-Arg-Ile-Asp-Arg-Ile-Gly-Ala-Gln-Ser-Gly-Leu-Gly-Cys-Asn-Ser-Phe-NH$_2$

Ex. III.A.233: [Arg$^{128}$][D-Ala$^{131}$]rANVP(129—145)—NH$_2$

H-Arg-Cys-Phe-[D-Ala]-Gly-Arg-Ile-Asp-Arg-Ile-Gly-Ala-Gln-Ser-Gly-Leu-Gly-Cys-NH$_2$

Ex. III.A.234: [Arg¹³⁹][D-Ala¹³²]hANVP(130-151)

H-Arg-Cys-Phe-[D-Ala]-Gly-Arg-Met-Asp-Arg-Ile-
Gly-Ala-Gln-Ser-Gly-Leu-Gly-Cys-Asn-Ser-Phe-
Arg-Tyr-OH

Ex. III.A.235:
[Arg¹²⁹][D-Ala¹³²]hANVP(130—149)—NH₂

H-Arg-Cys-Phe-[D-Ala]-Gly-Arg-Met-Asp-Arg-Ile-
Gly-Ala-Gln-Ser-Gly-Leu-Gly-Cys-Asn-Ser-Phe-
NH₂

Ex. III.A.236:
[Arg¹²⁹][D-Ala¹³²]hANVP(130—146)—NH₂

H-Arg-Cys-Phe-[D-Ala]-Gly-Arg-Met-Asp-Arg-Ile-
Gly-Ala-Gln-Ser-Gly-Leu-Gly-Cys-NH₂

Ex. III.A.237: [Arg¹²⁸][D-Ala¹³²]rANVP(129-150)

H-Arg-Cys-Phe-Gly-[D-Ala]-Arg-Ile-Asp-Arg-Ile-
Gly-Ala-Gln-Ser-Gly-Leu-Gly-Cys-Asn-Ser-Phe-
Arg-Tyr-OH

Ex. III.A.238:
[Arg¹²⁸][D-Ala¹³²]rANVP(129—148)—NH₂

H-Arg-Cys-Phe-Gly-[D-Ala]-Arg-Ile-Asp-Arg-Ile-
Gly-Ala-Gln-Ser-Gly-Leu-Gly-Cys-Asn-Ser-Phe-
NH₂

Ex. III.A.239:
[Arg¹²⁸][D-Ala¹³²]rANVP(129—145)—NH₂

H-Arg-Cys-Phe-Gly-[D-Ala]-Arg-Ile-Asp-Arg-Ile-
Gly-Ala-Gln-Ser-Gly-Leu-Gly-Cys-NH₂

Ex. III.A.240: [Arg¹²⁹][D-Ala¹³³]hANVP(130-151)

H-Arg-Cys-Phe-Gly-[D-Ala]-Arg-Met-Asp-Arg-Ile-
Gly-Ala-Gln-Ser-Gly-Leu-Gly-Cys-Asn-Ser-Phe-
Arg-Tyr-OH

Ex. III.A.241:
[Arg¹²⁹][D-Ala¹³³]hANVP(130—149)—NH₂

H-Arg-Cys-Phe-Gly-[D-Ala]-Arg-Met-Asp-Arg-Ile-
Gly-Ala-Gln-Ser-Gly-Leu-Gly-Cys-Asn-Ser-Phe-
NH₂

Ex. III.A.242:
[Arg¹²⁹][D-Ala¹³³]hANVP(130—146)—NH₂

H-Arg-Cys-Phe-Gly-[D-Ala]-Arg-Met-Asp-Arg-Ile-
Gly-Ala-Gln-Ser-Gly-Leu-Gly-Cys-NH₂

Ex. III.A.243: [Arg¹²⁸][D-Ala¹⁴²]rANVP(129-150)

H-Arg-Cys-Phe-Gly-Gly-Arg-Ile-Asp-Arg-Ile-Gly-
Ala-Gln-Ser-[D-Ala]-Leu-Gly-Cys-Asn-Ser-Phe-
Arg-Tyr-OH

Ex. III.A.244:
[Arg¹²⁸][D-Ala¹⁴²]rANVP(129—148)—NH₂

H-Arg-Cys-Phe-Gly-Gly-Arg-Ile-Asp-Arg-Ile-Gly-
Ala-Gln-Ser-[D-Ala]-Leu-Gly-Cys-Asn-Ser-Phe-
NH₂

Ex. III.A.245:
[Arg¹²⁸][D-Ala¹⁴²]rANVP(129—145)—NH₂

H-Arg-Cys-Phe-Gly-Gly-Arg-Ile-
-Asp-Arg-Ile-Gly-Ala-Gln-Ser-[D-Ala]-Leu-Gly-
Cys-NH₂

Ex. III.A.246: [Arg¹²⁹][D-Ala¹⁴³]hANVP(130-151)

H-Arg-Cys-Phe-Gly-Gly-Arg-Met-Asp-Arg-Ile-Gly-
Ala-Gln-Ser-[D-Ala]-Leu-Gly-Cys-Asn-Ser-Phe-
Arg-Tyr-OH

Ex. III.A.247:
[Arg¹²⁹][D-Ala¹⁴³]hANVP(130—149)—NH₂

H-Arg-Cys-Phe-Gly-Gly-Arg-Met-Asp-Arg-Ile-Gly-
Ala-Gln-Ser-[D-Ala]-Leu-Gly-Cys-Asn-Ser-Phe-
NH₂

Ex. III.A.248:
[Arg¹²⁹][D-Ala¹⁴³]hANVP(130—146)—NH₂

H-Arg-Cys-Phe-Gly-Gly-Arg-Met-Asp-Arg-Ile-Gly-
Ala-Gln-Ser-[D-Ala]-Leu-Gly-Cys-NH₂

Ex. III.A.249: [Arg¹²⁸][D-Ala¹⁴⁴]rANVP(129-150)

H-Arg-Cys-Phe-Gly-Gly-Arg-Ile-Asp-Arg-Ile-Gly-
Ala-Gln-Ser-Gly-Leu-[D-Ala]-Cys-Asn-Ser-Phe-
Arg-Tyr-OH

Ex. III.A.250:
[Arg¹²⁸][D-Ala¹⁴⁴]rANVP(129—148)—NH₂

H-Arg-Cys-Phe-Gly-Gly-Arg-Ile-Asp-Arg-Ile-Gly-
Ala-Gln-Ser-Gly-Leu-[D-Ala]-Cys-Asn-Ser-Phe-
NH₂

Ex. III.A.251:
[Arg¹²⁸][D-Ala¹⁴⁴]rANVP(129—145)—NH₂

H-Arg-Cys-Phe-Gly-Gly-Arg-Ile-Asp-Arg-Ile-Gly-
Ala-Gln-Ser-Gly-Leu-[D-Ala]-Cys-NH₂

Ex. III.A.252: [Arg¹²⁹][D-Ala¹⁴⁵]hANVP(130-151)

H-Arg-Cys-Phe-Gly-Gly-Arg-Met-Asp-Arg-Ile-Gly-
Ala-Gln-Ser-Gly-Leu-[D-Ala]-Cys-Asn-Ser-Phe-
Arg-Tyr-OH

Ex. III.A.253:
[Arg¹²⁹][D-Ala¹⁴⁵]hANVP(130—149)—NH₂

H-Arg-Cys-Phe-Gly-Gly-Arg-Met-Asp-Arg-Ile-Gly-
Ala-Gln-Ser-Gly-Leu-[D-Ala]-Cys-Asn-Ser-Phe-
NH₂

Ex. III.A.254:
[Arg¹²⁹][D-Ala¹⁴⁵)hANVP(130—146)—NH₂

A-Arg-Cys-Phe-Gly-Gly-Arg-Met-Asp-Arg-Ile-Gly-
Ala-Gln-Ser-Gly-Leu-[D-Ala]-Cys-NH₂

Ex. III.A.255: [Arg¹²⁸][D-Cys¹⁴⁶]rANVP(129-150)

H-Arg-Cys-Phe-Gly-Gly-Arg-Ile-Asp-Arg-Ile-Gly-
Ala-Gln-Ser-Gly-Leu-Gly-[D-Cys]-Asn-Ser-Phe-
Arg-Tyr-OH

Ex. III.A.256:
[Arg¹²⁸][D-Cys¹⁴⁵]rANVP(129—148)—NH₂

H-Arg-Cys-Phe-Gly-Gly-Arg-Ile-Asp-Arg-Ile-Gly-
Ala-Gln-Ser-Gly-Leu-Gly-[D-Cys]-Asn-Ser-Phe-
NH₂

Ex. III.A.257:
[Arg¹²⁸][D-Cys¹⁴⁵]rANVP(129—145)—NH₂

H-Arg-Cys-Phe-Gly-Gly-Arg-Ile-Asp-Arg-Ile-Gly-
Ala-Gln-Ser-Gly-Leu-Gly-[D-Cys]-NH₂

Ex. III.A.258: [Arg$^{129}$][D-Cys$^{146}$]hANVP(130-151)

H-Arg-Cys-Phe-Gly-Gly-Arg-Met-Asp-Arg-Ile-Gly-Ala-Gln-Ser-Gly-Leu-Gly-[D-Cys]-Asn-Ser-Phe-Arg-Tyr-OH

Ex. III.A.259:
[Arg$^{129}$][D-Cys$^{146}$]hANVP(130—149)—NH$_2$

H-Arg-Cys-Phe-Gly-Gly-Arg-Met-Asp-Arg-Ile-Gly-Ala-Gln-Ser-Gly-Leu-Gly-[D-Cys]-Asn-Ser-Phe-NH$_2$

Ex. III.A.260:
[Arg$^{129}$][D-Cys$^{146}$]hANVP(130—146)—NH$_2$

H-Arg-Cys-Phe-Gly-Gly-Arg-Met-Asp-Arg-Ile-Gly-Ala-Gln-Ser-Gly-Leu-Gly-[D-Cys]-NH$_2$

Ex. III.A.261: [Arg$^{128}$][D-Ser$^{147}$]rANVP(129-150)

H-Arg-Cys-Phe-Gly-Gly-Arg-Ile-Asp-Arg-Ile-Gly-Ala-Gln-Ser-Gly-Leu-Gly-Cys-Asn-[D-Ser]-Phe-Arg-Tyr-OH

Ex. III.A.262:
[Arg$^{128}$][D-Ser$^{147}$]rANVP(129—148)—NH$_2$

H-Arg-Cys-Phe-Gly-Gly-Arg-Ile-Asp-Arg-Ile-Gly-Ala-Gln-Ser-Gly-Leu-Gly-Cys-Asn-[D-Ser]-Phe-Arg-NH$_2$

Ex. III.A.263: [Arg$^{129}$][D-Ser$^{148}$]hANVP(130-151)

H-Arg-Cys-Phe-Gly-Gly-Arg-Met-Asp-Arg-Ile-Gly-Ala-Gln-Ser-Gly-Leu-Gly-Cys-Asn-[D-Ser]-Phe-Arg-Tyr-OH

Ex. III.A.264:
[Arg$^{129}$][D-Ser$^{148}$]hANVP(130—150)—NH$_2$

H-Arg-Cys-Phe-Gly-Gly-Arg-Met-Asp-Arg-Ile-Gly-Ala-Gln-Ser-Gly-Leu-Gly-Cys-Asn-[D-Ser]-Phe-Arg-NH$_2$

Ex. III.A.265:
[Arg$^{129}$][D-Ser$^{148}$]hANVP(130—149)—NH$_2$

H-Arg-Cys-Phe-Gly-Gly-Arg-Met-Asp-Arg-Ile-Gly-Ala-Gln-Ser-Gly-Leu-Gly-Cys-Asn-[D-Ser]-Phe-NH$_2$

Ex. III.A.266: [D-Arg$^{128}$]rANVP(129-150)

H-[D-Arg]-Cys-Phe-Gly-Gly-Arg-Ile-Asp-Arg-Ile-Gly-Ala-Gln-Ser-Gly-Leu-Gly-Cys-Asn-Ser-Phe-Arg-Tyr-OH

Ex. III.A.267: [D-Arg$^{128}$]rANVP(129—148)—NH$_2$

H-[D-Arg]-Cys-Phe-Gly-Gly-Ag-Ile-Asp-Arg-Ile-Gly-Ala-Gln-Ser-Gly-Leu-Gly-Cys-Asn-Ser-Phe-NH$_2$

Ex. III.A.268: [D-Arg$^{128}$]rANVP(129—145)—NH$_2$

H-[D-Arg]-Cys-Phe-Gly-Gly-Arg-Ile-Asp-Arg-Ile-Gly-Ala-gln-Ser-Gly-Leu-Gly-Cys-NH$_2$ Ex. III.A.269: [D-Arg$^{129}$]hANVP(130-151)

H-[D-Arg]-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH

Ex. III.A.270: [D-Arg$^{129}$]hANVP(130—149)—NH$_2$

H-[d-Arg]-Cys-Phe-Gly-Gly-Arg-Met-Asp-Arg-Ile-Gly-Ala-Gln-Ser-Gly-Leu-Gly-Cys-AsnSer-Phe-NH$_2$

Ex. III.A.271: [D-Arg$^{129}$]hANVP(130—146)—NH$_2$

H-[D-Arg]-Cys-Phe-Gly-Gly-Arg-Met-Asp-Arg-Ile-Gly-Ala-Gln-Ser-Gly-Leu-Gly-Cys-NH$_2$

Ex. III.A.272 [Arg$^{128}$][D-Ala$^{131}$][D-Ala$^{142}$]rANVP(129-150)

H-Arg-Cys-Phe-[D-Ala]-Gly-Arg-Ile-Asp-Arg-Ile-Gly-Ala-Gln-Ser-[D-Ala]-Leu-Gly-Cys-Asn-Ser-Phe-Arg-Tyr-OH

Ex. III.A.273: [Arg$^{138}$][D-Ala$^{131}$][D-Ala$^{142}$]rANVP(129—148)—NH$_2$

H-Arg-Cys-Phe-[D-Ala]-Gly-Arg-Ile-Asp-Arg-Ile-Gly-Ala-Gln-Ser-[D-Ala]-Leu-Gly-Cys-Asn-Ser-Phe-NH$_2$

Ex. III.A.274: [Arg$^{128}$][D-Ala$^{131}$][D-Ala$^{142}$]rANVP(129—145)—NH$_2$

H-Arg-Cys-Phe-[D-Ala]-Gly-Arg-Ile-Asp-Arg-Ile-Gly-Ala-Gln-Ser-[D-Ala]-Leu-Gly-Cys-NH$_2$

Ex. III.A.275: [Arg$^{129}$][d-Ala$^{132}$][D-Ala$^{143}$]hANVP(130-151)

H-Arg-Cys-Phe-[D-Ala]-Gly-Arg-Met-Asp-Arg-Ile-Gly-Ala-Gln-Ser-[D-Ala]-Leu-Gly-Cys-Asn-Ser-Phe-Arg-Tyr-OH

Ex. III.A.276: [Arg$^{129}$][D-Ala$^{132}$][D-Ala$^{143}$]hANVP(130—149)—NH$_2$

H-Arg-Cys-Phe-[D-Ala]-Gly-Arg-Met-Asp-Arg-Ile-Gly-Ala-Gln-Ser-[D-Ala]-Leu-Gly-Cys-Asn-Ser-Phe-NH$_2$

Ex. III.A.277: [Arg$^{129}$][D-Ala$^{132}$][D-Ala$^{143}$]hANVP(130—146)—NH$_2$

H-Arg-Cys-Phe-[D-Ala]-Gly-Arg-Met-Asp-Arg-Ile-Gly-Ala-Gln-Ser-[D-Ala]-Leu-Gly-Cys-NH$_2$

Ex. III.A.278: [Arg$^{128}$][D-Ala$^{131}$][D-Cys$^{145}$]rANVP(129-150)

H-Arg-Cys-Phe-[D-Ala]-Gly-Arg-Ile-Asp-Arg-Ile-Gly-Ala-Gln-Ser-Gly-Leu-Gly-[D-Cys]-Asn-Ser-Phe-Arg-Tyr-OH

Ex. III.A.279: [Arg$^{128}$][D-Ala$^{131}$][D-Cys$^{145}$]rANVP(129—148)—NH$_2$

H-Arg-Cys-Phe-[D-Ala]-Gly-Arg-Ile-Asp-Arg-Ile-Gly-Ala-Gln-Ser-Gly-Leu-Gly-[D-Cys]-Asn-Ser-Phe-NH$_2$

Ex. III.A.280: [Arg$^{128}$][D-Ala$^{131}$][D-Cys$^{145}$]rANVP(129—145)—NH$_2$

H-Arg-Cys-Phe-[D-Ala]-Gly-Arg-Ile-Asp-Arg-Ile-Gly-Ala-Gln-Ser-Gly-Leu-Gly-[D-Cys]—NH$_2$

Ex. III.A.281: [Arg$^{129}$][D-Ala$^{132}$][D-Cys$^{146}$]hANVP(130-151)

H-Arg-Cys-Phe-[D-Ala]-Gly-Arg-Met-Asp-Arg-Ile-Gly-Ala-Gln-Ser-Gly-Leu-Gly-[D-Cys]-Asn-Ser-Phe-Arg-Tyr-OH

Ex. III.A.282: [Arg$^{129}$][D-Ala$^{132}$][D-Cys$^{146}$]hANVP (130—149)—NH$_2$

H-Arg-Cys-Phe-[D-Ala]-Gly-Arg-Met-Asp-Arg-Ile-Gly-Ala-Gln-Ser-GLy-Leu-Gly-[d-Cys]-Asn-Ser-Phe-NH$_2$

Ex. III.A.283: [Arg$^{129}$][D-Ala$^{132}$][D-Cys$^{146}$]hANVP (130—146)—NH$_2$

H-Arg-Cys-Phe-[D-Ala]-Gly-Arg-Met-Asp-Arg-Ile-Gly-Ala-Gln-Ser-GLy-Leu-Gly-[D-Cys]—NH$_2$

Ex. III.A.284: [Arg$^{128}$][D-Cys$^{129}$][D-Ala$^{131}$]rANVP (129-150)

H-Arg-[D-Cys]-Phe-[D-Ala]-Gly-Arg-Ile-Asp-Arg-Ile-Gly-Ala-Gln-Ser-Ala-Leu-Gly-Cys-Asn-Ser-Phe-Arg-Tyr-OH

Ex. III.A.285: [Arg$^{128}$][D-Cys$^{129}$][D-Ala$^{131}$]rANVP (129—148)—NH$_2$

H-Arg-[D-Cys]-Phe-[D-Ala]-Gly-Arg-Ile-Asp-Arg-Ile-Gly-Ala-Gln-Ser-Ala-Leu-Gly-Cys-Asn-Ser-Phe-NH$_2$

Ex. III.A.286: [Arg$^{128}$][D-Cys$^{129}$][D-Ala$^{131}$]rANVP (129—145)—NH$_2$

H-Arg-[D-Cys]-Phe-[D-Ala]-Gly-Arg-Ile-Asp-Arg-Ile-Gly-Ala-Gln-Ser-Ala-Leu-Gly-Cys-Nh$_2$

Ex. III.A.287: [Arg$^{129}$][D-Cys$^{130}$][D-Ala$^{132}$]hANVP (130-151)

H-Arg-[D-Cys]-Phe-[D-Ala]-Gly-Arg-Met-Asp-Arg-Ile-Gly-Ala-Gln-Ser-Ala-Leu-Gly-Cys-Asn-Ser-Phe-Arg-Tyr-OH

Ex. III.A.288: [Arg$^{129}$][D-Cys$^{130}$][D-Ala$^{132}$]hANVP (130—149)—NH$_2$

H-Arg-[D-Cys]-Phe-[D-Ala]-Gly-Arg-Met-Asp-Arg-Ile-Gly-Ala-Gln-Ser-Ala-Leu-Gly-Cys-Asn-Ser-Phe-NH$_2$

Ex. III.A.289: [Arg$^{129}$][D-Cys$^{130}$][D-Ala$^{132}$]hANVP (130—146)—NH$_2$

H-Arg-[D-Cys]-Phe-[D-Ala]-Gly-Arg-Met-Asp-Arg-Ile-Gly-Ala-Gln-Ser-Ala-Leu-Gly-Cys-NH$_2$

Ex. III.A.290: [Arg$^{128}$][D-Ala$^{131}$][D-Ser$^{147}$]rANVP (129-150)

H-Arg-Cys-Phe-[D-Ala]-Gly-Arg-Ile-Asp-Arg-Ile-Gly-Ala-Gln-Ser-Ala-Leu-Gly-Cys-Asn-[D-Ser]-Phe-Arg-Tyr-OH

Ex. III.A.291: [Arg$^{128}$][D-Ala$^{131}$][D-Ser$^{147}$]rANVP (129—148)—NH$_2$

H-Arg-Cys-Phe-[D-Ala]-Gly-Arg-Ile-Asp-Arg-Ile-Gly-Ala-Gln-Ser-Ala-Leu-Gly-Cys-Asn-[D-Ser]-Phe-NH$_2$

Ex. III.A.292: [Arg$^{128}$][D-Ala$^{131}$][D-Ser$^{147}$]rANVP (129—145)—NH$_2$

H-Arg-Cys-Phe-[D-Ala]-Gly-Arg-Ile-Asp-Arg-Ile-Gly-Ala-Gln-Ser-Leu-Gly-Cys-Asn-[D-Ser]-Phe-Arg-Tyr-NH$_2$

Ex. III.A.293: [Arg$^{129}$][D-Ala$^{132}$][D-Ser$^{148}$]hANVP (130-145)

H-Arg-Cys-Phe-[D-Ala]-Gly-Arg-Met-Asp-Arg-Ile-Gly-Ala-Gln-Ser-Leu-Gly-Cys-Asn-[D-Ser]-Phe-Arg-Tyr-OH

Ex. III.A.294: [Arg$^{129}$][D-Ala$^{132}$][D-Ser$^{148}$]hANVP (130—149)—NH$_2$

H-Arg-Cys-Phe-[D-Ala]-Gly-Arg-Met-Asp-Arg-Ile-Gly-Ala-Gln-Ser-Leu-Gly-Cys-Asn-[D-Ser]-Phe-NH$_2$

Ex. III.A.295: [Arg$^{129}$][D-Ala$^{132}$][D-Ser$^{148}$]hANVP (130—146)—NH$_2$

H-Arg-Cys-Phe-[D-Ala]-Gly-Arg-Met-Asp-Arg-Ile-Gly-Ala-Gln-Ser-Leu-Gly-Cys-Asn-[D-Ser]-Phe-Arg-Tyr-NH$_2$

Ex. III.A.296: [Arg$^{128}$][Asn$^{135}$]rANVP(129-150)

H-Arg-Cys-Phe-Gly-Gly-Arg-Ile-Asn-Arg-Ile-Gly-Ala-gln-Ser-Leu-Gly-Cys-Asn-Ser-Phe-Arg-tyr-OH Ex. III.A.297: [Arg$^{128}$][Asn$^{135}$]rANVP(126—148)—NH$_2$ H-Arg-Cys-Phe-Gly-Gly-Arg-Ile-Asn-Arg-Ile-Gly-Ala-Gln-Ser-Leu-Gly-Cys-Asn-Ser-Phe-NH$_2$ Ex. III.A.289: [Arg$^{128}$][Asn$^{135}$]rANVP(129—145)—NH$_2$ H-Arg-Cys-Phe-Gly-Gly-Arg-Ile-Asn-Arg-Ile-Gly-Ala-Gln-Ser-Leu-Gly-Cys-NH$_2$ Ex. III.A.299: [Arg$^{129}$][Asn$^{136}$]hANVP(130-151)

H-Arg-Cys-Phe-Gly-Gly-Arg-Met-Asn-Arg-Ile-Gly-Ala-Gln-Ser-Leu-Gly-Cys-Asn-Ser-Phe-Arg-Tyr-OH

Ex. III.A.300: [Arg$^{129}$][Asn$^{136}$]hANVP(130—149)—NH$_2$

H-Arg-Cys-Phe-Gly-Gly-Arg-Met-Asn-Arg-Ile-Gly-Ala-Gln-Ser-Leu-Gly-Cys-Asn-Ser-Phe-NH$_2$

Ex. III.A.301: [Arg$^{129}$][Asn$^{136}$]hANVP(130—146)—NH$_2$

H-Arg-Cys-Phe-Gly-Gly-Arg-Met-Asn-Arg-Ile-Gly-Ala-Gln-Ser-Leu-Gly-Cys-NH$_2$

* Ex. III.A.302: [Nle$^{133}$]rANVP(126-150)

H-Arg-Ser-Ser-Cys-Phe-Gly-Gly-Nle-Ile-Asp-Arg-Ile-Gly-Ala-Gln-Ser-Gly-Leu-Gly-Cys-Asn-Ser-Phe-Arg-Tyr-OH

Ex. III.A.303: [Nle$^{133}$]rANVP(126—150)—NH$_2$

H-Arg-Ser-Ser-Cys-Phe-Gly-Gly-Nle-Ile-Asp-Arg-Ile-Gly-Ala-Gln-Ser-Gly-Leu-Gly-Cys-Asn-Ser-Phe-Arg-Tyr-NH$_2$

Ex. III.A.304: [Nle$^{133}$]rANVP(126-149)

H-Arg-Ser-Ser-Cys-Phe-Gly-Gly-Nle-Ile-Asp-Arg-Ile-Gly-Ala-Gln-Ser-Gly-Leu-Gly-Cys-Asn-Ser-Phe-Arg-OH

Ex. III.A.305: [Nle$^{133}$]rANVP(126—149)—NH$_2$

H-Arg-Ser-Ser-Cys-Phe-Gly-Gly-Nle-Ile-Asp-Arg-Ile-Gly-Ala-Gln-Ser-Gly-Leu-Gly-Cys-Asn-Ser-Phe-Arg-NH$_2$

Ex. III.A.306: [Nle$^{133}$]rANVP(126—148)—NH$_2$

H-Arg-Ser-Ser-Cys-Phe-Gly-Gly-Nle-Ile-Asp-Arg-Ile-Gly-Ala-gln-Ser-Gly-Leu-Gly-Cys-Asn-Ser-Phe-NH$_2$ Ex. III.A.307: [Nle$^{133}$]rANVP(126—145)—NH$_2$ H-Arg-Ser-Ser-Cys-Phe-Gly-Gly-Nle-Ile-Asp-Arg-Ile-Gly-Ala-Gln-Ser-Gly-Leu-Gly-Cys-NH$_2$ Ex. III.A.308: [Nle$^{134}$]hANVP(127-151)

H-Arg-Ser-Ser-Cys-Phe-Gly-Gly-Nle-Met-Asp-Arg-Ile-Gly-Ala-Gln-Ser-Gly-Leu-Gly-Cys-Asn-Ser-Phe-Arg-Tyr-OH

Ex. III.A.309: [Nle$^{134}$]hANVP(127—151)—NH$_2$

H-Arg-Ser-Ser-Cys-Phe-Gly-Gly-Nle-Met-Asp-Arg-Ile-Gly-Ala-Gln-Ser-Gly-Leu-Gly-Cys-Asn-Ser-Phe-Arg-Tyr-NH$_2$

Ex. III.A.310: [Nle$^{134}$]hANVP(127-150)

H-Arg-Ser-Ser-Cys-Phe-Gly-Gly-Nle-Met-Asp-Arg-Ile-Gly-Ala-Gln-Ser-Gly-Leu-Gly-Cys-Asn-Ser-Phe-Arg-OH

Ex. III.A.311: [Nle$^{134}$]hANVP(127—150)—NH$_2$

H-Arg-Ser-Ser-Cys-Phe-Gly-Gly-Nle-Met-Asp-Arg-Ile-Gly-Ala-Gln-Ser-Gly-Leu-Gly-Cys-Asn-Ser-Phe-Arg-NH$_2$

Ex. III.A.312: [Nle$^{134}$]hANVP(127—146)—NH$_2$

H-Arg-Ser-Ser-Cys-Phe-Gly-Gly-Nle-Met-Asp-Arg-Ile-Gly-Ala-Gln-Ser-Gly-Leu-Gly-Cys-NH$_2$

Ex. III.A.313: [Nle$^{134}$]hANVP(127—149)—NH$_2$

H-Arg-Ser-Ser-Cys-Phe-Gly-Gly-Nle-Met-Asp-Arg-Ile-Gly-Ala-Gln-Ser-Gly-Leu-Gly-Cys-Asn-Ser-Phe-NH$_2$

* Ex. III.A.314: [Ser$^{135}$]rANVP(126-150)

H-Arg-Ser-Ser-Cys-Phe-Gly-Gly-Arg-Ile-Ser-Arg-Ile-Gly-Ala-Gln-Ser-Gly-Leu-Gly-Cys-Asn-Ser-Phe-Arg-Tyr-OH

Ex. III.A.315: [Ser$^{135}$]rANVP(126—150)—NH$_2$

H-Arg-Ser-Ser-Cys-Phe-Gly-Gly-Arg-Ile-Ser-Arg-Ile-Gly-Ala-Gln-Ser-Gly-Leu-Gly-Cys-Asn-Ser-Phe-Arg-Tyr-NH$_2$

Ex. III.A.316: [Ser$^{135}$]rANVP(126-149)

H-Arg-Ser-Ser-Cys-Phe-Gly-Gly-Arg-Ile-Ser-Arg-Ile-Gly-Ala-Gln-Ser-Gly-Leu-Gly-Cys-Asn-Ser-Phe-Arg-OH

Ex. III.A.317: [Ser$^{135}$]rANVP(126—149)—NH$_2$

H-Arg-Ser-Ser-Cys-Phe-Gly-Gly-Arg-Ile-Ser-Arg-Ile-Gly-Ala-Gln-Ser-Gly-Leu-Gly-Cys-Asn-Ser-Phe-Arg-NH$_2$

Ex. III.A.318: [Ser$^{135}$]rANVP(126—148)—NH$_2$

H-Arg-Ser-Ser-Cys-Phe-Gly-Gly-Arg-Ile-Ser-Arg-Ile-Gly-Ala-Gln-Ser-Gly-Leu-Gly-Cys-Asn-Ser-Phe-NH$_2$

Ex. III.A.319: [Ser$^{135}$]rANVP(126—145)—NH$_2$

H-Arg-Ser-Ser-Cys-Phe-Gly-Gly-Arg-Ile-Ser-Arg-Ile-Gly-Ala-Gln-Ser-Gly-Leu-Gly-Cys-NH$_2$

Ex. III.A.320: [Ser$^{136}$]hANVP(127-151)

H-Arg-Ser-Ser-Cys-Phe-Gly-Gly-Arg-Met-Ser-Arg-Ile-Gly-Ala-Gln-Ser-Gly-Leu-Gly-Cys-Asn-Ser-Phe-Arg-Tyr-OH

Ex. III.A.321: [Ser$^{136}$]hANVP(127—151)—NH$_2$

H-Arg-Ser-Ser-Cys-Phe-Gly-Gly-Arg-Met-Ser-Arg-Ile-Gly-Ala-Gln-Ser-Gly-Leu-Gly-Cys-Asn-Ser-Phe-Arg-Tyr-NH$_2$

Ex. III.A.322: [Ser$^{136}$]hANVP(127-150)

H-Arg-Ser-Ser-Cys-Phe-Gly-Gly-Arg-Met-Ser-Arg-Ile-Gly-Ala-Gln-Ser-Gly-Leu-Gly-Cys-Asn-Ser-Phe-Arg-OH

Ex. III.A.323: [Ser$^{136}$]hANVP(127—150)—NH$_2$

H-Arg-Ser-Ser-Cys-Phe-Gly-Gly-Arg-Met-Ser-Arg-Ile-Gly-Ala-Gln-Ser-Gly-Leu-Gly-Cys-Asn-Ser-Phe-Arg-NH$_2$

Ex. III.A.324: [Ser$^{136}$]hANVP(127—149)—NH$_2$

H-Arg-Ser-Ser-Cys-Phe-Gly-Gly-Arg-Met-Ser-Arg-Ile-Gly-Ala-Gln-Ser-Gly-Leu-Gly-Cys-Asn-Ser-Phe-NH$_2$

Ex. III.A.325: [Ser$^{136}$]hANVP(127—146)—NH$_2$

H-Arg-Ser-Ser-Cys-Phe-Gly-Gly-Arg-Met-Ser-Arg-Ile-Gly-Ala-Gln-Ser-Gly-Leu-Gly-Cys-NH$_2$

* Ex. III.A.236: [Nle$^{136}$]rANVP(126-150)

H-Arg-Ser-Ser-Cys-Phe-Gly-Gly-Arg-Ile-Asp-Nle-Ile-Gly-Ala-Gln-Ser-Gly-Leu-Gly-Cys-Asn-Ser-Phe-Arg-Tyr-OH

Ex. III.A.327: [Nle$^{137}$]hANVP(127-151)

H-Arg-Ser-Ser-Cys-Phe-Gly-Gly-Arg-Met-Asp-Nle-Ile-Gly-Ala-Gln-Ser-Gly-Leu-Gly-Cys-Asn-Ser-Phe-Arg-Tyr-OH

* Ex. III.A.328: [Lys$^{133}$]rANVP(126-150)

H-Arg-Ser-Ser-Cys-Phe-Gly-Gly-Lys-Ile-Asp-Arg-Ile-Gly-Ala-Gln-Ser-Gly-Leu-Gly-Cys-Asn-Ser-Phe-Arg-Tyr-OH

Ex. III.A.329: [Lys$^{134}$]hANVP(127-151)

H-Arg-Ser-Ser-Cys-Phe-Gly-Gly-Lys-Met-Asp-Arg-Ile-Gly-Ala-Gln-Ser-Gly-Leu-Gly-Cys-Asn-Ser-Phe-Arg-Tyr-OH

Ex. III.A.330: [Lys$^{136}$]rANVP(126-150)

H-Arg-Ser-Ser-Cys-Phe-Gly-Gly-Arg-Ile-Asp-Lys-Ile-Gly-Ala-Gln-Ser-Gly-Leu-Gly-Cys-Asn-Ser-Phe-Arg-Tyr-OH

Ex. III.A.331: [Lys¹³⁷]hANVP(127-151)

H-Arg-Ser-Ser-Cys-Phe-Gly-Gly-Arg-Met-Asp-Lys-Ile-Gly-Ala-Gln-Ser-Gly-Leu-Gly-Cys-Asn-Ser-Phe-Arg-Tyr-OH

* Ex. III.A.332: [Leu¹³⁰]rANVP(126-150)

H-Arg-Ser-Ser-Cys-Leu-Gly-Gly-Arg-Ile-Asp-Arg-Ile-Gly-Ala-Gln-Ser-Gly-Leu-Gly-Cys-Asn-Ser-Phe-Arg-Tyr-OH

Ex. III.A.333: [Leu¹³⁰]rANVP(126—150)—NH₂

H-Arg-Ser-Ser-Cys-Leu-Gly-Gly-Arg-Ile-Asp-Arg-Ile-Gly-Ala-Gln-Ser-Gly-Leu-Gly-Cys-Asn-Ser-Phe-Arg-tyr-NH₂

Ex. III.A.334: [Leu¹³⁰]rANVP(126-149)

H-Arg-Ser-Ser-Cys-Leu-Gly-Gly-Arg-Ile-Asp-Arg-Ile-Gly-Ala-Gln-Ser-Gly-Leu-Gly-Cys-Asn-Ser-Phe-Arg-OH

Ex. III.A.335: [Leu¹³⁰]rANVP(126—149)—NH₂

H-Arg-Ser-Ser-Cys-Leu-Gly-Gly-Arg-Ile-Asp-Arg-Ile-Gly-Ala-Gln-Ser-Gly-Leu-Gly-Cys-Asn-Ser-Phe-Arg-NH₂

Ex. III.A.336: [Leu¹³⁰]rANVP(126—148)—NH₂

H-Arg-Ser-Ser-Cys-Leu-Gly-Gly-Arg-Ile-Asp-Arg-Ile-Gly-Ala-Gln-Ser-Gly-Leu-Gly-Cys-Asn-Ser-Phe-NH₂

Ex. III.A.337: [Leu¹³⁰]rANVP(126—145)—NH₂

H-Arg-Ser-Ser-Cys-Leu-Gly-Gly-Arg-Ile-Asp-Arg-Ile-Gly-Ala-Gln-Ser-Gly-Leu-Gly-Cys-NH₂

Ex. III.A.338: [Leu¹³¹]hANVP(127-151)

H-Arg-Ser-Ser-Cys-Leu-Gly-Gly-Arg-Met-Asp-Arg-Ile-Gly-Ala-Gln-Ser-Gly-Leu-Gly-Cys-Asn-Ser-Phe-Arg-Tyr-OH

Ex. III.A.339: [Leu¹³¹]hANVP(127—151)—NH₂

H-Arg-Ser-Ser-Cys-Leu-Gly-Gly-Arg-Met-Asp-Arg-Ile-Gly-Ala-Gln-Ser-Gly-Leu-Gly-Cys-Asn-Ser-Phe-Arg-Tyr-NH₂

Ex. III.A.340: [Leu¹³¹]hANVP(127-150)

H-Arg-Ser-Ser-Cys-Leu-Gly-Gly-Arg-Met-Asp-Arg-Ile-Gly-Ala-Gln-Ser-Gly-Leu-Gly-Cys-Asn-Ser-Phe-Arg-OH

Ex. III.A.341: [Leu¹³¹]hANVP(127—150)—NH₂

H-Arg-Ser-Ser-Cys-Leu-Gly-Gly-Arg-Met-Asp-Arg-Ile-Gly-Ala-Gln-Ser-Gly-Leu-Gly-Cys-Asn-Ser-Phe-Arg-NH₂

Ex. III.A.342: [Leu¹³¹]hANVP(127—149)—NH₂

H-Arg-Ser-Ser-Cys-Leu-Gly-Gly-Arg-Met-Asp-Arg-Ile-Gly-Ala-Gln-Ser-Gly-Leu-Gly-Cys-Asn-Ser-Phe-NH₂

Ex. III.A.343: [Leu¹³¹]hANVP(127—146)—NH₂

H-Arg-Ser-Ser-Cys-Leu-Gly-Gly-Arg-Met-Asp-Arg-Ile-Gly-Ala-gln-Ser-Gly-Leu-Gly-Cys-NH₂

* Ex. III.A.344: [Ala¹³⁰]rANVP(126-150)

H-Arg-Ser-Ser-Cys-Ala-Gly-Gly-Arg-Ile-Asp-Arg-Ile-Gly-Ala-Gln-Ser-Gly-Leu-Gly-Cys-Asr-Ser-Phe-Arg-Tyr-OH

Ex. III.A.345: [Ala¹³⁰]rANVP(126—150)—NH₂

H-Arg-Ser-Ser-Cys-Ala-Gly-Gly-Arg-Ile-Asp-Arg-Ile-Gly-Ala-Gln-Ser-Gly-Leu-Gly-Cys-Asr-Ser-Phe-Arg-Tyr-NH₂

Ex. III.A.346: [Ala¹³⁰]rANVP(126-149)

H-Arg-Ser-Ser-Cys-Ala-Gly-Gly-Arg-Ile-Asp-Arg-Ile-Gly-Ala-Gln-Ser-Gly-Leu-Gly-Cys-Asr-Ser-Phe-Arg-OH

Ex. III.A.347: [Ala¹³⁰]rANVP(126—149)—NH₂

H-Arg-Ser-Ser-Cys-Ala-Gly-Gly-Arg-Ile-Asp-Arg-Ile-Gly-Ala-Gln-Ser-Gly-Leu-Gly-Cys-Asr-Ser-Phe-Arg-NH₂

Ex. III.A.348: [Ala¹³⁰]rANVP(126—148)—NH₂

H-Arg-Ser-Ser-Cys-Ala-Gly-Gly-Arg-Ile-Asp-Arg-Ile-Gly-Ala-Gln-Ser-Gly-Leu-Gly-Cys-Asr-Ser-Phe-NH₂

Ex. III.A.349: [Ala¹³⁰]rANVP(126—145)—NH₂

H-Arg-Ser-Ser-Cys-Ala-Gly-Gly-Arg-Ile-Asp-Arg-Ile-Gly-Ala-Gln-Ser-Gly-Leu-Gly-Cys-NH₂

Ex. III.A.350: [Ala¹³¹]hANVP(127-151)

H-Arg-Ser-Ser-Cys-Ala-Gly-Gly-Arg-Met-Asp-Arg-Ile-Gly-Ala-Gln-Ser-Gly-Leu-Gly-Cys-Asr-Ser-Phe-Arg-Tyr-OH

Ex. III.A.351: [Ala¹³¹]hANVP(127—151)—NH₂

H-Arg-Ser-Ser-Cys-Ala-Gly-Gly-Arg-Met-Asp-Arg-Ile-Gly-Ala-Gln-Ser-Gly-Leu-Gly-Cys-Asr-Ser-Phe-Arg-Tyr-NH₂

Ex. III.A.352: [Ala¹³¹]hANVP(127-150)

H-Arg-Ser-Ser-Cys-Ala-Gly-Gly-Arg-Met-Asp-Arg-Ile-Gly-Ala-Gln-Ser-Gly-Leu-Gly-Cys-Asr-Ser-Phe-Arg-OH

Ex. III.A.353: [Ala¹³¹]hANVP(127—150)—NH₂

H-Arg-Ser-Ser-Cys-Ala-Gly-Gly-Arg-Met-Asp-Arg-Ile-Gly-Ala-Gln-Ser-Gly-Leu-Gly-Cys-Asr-Ser-Phe-Arg-NH₂

Ex. III.A.354: [Ala¹³¹]hANVP(127—149)—NH₂

H-Arg-Ser-Ser-Cys-Ala-Gly-Gly-Arg-Met-Asp-Arg-Ile-Gly-Ala-Gln-Ser-Gly-Leu-Gly-Cys-Asr-Ser-Phe-NH₂

Ex. III.A.355: [Ala¹³¹]hANVP(127—146)—NH₂

H-Arg-Ser-Ser-Cys-Ala-Gly-Gly-Arg-Met-Asp-Arg-Ile-Gly-Ala-Gln-Ser-Gly-Leu-Gly-Cys-NH₂

* Ex. III.A.356: [Val¹³⁵]rANVP(126-150)

H-Arg-Ser-Ser-Cys-Phe-Gly-Gly-Arg-Ile-Val-Arg-Ile-Gly-Ala-Gln-Ser-Gly-Leu-Gly-Cys-Asn-Ser-Phe-Arg-Tyr-OH

Ex. III.A.357: [Val$^{136}$]hANVP(127-151)

H-Arg-Ser-Ser-Cys-Phe-Gly-Gly-Arg-Met-Val-Arg-
Ile-Gly-Ala-Gln-Ser-Gly-Leu-Gly-Cys-Asn-Ser-
Phe-Arg-Tyr-OH

* Ex. III.A.358: [Glu$^{135}$]rANVP(126-150)

H-Arg-Ser-Ser-Cys-Phe-Gly-Gly-Arg-Ile-Glu-Arg-Ile-
Gly-Ala-Gln-Ser-Gly-Leu-Gly-Cys-Asn-Ser-Phe-
Arg-Tyr-OH

Ex. III.A.359: [Glu$^{136}$]hANVP(127-151)

H-Arg-Ser-Ser-Cys-Phe-Gly-Gly-Arg-Met-Glu-Arg-
Ile-Gly-Ala-Gln-Ser-Gly-Leu-Gly-Cys-Asn-Ser-
Phe-Arg-Tyr-OH

* Ex. III.A.360: [D-Ile$^{134}$]rANVP(126-150)

H-Arg-Ser-Ser-Cys-Phe-Gly-Gly-Arg-[D-Ile]-Asp-
Arg-Ile-Gly-Ala-Gln-Ser-Gly-Leu-Gly-Cys-Asn-
Ser-Phe-Arg-Tyr-OH

Ex. III.A.361: [D-Ile$^{137}$]rANVP(126-150)

H-Arg-Ser-Ser-Cys-Phe-Gly-Gly-Arg-Ile-Asp-Arg-
[D-Ile]-Gly-Ala-Gln-Ser-Gly-Leu-Gly-Cys-Asn-Ser-
Phe-Arg-Tyr-OH

Ex. III.A.362: [D-Ile$^{138}$]hANVP(127-151)

H-Arg-Ser-Ser-Cys-Phe-Gly-Gly-Arg-Met-Asp-Arg-
[D-Ile]-Gly-Ala-Gln-Ser-Gly-Leu-Gly-Cys-Asn-Ser-
Phe-Arg-Tyr-OH

* Ex. III.A.363: [D-Asp$^{135}$]rANVP(126-150)

H-Arg-Ser-Ser-Cys-Phe-Gly-Gly-Arg-Ile-[D-Asp]-
Arg-Ile-Gly-Ala-Gln-Ser-Gly-Leu-Gly-Cys-Asn-
Ser-Phe-Arg-Tyr-OH

Ex. III.A.364: [D-Asp$^{136}$]hANVP(127-151)

H-Arg-Ser-Ser-Cys-Phe-Gly-Gly-Arg-Met-[D-Asp]-
Arg-Ile-Gly-Ala-Gln-Ser-Gly   Leu-Gly-Cys-Asn-
Ser-Phe-Arg-Tyr-OH

Ex. III.A.365: [D-Ala$^{139}$]hANVP(127-151)

H-Arg-Ser-Ser Cys Phe-Gly-Gly-Arg-Met-Asp-Arg-
Ile-[D-Ala]-Ala-Gln-Ser-Gly-Leu-Gly-Cys-Asn-Ser-
Phe-Arg-Tyr-OH

Ex. III.A.366: D-Ala$^{140}$]hANVP(127-151)

H-Arg-Ser-Ser-Cys-Phe-Gly-Gly-Arg-Met-Asp-Arg-
Ile-Gly-[D-Ala]-Gln-Ser-Gly-Leu-Gly-Cys-Asn-Ser-
Phe-Arg-Tyr-OH

In each of the above examples, designated "*", amino acid analysis demonstrated that the appropriate amino acid sequence of the peptide was obtained.

B. BIOLOGICAL ACTIVITY OF NATIVE AND CHEMICALLY PRODUCED ATRIAL NATRIURETIC/VASODILATOR PEPTIDE

The biologic activities of native and chemically synthesized ANVP compounds were determined using in vitro systems, including isolated rat kidneys, isolated rabbit thoracic aortic rings and isolated vascular wall cells. The activities were also measured in intact rats and dogs.

1. In Vitro Biological Assays

The activity of rANVP(126-149) was measured in the isolated rat kidney. Functioning isolated rat kidneys were perfused in a closed-circuit system, as described in Camargo, M.J.F. et al., Am. J. Physiol. 246:F447-F456 (1984). After control clearance periods, 0.1 to 1.0 μg of the selected compound was added to the perfusate. The effects on multiple parameters were recorded. The peak values are expressed in Table I as the experimental data.

TABLE I

Effects of rANVP(126-149) on Renal Function in the Isolated Perfused Rat Kidney

|  | Control | Experimental |
|---|---|---|
| GFR (ml/min) | 0.43 ± 0.05 | 0.63 ± 0.03* |
| FF | 0.014 ± 0.002 | 0.021 ± 0.001* |
| RVR (mmHg/ml/min) | 2.9 ± 0.1 | 3.9 ± 0.3* |
| V̇ (μl/min) | 19.8 ± 4.8 | 97.6 ± 19.4* |
| FL$_{Na}$ (μEq/min) | 60.2 ± 7.9 | 90.1 ± 5.2* |
| T$_{Na}$ (μEq/min) | 60.0 ± 7.6 | 84.2 ± 4.8* |
| U$_{Na}$V̇ (μEq/min) | 0.66 ± 0.35 | 6.01 ± 1.99* |
| FE$_{Na}$ (%) | 0.97 ± 0.38 | 6.6 ± 2.0* |
| U$_K$V̇ (μEq/min) | 0.44 ± 0.19 | 1.46 ± 0.16* |
| FE$_K$ (%) | 19.8 ± 5.9 | 52.1 ± 6.2* |

GFR = glomerular filtration rate; FF = filtration fraction; RVR = renal vascular resistance; V̇ = urine flow rate; FL$_{Na}$ = filtered load of sodium; T$_{Na}$ = tubular reabsorption of sodium; U$_{Na}$V̇ = urinary sodium excretion rate; FE$_{Na}$ = fractional sodium excretion; U$_K$V̇ = urinary potassium excretion rate; FE$_K$ = fractional potassium excretion. Results are the mean ± SE of 4 kidneys. *P < 0.05 compared to control (Student's t test).

It is clear that rANVP(126-149) caused urine flow rate, urinary sodium excretion, filtration fraction and glomerular filtration rate to increase. These results also so that, in isolated kidneys perfused in the absence of vasoconstrictors, the compounds of the present invention increased renal vascular resistance, filtration fraction and glomerular filtration rate. In contrast, in isolated kidneys precontracted with endogenously generated angiotensin, the present compounds decreased vascular resistance. These effects with the synthetic compounds show that ANVP compounds can have both renal vasoconstrictive and vasorelaxant activity, depending on the absence or presence of endogenous vasoconstrictors. The natriuresis observed in the isolated kidney can result from a renal vasoconstrictive effect preferentially expressed in the efferent arteriole.

In a similar manner, the effects of other ANVP compounds were examined in the isolated rat kidney. Table II summarizes the effects of these peptides on urinary flow rate, urinary sodium excretion and glomerular filtration rate. It should be noted that most ANVP compounds tested in this system increased urine flow rate and urinary sodium excretion. Relatively few unrelated peptides effect flow rate and sodium excretion in this manner in the isolated rat kidney. Thus the observed effects are specific to the ANVP compounds and related analogs. These effects are presumably mediated by the interaction of the ANVP compounds with specific receptor sites within the kidney.

TABLE II

Effects of ANVP Compounds in the Isolated Rat Kidney

| (dose) Peptide | | (μl/min) V̇ | (μEq/min) UNaV̇ | (ml/min) GFR |
|---|---|---|---|---|
| (1 μg) | C | 11.8 | 0.37 | 0.35 |
| rANVP(126-150) | E | 97.3 | 5.99 | 0.72 |
| (1 μg) | C | 25.2 | 0.72 | 0.67 |
| hANVP(127-151) | E | 142.3 | 8.6 | 0.94 |
| (1 μg) | C | 5.9 | 0.11 | 0.18 |
| [D-Ala$^{138}$]rANVP (126-150) | E | 57.5 | 2.53 | 0.54 |
| (1 μg) | C | 7.8 | 0.25 | 0.22 |
| [D-Ala$^{139}$]rANVP (126-150) | E | 112.5 | 8.14 | 0.59 |
| (1 μg) | C | 10.2 | 0.70 | 0.24 |

TABLE II-continued

Effects of ANVP Compounds in the Isolated Rat Kidney

| Peptide (dose) | | (μl/min) V̇ | (μEq/min) UNaV̇ | (ml/min) GFR |
|---|---|---|---|---|
| [D-Gln140]rANVP (126-150) | E | 183.4 | 14.52 | 1.01 |
| (1 μg) | C | 0.42 | 0.10 | 0.20 |
| [D-Ser141]rANVP (126-150) | E | 29.2 | 2.10 | 0.51 |
| (0.1 μg) | C | 12.2 | 0.26 | 0.37 |
| [D-Ala142]rANVP (126-150) | E | 58.5 | 2.50 | 0.75 |
| (1 μg) | C | 14.0 | 0.35 | 0.34 |
| [D-Leu143]rANVP (126-150) | E | 103.0 | 3.52 | 0.53 |

Isolated rat kidneys were treated as described in Table I. Control periods for each compound are denoted by C and experimental periods following the addition of compounds are denoted by E. V̇, $U_{Na}$V̇ and GFR are as defined in Table I. Data represent the mean of 3-8 experiments.

Since native ANVP compounds relax precontracted blood vessels, the effects of these peptides on isolated thoracic aortic preparation from rabbits and rats and on isolated vascular wall cells of bovine origin were determined.

Synthetic ANVP compounds were compared to partially purified (gel filtration step) and purified (HPLC) native ANVP compounds (See FIGS. 3A-D) for their ability to relax histamine-contracted aortic rings. Rings were suspended in 10 ml aerated Kreb's buffer under 1.5 gm passive tension. Rings were precontracted with 5 X 10-6 M histamine, washed and allowed to return to baseline tension, as described (Kleinert, H. D., supra). Increasing amounts of purified or synthetic ANVP compounds were then added in cumulative fashion. The change in tension was shown to be related to the cumulative amount of protein added, as seen in FIG. 8.

As shown, both purified native rANVP(126-150) and synthetic rANVP(126-150) relaxed the tissue at the same doses. In addition, hANVP(127-151) is equivalent to rANVP(126-150) in this tissue. However, rANVP(1-27-150), the equivalent of atriopeptin III described by Geller, et al., Biochem. Biophys. Res. Comm. 120(2):333-338 (1984), is significantly less potent in relaxing the precontracted rabbit aorta. This observation has been confirmed by Garcia, et al., BioChem. Biophys. Res. Comm. 126(1):178-184 (1985).

The relaxation effects of various ANVP compounds on precontracted rabbit or rat aortic preparations are shown in Table III.

TABLE III

Vasorelaxant Potency of Various ANVP Analogs on Precontracted Aortic Rings

| Peptide | IC50 |
|---|---|
| hANVP(127-151) | 0.92 |
| rANVP(126-150) | 0.84 |
| rANVP(126-150)-NH2 | 0.80 |
| rANVP(126-148)-NH2 | 2.50 |
| rANVP(126-148) | 7.5 |
| rANVP(126-147)-NH2 | 13 |
| rANVP(126-147) | 72.0 |
| hANVP(127-146) | 100 |
| [D-Cys129]rANVP(126-150) | 6.1 |
| [Ala130]rANVP(126-150) | >100 |
| [D-Ala131]rANVP(126-150) | 0.9 |
| [Pro132]rANVP(126-150) | 3.25 |
| [D-Arg133]rANVP(126-150) | 13.0 |
| [D-Val134]rANVP(126-150) | 13.0 |
| [D-Met135]hANVP(127-151) | 7.6 |
| [D-Asp135]rANVP(126-150) | 28.0 |
| [D-Arg136]rANVP(126-150) | 0.64 |
| [D-Val137]rANVP (126-150) | 40.0 |
| [D-Ala138]rANVP(126-150) | 3.1 |
| [D-Ala139]rANVP(126-150) | 2.7 |
| [D-Gln140]rANVP(126-150) | 1.25 |
| [D-Ser141]rANVP(126-150) | 11.0 |
| [D-Ala142]rANVP(126-150) | 0.62 |
| [D-Leu143]rANVP(126-150) | 3.6 |
| [D-Cys145]rANVP(126-150) | 24.0 |
| [D-Asn146]rANVP(126-150) | 4.4 |

Thoracic aortic segments were precontracted with histamine or norepinephrine as previously described. Various doses of ANVP compounds were then added and relaxation of the precontracted state was monitored. Data are expressed as the concentration of each peptide required to produce a half-maximal relaxation of the precontracted tissue (IC50).

As shown in Table III, graded vasorelaxant effects of the ANVP compounds can be determined in this preparation. Of the ANVP compounds tested, the most potent peptides were [D-Ala142]rANVP(126-150), [D-Arg136]rANVP(126-150), rANVP(126-150), rANVP(126-150)-NH2, hANVP(127-151), [D-Ala131]rANVP(126-150), [D-Gln140]rANVP(126-150), and rANVP(126-148)—NH2. It should be noted that, as amino acids are removed sequentially from the Carboxylterminus of the peptide, the ability to relax precontracted vascular preparations is decreased. Thus, for example, rANVP(126-147) and hANVP(127-146) show a substantially diminished potency in this bioassay.

In order to relax precontracted aortic vessels, the ANVP compounds first bind to specific membrane receptors. Associated with this ligand-receptor interaction is an increase in intracellular cyclic GMP (Winquist et al., Proc. Natl. Acad. Sci. USA, 81:7661-7664 (1984)). Since cyclic GMP has been identified as the intracellular mediator of vasorelaxation in responses to ANVP and other compounds, assessment of cyclic GMP levels provides an additional marker for determining the biological actions of ANVP compounds. Therefore, cells of vascular wall origin, e.g. bovine aortic smooth muscle (BASM) and endothelial (BAE) cells, were used to determine binding of ANVP compounds to specific receptors and associated cyclic GMP increases were measured. These tests will reflect the relative potency of the ANVPs in relaxing bovine vascular smooth muscle.

Binding assays were performed as follows: ANVP compounds were labelled with [125I] according to the procedure of Schenk, et al., J. Biol. Chem. 259:14941-14951 (1984). This procedure utilizes glucose oxidase- and lactoperoxidase-mediated oxidations to transfer [125I to the tyrosine on the ANVP molecule. [125I]-ANVP was added to 10 mm petri dishes containing confluent cultures of vascular wall cells and incubated at 37° C.

As shown in FIG. 9, the [125I]-ANVP binds to the cells in a specific and saturable manner. Specific and saturable binding is a necessary component of a hormone/receptor interaction. Furthermore, [125I]-ANVP binding can be displaced by unlabelled ANVP compounds and not by a variety of hormones (angiotensin, epinephrine, vasopressin, glucagon) that act at other receptor sites. Thus, the displacement of [125I]-ANVP binding by ANVPs and analogs as a function of concentration is a reflection of their potency to bind to the vascular wall. Concentrations at which ANVP compounds displace [$^{125}$I]-ANVP from binding sites on vascular smooth muscle cells are outlined in Table IV.

TABLE IV

Binding of ANVP Compounds to Cultured Bovine Vascular Smooth Muscle Cells

| Peptide | Ki(nM) |
|---|---|
| A | |
| hANVP(127-151) | 0.5 |
| [D-Ala$^{142}$]rANVP(126-150) | 0.6 |
| rANVP(126-150) | 0.8 |
| rANVP(127-150) | 2.4 |
| hANVP(128-151) | 7.0 |
| [D-Ala$^{138}$]rANVP(126-150) | 20.0 |
| [D-Gln$^{140}$]rANVP(126-150) | 20.0 |
| [D-Ser$^{141}$]rANVP(126-150) | 40.0 |
| B | |
| hANVP(127-151) | 1.12 |
| rANVP(126-150) | 1.58 |
| rANVP(126-149) | 0.89 |
| rANVP(126-148) | 1.32 |
| hANVP(127-149) | 2.45 |
| rANVP(126-148)NH$_2$ | 1.52 |
| rANVP(126-147) | 1.55 |
| rANVP(126-147)NH$_2$ | 1.83 |
| hANVP(127-146) | 1.82 |
| [Ala$^{130}$]rANVP(126-150) | 11.14 |
| [Asn$^{135}$]rANVP(126-150) | 33.87 |
| [D-Arg$^{133}$]rANVP(126-150) | 4.65 |
| [D-Met$^{135}$]hANVP(127-151) | 4.27 |
| [D-Asp$^{135}$]rANVP(126-150) | >40.0 | rANVP(126-150) was iodinated as described and incubated with cultured smooth muscle cells in the presence of representative peptides listed above. Various concentrations of the peptides described were examined for their ability to displace specific [$^{125}$I]-rANVP(126-150) binding. The concentration at which half-maximal displacement was observed is reported. Series A and Series B represent data from two different sets of smooth muscle cells. The relative affinities of ANVP compounds for Series B cells were consistently lower than for Series A cells.

By comparing the data in Table IV with data presented in Table III, it is apparent that relative potencies in these two biological assays are different. For example, the peptides rANVP(126-148), [Ala$^{130}$]rANVP(126-150) and rANVP(126-147) show comparable binding activity to rANVP(126-150) in smooth muscle cells. However, these peptides are substantially less potent than rANVP(126-150) in relaxing vascular smooth muscle rings (Table III). This is apparently due to the presence of multiple ANVP receptor subtypes on cells and tissues. Furthermore, there are differences in relative potencies for causing natriuresis and diuresis, as opposed to relaxing blood vessels in vivo or in vitro. This evidence indicates that various ANVPs may show selectivity towards one or more of the spectrum of biological activities induced by compounds of the present invention. It is considered desirable to provide compounds with such selectivity to obtain therapeutic benefit in treating various pathophysiological states.

Since the agonistic action of ANVP in vascular smooth muscle not only results from binding to specific receptors, but is also associated with increases in cyclic GMP (Wilquist et al., supra) the effects of ANVPs and analogs on cyclic GMP accumulation were examined using the same cultured cells. FIG. 10 demonstrates the magnitude of ANVP-mediated cyclic GMP increases in cultured aortic smooth muscle and endothelial cells. In FIG. 11A & 11B, the relative activities of ANVP compounds on cyclic GMP accumulation in aortic smooth muscle and endothelial cells are shown. The data is plotted in a dose-response relationship (log dose vs % of maximal cyclic GMP increases). The effects of other ANVP compounds on cyclic GMP accumulation in smooth muscle cells are shown in Table V.

TABLE V

Relative Potency of ANVP Compounds in Stimulating Intracellular Cyclic GMP Accumulation in Smooth Muscle Cells

| Peptide | Cyclic GMP Accumulation EC$_{50}$ (nM) |
|---|---|
| hANVP (127-151) | 15.29 |
| rANVP (126-150) | 20.89 |
| rANVP (126-149) | 5.62 |
| hANVP (127-149) | 83.18 |
| rANVP (126-148) | 426.51 |
| rANVP (126-148)NH$_2$ | 25.10 |
| rANVP (126-147) | >1000.00 |
| rANVP (126-147)NH$_2$ | 489.80 |
| hANVP (127-146) | >1000.00 |
| [D-Cys$^{129}$]rANVP (126-150) | 39.2 |
| [D-Phe$^{130}$]rANVP (126-150) | >1000.00 |
| [D-Ala$^{131}$]rANVP (126-150) | 7.43 |
| [D-Ala$^{132}$]rANVP (126-150) | 90.02 |
| [D-Arg$^{133}$]rANVP (126-150) | 500.00 |
| [D-Met$^{135}$]rANVP (127-151) | 116.1 |
| [D-Val$^{134}$]rANVP (126-150) | 420.0 |
| [D-Asp$^{135}$]rANVP (126-150) | >1000.00 |
| [D-Arg$^{136}$]rANVP (126-150) | 77.60 |
| [D-Val$^{137}$]rANVP (126-150) | 410.00 |
| [D-Ala$^{138}$]rANVP (126-150) | 114.40 |
| [D-Ala$^{139}$]rANVP (126-150) | 91.10 |
| [D-Gln$^{140}$]rANVP (126-150) | 28.40 |
| [D-Ser$^{141}$]rANVP (126-150) | 382.00 |
| [D-Ala$^{142}$]rANVP (126-150) | 14.60 |
| [D-Leu$^{143}$]rANVP (126-150) | 525.00 |
| [D-Ala$^{144}$]rANVP (126-150) | 13.70 |
| [D-Cys$^{145}$]rANVP (126-150) | >1000.00 |
| [D-Asn$^{146}$]rANVP (126-150) | 450.00 |
| [D-Ala$^{131}$][D-Ala$^{142}$]rANVP (126-150) | 2.85 |
| [Pro$^{132}$]rANVP (126-150) | 234.10 |
| [Pro$^{130}$]rANVP (126-150) | >1000.00 |
| [Ala$^{130}$]rANVP (126-150) | >1000.00 |
| [Leu$^{130}$]rANVP (126-150) | >1000.00 |
| [Ala$^{131}$]rANVP (126-150) | 22.8 |
| [Nle$^{133}$]rANVP (126-150) | 450.0 |
| [Lys$^{133}$]rANVP (126-150) | 17.0 |
| [Glu$^{135}$]rANVP (126-150) | 20.8 |
| [Asn$^{135}$]rANVP (126-150) | 320.00 |
| [Phe$^{134}$]rANVP (126-150) | 410.00 |
| [Ser$^{134}$]rANVP (126-150) | 50.00 |
| [Val$^{135}$]rANVP (126-150) | 92.0 |
| [Ala$^{133}$]rANVP (126-148) | 410.00 |
| [Ala$^{135}$]rANVP (126-150) | 472.00 |
| [Tyr$^{140}$]rANVp (126-150) | 510.00 |
| [Sar$^{132}$]rANVP (126-150) | 208.10 |

Once again, a distribution in potency over three orders of magnitude can be seen. The rank order of potency in both cell types is [D-Ala$^{131}$][D-Ala$^{142}$]rANVP(126-150)>[D-Ala$^{142}$]rANVP(-126-150)=[D-Ala$^{144}$]rANVP(126-150)=[D-Ala$^{131}$]rANVP(126-150)>rANVP(126-150)=rANVP(126-1-49)=hANVP(127-151)=rANVP(126-148)—NH$_2$.=[Ala$^{131}$]rANVP(126-150)>rANVP(127-150)-=rANVP(126-147)=hANVP(127-146). [Ala$^{130}$]rANVP(126-150), [D-Phe$^{130}$]rANVP(126-150) and [D-Asp$^{135}$]rANVP(126-150) are peptides that appear inactive in eliciting increases in cyclic GMP levels. This correlates with the diminished ability of the same peptides to relax precontracted vascular smooth muscle. This supports the hypothesis for a central role of cyclic GMP in regulating the contractile state of vascular smooth muscle. However, the lack of an apparent correlation between potency for increasing cyclic GMP and binding to all BASM associated ANVP receptor sites demonstrates that multiple ANVP receptor sites are present. The data demonstrate that certain D-amino acid substitutions increase potency, while others decrease potency. Furthermore, the data imply that removal of the Carboxy-terminal tyrosine residue has little effect on vascular reactivity, although subsequent truncations generally diminish bioactivity (except for rANVP(126-148)-NH$_2$). Furthermore, the data confirm the observation that the Amino-terminal arginine residue is important for maximal reactivity.

2. In Vivo Assays

Synthetic ANVP compounds rANVP(126-149), rANVP(126-150) and hANVP(127-151) were also found to be natriuretic in the intact rat. These compounds were administered as a bolus injection to Inactin anesthetized rats (100 mg/kg, average weight 399 g) which were maintained on a constant infusion of normal saline at 2.2 ml/hr. The results were as shown in Table VI, wherein the change in each parameter was assessed by the difference between the average of three control periods (10 mins. each) and the first experimental period (maximum response). Data are expressed as mean±SE.

TABLE VI

Natriuretic Effect of Synthetic Atrial Natriuretic/Vasodilator Peptide Compounds in Intact Rats

| Dose (μg/kg) | $\dot{V}$ (μl/min) | U$_{Na}\dot{V}$ (μEq/min) | U$_K\dot{V}$ (μEq/min) |
|---|---|---|---|
| 1.2 (n = 4) | 25.5 ± 9.7 | 2.5 ± 1.1 | 1.6 ± 0.2 |
| 2.6 (n = 4) | 41.3 ± 19.5 | 6.7 ± 4.1 | 4.4 ± 1.4 |
| 5.0 (n = 4) | 52.8 ± 6.5 | 9.1 ± 1.0 | 3.7 ± 0.5 |
| 7.2 (n = 3) | 112.0 ± 12.8 | 18.3 ± 0.5 | 3.1 ± 0.8 |

$\dot{V}$ = urine flow rate; U$_{Na}\dot{V}$ urinary sodium excretion rate; U$_K\dot{V}$ = urinary potassium excretion rate. Control values for the 15 animals were: $\dot{V}$, 10.3 ± 2.9 μl/min; U$_{Na}\dot{V}$, 0.93 ± 0.5 μEq/min; and U$_K\dot{V}$, 1.6 ± 0.4 μEq/min.

Table VII demonstrates the effects of other ANVP compounds on urinary volume and sodium excretion rates in intact rats.

TABLE VII

Natriuretic and Diuretic Effects of Synthetic ANVP Compounds in Intact Rats

| Peptide | Dose (pmol/kg) | Peak Urine Vol. (μl/min) | Peak Na$^+$ Excr. (μmol/min) |
|---|---|---|---|
| Control | — | 6 + 1 | 0.2 ± 0.1 |
| hANVP(127-151) | 460 | 83 | 15.5 |
| rANVP(126-150) | 460 | 38 ± 5 | 6.3 ± 1.2 |
| rANVP(126-148)-NH$_2$ | 460 | 44 ± 5 | 10.4 ± 1.7 |
| [D-Ala$^{132}$]rANVP(126-150) | 3670 | 89 | 20 ± 5 |
| [Pro$^{132}$]rANVP(126-150) | 3670 | 10.5 ± 2 | 56 ± 20 |
| [D-Ala$^{131}$][D-Ala$^{142}$]rANVP(126-150) | 3670 | 30 ± 7 | 140 ± 8 |
| rANVP(126-150)-NH$_2$ | 367 | 11.2 ± 1.6 | 57 ± |
| rANVP(126-147) | 488 | 4.8 ± 2.0 | 21.6 ± 7 |
| rANVP(126-148) | 455 | 6.8 ± 0.5 | 56.3 ± 8 |
| [D-Cys$^{145}$]rANVP(126-150) | 3670 | 27.3 ± 6 | 1.8 ± 0.4 |
| [D-Ala$^{142}$]rANVP(126-150) | 3670 | 66.3 ± 3 | 9.1 ± 0.9 |
| [D-Asp$^{135}$]rANVP(126-150) | 3670 | 8.5 ± 0.5 | 0.3 ± 0.1 |
| [D-Val$^{137}$]rANVP(126-150) | 3670 | 9.5 ± 5 | 0.54 ± 0.3 |
| [D-Asn$^{146}$]rANVP(126-150) | 3670 | 12.2 ± 1.2 | 1.3 ± 0.5 |

In table VII, various ANVP compounds were tested over a ten-fold range of concentration. Most of the peptides induced diuresis and natriuresis with few exceptions ([D-Asp$^{135}$]rANVP(126-150), [D-Val$^{137}$]rANVP(126-150)]). The ANVP analog, rANVP (126-147) was approximately 100x less active than rANVP (126-150) in relaxing precontracted vascular segments. However, as shown above, this analog is a potent natriuretic peptide at a dose equivalent to rANVP(126-150). this once again suggests that one can dissociate vasorelaxant actions of ANVP's from their natriuretic and diuretic properties. This is perhaps best observed with the ANVP analog [Ala$^{130}$]rANVP(1-26-150). As shown in FIG. 12$a$, which is a dose response relationship for relaxing vascular-smooth muscle, [Ala$^{130}$] rANVP is essentially inactive, while rANVP(126-150) is very potent and exhibits an EC$_{50}$ of about 3 nM. However, when one compares these two peptides (FIG. 12$b$) for their diuretic effects in vivo they are nearly equipotent. Thus, it appears that [Ala$^{130}$]rANVP(126-150), rANVP(126-147) and related peptide forms represent classes of compounds which may exert renal selectivity. Such compounds could have important therapeutic value.

Renal and hemodynamic effects have also been measured in anesthetized dogs receiving a constant infusion of the compound rANVP(126-149) (1 μg/kg bolus, followed by 0.1 μg/kg/min for 1 hour). Effects were immediately detected on blood pressure, GFR and urine flow rate and electrolyte excretion and were sustained throughout the infusion. The "experimental" data presented for these parameters in Table VII are the average values obtained during the infusion. Mean arterial pressure (MAP) fell consistently by 10-15% while GFR rose by 25-35%, in association with a sustained diuresis and natriuresis (Table VIII). The parameters returned to control (i.e. pre-infusion) levels following termination of the infusion.

TABLE VIII

Hemodynamic, Renal and Metabolic Effects Of Synthetic ANVP Compounds in Anesthetized Dogs

| | Control | Experimental | Recovery |
|---|---|---|---|
| MAP (mm Hg) | 134 ± 5 | 122 ± 4*+ | 136 ± 4 |
| GFR (ml/min) | 25.5 ± 2.7 | 32.3 ± 4.1*+ | 25.4 ± 3.3 |
| $\dot{V}$ (ml/min) | 0.21 ± 0.03 | 1.06 ± 0.14*+ | 0.37 ± 0.05 |
| FE$_{H_2O}$ (%) | 0.9 ± 0.2 | 3.4 ± 0.3* | 1.5 ± 0.2 |
| U$_{Na}\dot{V}$ (μEq/min) | 38 ± 6 | 187 ± 35*+ | 68 ± 14 |
| FE$_{Na}$ (%) | 1.1 ± 0.2 | 4.1 ± 0.5*+ | 1.9 ± 0.4 |
| U$_K\dot{V}$ (μEq/min) | 15 ± 2 | 36 ± 6*+ | 21 ± 4 |
| FE$_K$ (%) | 18 ± 1 | 34 ± 6*+ | 21 ± 4 |
| PRA (ng/ml/hr) | 13 ± 2.0 | 8.3 ± 1.8*+ | 14 ± 2.5 |
| PA (ng/100 ml) | 8.5 ± 1.9 | 5.4 ± 0.9* | 7.0 ± 1.3 |

MAP = mean arterial pressure (blood pressure); FE$_{H_2O}$ = fractional water excretion; PRA = plasma renin activity; PA = plasma aldosterone. For definition of other abbreviations see footnote to Table I. *P < 0.05 compared to control; +P < 0.05 compared to recovery.

The peptide produced significant decreases in plasma renin activity (PRA) and plasma aldosterone (PA), as shown in Table VIII. This substance also inhibits the ability of angiotensin to stimulate aldosterone production by isolated adrenal cells. Thus, ANVP compounds are able to block the effects of the renin-angiotensin system at several levels: (1) they antagonize the direct actions of angiotensin on its target organs (blood vessels and the adrenal); and (2) inhibit renin secretion, which leads to a reduced rate of angiotensin formation in the blood.

Based on the above data, it is evident that the synthetic and tissue derived ANVP compounds possess similar activity, desirably after the synthetic ANVP compounds have been allowed to oxidize to promote the formation of disulfide bridges.

It is also evident from the above results that the subject compounds can be used as potent vasorelaxant, diuretic and natriuretic agents in mammalian hosts.

IV. Expression of DNA-Derived ANVP Compounds Natriuretic/Vasodilatory Peptides

A. *Expression of pro ANVP Compounds in E. coli*

In the examples that follow, expression of DNA sequences encoding prorANVP (87-152) prorANVP (25-152), prohANVP(26-151) and prohANVP(1-02-151) in E. coli are described. It should be understood that these examples are illustrative examples, without implying any limitations, and other pre-proANVP, proANVP or ANVP compounds could be expressed in a similar manner.

1. *Construction of E. coli Expression Vector* a. Construction of pKT52 Bacterial Expression Plasmid

Generation of the trc promoter

Plasmid pEA300 (Amman, E. et al., Gene 25:167-178, 1983) was digested with PvuII and ClaI (New England Biolabs, Inc.). The digest was electrophoresed in a 0.8% agarose gel as described by Maniatis, T. et al., supra, at p. 157-160. The large fragment, containing the −35 nucleotide region of the trp promoter near the ClaI site, was detected by UV-shadowing as described by Maniatis et al., supra. at p. 167, and eluted from the gel at 37° as described by Maxam, A. and W. Gilbert, *Methods in Enzymology.* 65:449-560 (1980). The ClaI site of the large fragment was filled in with 50 μM dCTP as described in Maniatis et al., supra. at p. 394, and the remaining single-stranded 5' overhang was removed by digestion with mung bean nuclease (Pharmacia P-L Biochemicals, Inc.) as described by Kroeker, W. et al., Biochemistry 17:3236-3239 (1978).

Plasmid pGL101 (Lauer, G. et al., J. Mol. Appl. Genet. 1:139-147, 1981) was digested with PvuII and HpaII (New England Biolabs) as described. The digested fragments were filled in by the method of Maniatis et al., supra. at p. 394, with 5 units of Klenow fragment (Boehringer-Mannheim, Inc., Mannheim, FRG) and the addition of 1 μCi [γ-$^{32}$P]-dCTP (Amersham, Chicago, Ill., 800 Ci/mM) for 15 minutes at 37° C. This was followed by the addition of dCTP and dGTP to 50 μM for 30 minutes at 37° C. The labeled, blunt-ended fragments were electrophoresed on a 12% polyacrylamide gel, followed by wet gel autoradiography, and the 55 base pair blunted HpaII-PvuII fragment was cut out of and eluted from the gel as described previously. The two isolated fragments were ligated as described in Maniatis et al., supra at p. 392, and used to transform *E. coli* strain RB791 (R. Brent and M. Ptashne, Proc. Natl. Acad. Sci. USA 78:4204-4208, (1981) as described in Maniatis et al., supra, at p. 250-251.

The resulting plasmid, pKK10-0, containing the modified promoter (the trc promoter) was isolated by the rapid boiling method as described in Maniatis et al., supra. at pp. 366-367. PKK10-0 was digested with EcoRI (Bethesda Research Labs, Inc.), and used to transform *E. coli* RB791 as described above. This plasmid, termed PKK10-1, was isolated as described and digested with PvuII. The PvuII digested plasmid was ligated to the NcoI linker (dACCATGGT, Creative Biomolecules, Inc. Foster City, Calif.), digested with NcoI, filled in with dATP, dCTP, dGTP, and dTTP, and ligated, as described previously, to a linker containing PstI and HindIII sites synthesized as two complementary oligonucleotides (5'-dGCTGCAGCCAAGCTTGG-3' and 5'dCCAAGCTTGGCTGCAGC-3') on a Biosearch SAM I DNA Synthesizer (Biosearch, Inc., San Rafael, Calif.). The ligation mixture was digested with BamHI and HindIII (New England Biolabs), electrophoresed on a 5% polyacrylamide gel, and the small BamHI - HindIII fragment was eluted as described above. This fragment contains the trc promoter.

ii) Construction of the trc promoter plasmid, pKT52

PKK10-2 (Brosius, J., Gene 27:161-172, 1984) was digested with BamHI and HindIII. The large fragment was isolated from a 0.8% agarose gel and ligated to the trc promoter fragment described above. The ligation was used to transform E. coli RB791 and the new plasmid, pKK233-1, was isolated as described previously.

PKK233-1 was digested to completion with PvuI and partially digested with BolI, in accordance with Maniatis et al., supra, at p. 381. At the same time, pUC8 (Vieira, J. and J. Messing, Gene 19, supra) was digested with PvuI and BglI and the 360 base pair PvuI-BglI fragment from the ampicillin resistance gene (that no longer contains a PstI site) was isolated from a 5% polyacrylamide gel. This fragment was mixed with the PvuI-BglI partial digestion mix of pKK233-1, ligated and used to transform *E. coli* RB791. Transformants were screened for the presence of only one PstI site and checked with a EcoRI-PstI digestion such that the remaining PstI site was next to the trc promoter, thereby generating plasmid pKK233-2. Plasmid pKK233-2 was then digested with EcoRI and PvuII, filled in with dATP and TTP, ligated, and transformed into *E. coli* RB791. The resulting vector is termed pKT52 (FIG. 12A).

b. Construction of pTrp-233 Bacterial Expression Plasmid i) Construction of the synthetic tryptophan operon promoter and operator regulatory sequence The ten oligodeoxynucleotides shown in FIG. 13E were synthesized and purified as described above. 500 pmole of each oligodeoxynucleotide except 1 and 10 were phosphorylated individually in 20 μl containing 60 mM Tris-Cl, pH 8, 15 mM DTT, 10 mM MgCl$_2$, 20 μCi of [γ$^{32}$P]-ATP and 20 units of polynucleotide kinase (P/L Biochemicals) for 30 min. at 37° C. This was followed by the addition of 10 μl containing 60 mM Tris-HCl, pH 8, 15 mM dithio treated (DTT), 10 mM MgCl$_2$, 1.5 mM ATP and 20 additional units of polynucleotide kinase, followed by another 30 min. incubation at 37° C. After incubation, the samples were then incubated at 100° C for 5 min. 500 pmole of oligodeoxynucleotides 1 and 10 (FIG. 13E) were diluted to 30 μl in the above buffer without ATP.

16.7 pmole of each oligodeoxynucleotide constituting a double standard pair (e.g. oligodeoxynucleotides 1 and 2, 3 and 4 etc. (FIG. 13E)) were mixed and incubated at 90° C. for 2 min. followed by slow cooling to room temperature. Each pair was then combined with the others in the construction and the mixture was extracted with phenol/chloroform followed by ethanol precipitation. The oligodeoxynucleotide pairs were reconstituted in 30 μl containing 5 mM Tris-HCl, pH 8, 10 mM MgCl$_2$, 20 mM DTT, heated to 50° C. for 10 min. and allowed to cool to room temperature. ATP was then added to a final concentration of 0.5 mM, followed by the addition of 800 units of T4 DNA ligase and incubation at 12.5° C. for 12–16 hours.

The ligation mixture was extracted with phenol/chloroform and the DNA was precipitated with ethanol. The dried DNA was reconstituted in 30 μl and digested with EcoRI and PstI for 1 hour at 37° C. The mixture was extracted with phenol/chloroform and ethanol precipitated. The various double stranded DNA segments were separated by electrophoresis on an 8% polyacrylamide gel, as described previously. The DNA fragments were visualized by wet gel autoradiography and a band corresponding to approximately 100 bp in length was cut out and eluted overnight as described above. The excised synthetic DNA fragment was ligated to plasmids M13-mp8 and M13-mp9 (Messing, J. and Vieria, J., supra) similarly digested with EcoRI and PstI and submitted to dideoxynucleotide sequence analysis (Sanger et al., supra) to confirm the designed sequence shown in FIG. 13E. This sequence contains the promoter and operator regions of the tryptophan operon (trp) (-35 and -10 regions) as well as the ribosome binding region (S.D. region in FIG. 13E) of the tryptophan operon leader peptide. Analagous sequences to that shown in FIG. 13E have been proven to be useful in the expression of heterologous proteins in E. coli (Hallewell, R. A. and Emtage, S., Gene 9:27–47 (1980); Ikehara, M. et al., Proc. Natl. Acad. Sci. USA 81:5956-5960 (1984)).

ii) Construction of the Synthetic trp Promoter/Operator Containing Plasmid pTro-233

Plasmid PKK233-2 (see Section IV.A.1.a.ii.) was digested to completion with NdeI, followed by the filling in of the termini by the method of Maniatis et al., supra, at p. 394, with 5 units of E. coli polymerase I, Klenow fragment (Boehringer-Mannheim, Inc.) and the addition of dATP, dCTP, dGTP and TTP to 50 μM. This mixture was incubated at 25° C. for 20 min. Following phenol/chloroform extraction and ethanol precipitation, NdeI digested DNA was ligated and transformed into E. coli (Nakamura, K. et al. supra). The resulting plasmid, lacking the NdeI site, was designated pKK-233-2-Nde.

Twenty ng of plasmid pKK-233-2-Nde was digested to completion with EcoRI and PstI, followed by calf intestinal phosphatase treatment (Boehringer Mannheim) in accordance with Maniatis et al., supra, at pp. 133-134. Fifty ng of the synthetic trp promoter/operator sequence, described above, with its cohesive 5'-EcoRI and 3'-PstI- termini were mixed with ten ng of EcoRI - P=+T digested pKK-233-2-Nde and ligated with T4-DNA ligase, as described above, followed by transformation into E. coli strain JA221 (1pp−/I'lacI⁹).

Transformants, screened for the presence of asmid DNA containing the 100 bp EcoRI–PstI synthetic trp promoter/operator, were isolated and designated pTRP-233 (shown in FIG. 13F).

2. Expression of Cloned cDNA Encoding Rat Pro ANVP Compounds a) Construction cf Plasmid pRNF-6852

Plasmid pNF1 (see Section II.A.3) was digested to completion with HincII followed by extraction with phenol/chloroform and ethanol precipitation. An NcoI decamer linker (dAGCCATCGCT) was synthesized on a SAM I DNA Synthesizer (Biosearch, Inc.), purified by preparative gel electrophoresis as described above and phosphorylated at the 5' end with T4-polynucleotide kinase (P-L Biochemicals) using the procedure of Maniatis et al., supra, at p. 396. The phosphorylated linker was attached to HincII digested pNF1 by blunt-end ligation with T4-DNA ligase at 12.5° C. for 16 hrs.

Following incubation at 65° C. for 5 min., the ligation mixture was adjusted to 100 mM NaCl and incubated for 2 hrs. at 37° C. with NcoI and PstI, followed by 5% polyacrylamide gel electrophoresis as described previously. The separated DNA was visualized by wet gel autoradiography, followed by excision of a 316 bp band, elution and ethanol precipitation as described above (Maxam, A. and W. Gilbert, supra).

The expression plasmid, pKT52 was digested to completion with NcoI and PstI, followed by calf intestinal phosphatase (Boehringer Mannheim) treatment, in accordance with Maniatis et al., supra, at pp. 133-134. The purified 316 bp NcoI-PstI fragment, derived from pNF1, was mixed with NcoI-PstI digested pKT52 and incubated with T4-DNA ligase for 30 min. at 25° C. and 4 hours at 12.5° C. E. coli strain JA221 (1pp−, hsd M+, trpE5, leuB6, lacY, recAl/F', lacIq, lacZ+, proA+, proB+ (Nakamura, K. et al., J. Mol. Appl. Genet. 1:289–299 (1982))) was made competent for transformation by the CaCl₂ method and transformed with the ligation mixture, as described in Maniatis et al., supra. at pp. 250–251. Resulting ampicillin resistant colonies were grown overnight in 1 ml, from which plasmid DNA was prepared by the alkaline lysis method (Maniatis et al., supra. at pp. 368–369). Plasmids were screened for the correct insert by digestion first with HindIII, followed by KpnI or NcoI. A plasmid having both HindIII-KonI and HindIII-NcoI fragments, of approximately 120 bp and 320 bp respectively, was chosen and designated pRNF-6852 (FIG. 13B).

To confirm that the reading frame of the cloned proANVP sequence in pKT-52 was correct, pRNF-6852 was digested with EcoRI and PstI, followed by purification of a band of approximately 509 bp by polyacrylamide gel electrophoresis as described above. The EcoRI-PstI fragment was ligated to plasmids M13-mp8 and M13-mp9 (Messing, J. and J. Vieria, supra) and submitted to dideoxynucleotide sequence analysis (Sanger et al., supra).

As shown in FIG. 13B, plasmid pRNF-6852 was designed to express a fragment of the rat proANVP cDNA which encodes a protein from amino acids 87 to 152 (see FIG. 1). Because a synthetic decamer NcoI linker was used, to allow cloning of the proANVP cDNA into the expression vector pKT52, the first two Amino-terminal amino acids of the expressed fragment are Met-Ala, followed by amino acids 87 through 152 of the rat proANVP precursor (FIG. 13B).

b) Expression of Plasmid pRNF-6852

E. coli JA221 (1pp−/F' lacIq) containing pRNF-6852 or pKT52 were grown at 37° C. in media containing M9 minimal salts (Miller, J., *Experiments in Molecular Genetics*, Cold Spring Harbor Laboratory, Cold Spring Harbor, N.Y.) supplemented with glucose (0.4%), thiamine (2 μg/ml), MgSO₄.7H₂O (200 μg/ml), leucine (20 μg/ml), tryptophan (20 μg/ml), ampicillin (100 μg/ml), and isopropyl-1-thio-β-D-galactopyranoside (2 mM). At a cell density of approximately 2.5×10⁸ cells/ml, L-[³⁵S]-cysteine (100 μCi/ml culture (Amersham Corp., Chicago, Ill., 930 Ci/mmole)), was added. Following 30 sec. of incubation, 1 ml of culture was removed and added to 0.34 ml of ice-cold 20% trichloroacetic acid in a 1.5 ml Eppendorf centrifuge tube, vortexed and allowed to stand at 0° C. for 30 min. The mixture was then certrifuged at 4° C. for 15 min in an Eppendorf centrifuge at 15,000×g. The supernatant was discarded and the pellet was washed with 1 ml of ice-cold acetone, followed by centrifugation and drying of the resulting pellet in vacuo.

An IgG fraction was prepared from 1 ml of non-immune serum or anti-serum (raised against a chemically synthesized rat ANVP peptide) using Protein A-Sepharose ® 4B chromatography as described in the manufacturer's specifications (Pharmacia Fine Chemicals, Uppsala, Sweden) and collected in a total volume of 4 ml.

The dried TCA pellet was resuspended in 40 µl of 50 mM Tris-HCl, pH 8.0, 1 mM EDTA, 1% SDS and incubated at 100° C. for 5 min. Ten µl of this mixture (representing total bacterial protein) was diluted to 20 µl with 20 mM Tris-HCl, pH 6.8, 22% glycerol, 2% SDS, 2% β-mercaptoethanol, 0.1% bromphenol blue, followed by incubation at 100° C. for 5 min. The remaining 30 µl (used for immunoabsorption) of the mixture was diluted to 1 ml with 50 mM Tris-HCl, pH 8.0, 1 mM EDTA, 0.15 M NaCl, 2% Triton X-100 ®, followed the addition of 40 µl of purified IgG derived from non-immune serum or antiserum raised against rat ANVP. The mixture was incubated at room temperature for 30 min and 4° C. overnight.

Following the overnight incubation, 50 µl of Protein A-Sepharose ® 4B (10% suspension in 50 mM Tris-HCl, pH 7.5, 5 mM EDTA, 0.15 M NaCl, 0.5% Nonidet P-40 ((NP-40) Sigma Chemical Co., St. Louis, Mo.), 1 mg/ml ovalbumin) was added to the mixture and incubated at 4° C. for 1 hr with gentle agitation. Following centrifugation at 4° C., the supernatant was discarded and the Protein A-Sepharose ® pellet was resuspended in 0.5 ml of 50 mM Tris-HCl, pH 7.5, 5 mM EDTA, 0.5 M NaCl, 0.5% NP-40, 1 mg/ml ovalbumin. The pellet was washed by vigorous vortexing, followed by centrifugation and removal of the supernatant.

This procedure was repeated four additional times. The Protein A-Sepharose ® pellet was washed an additional two times with 50 mM Tris-HCl, pH 7.5, 5 mM EDTA, 0.15 M NaCl and 0.5% NP-40, followed by one wash with 10 mM Tris-HCl, pH 7.5. Following drying in vacuo, the pellet was resuspended in 60 µl of 10 mM Tris-HCl, pH 6.8, 1% glycerol, 1% SDS, 1% β-mercaptoethanol, 0.05% bromphenol blue, followed by incubation at 100° C. for 10 min.

The total and immunoabsorbed samples were subjected to discontinuous SDS-polyacrylamide gel electrophoresis as described by Anderson, C.W. et al., J. Virol. 12:241-252 (1973) on a 130×200×0.8 mm polyacrylamide slab gel containing 17.5% acrylamide, 0.0735% bis-acrylamide, 0.335 M Tris-HCl, pH 8.7, 0.04 M NaCl, 0.1% SDS, 0.05% ammonium persulfate, 0.05% TEMED. The samples were run at 30 mA constant current until the bromphenol blue dye reached the bottom of the gel. The separated proteins were fixed in the gel by shaking in a solution of 25% isopropyl alcohol, 10% acetic acid, and 0.12 mg/ml Brilliant Blue R-250 (Sigma Chemical Co., St. Louis, MO) for 1 hr at room temperature, followed by overnight incubation in a solution of 10% isopropyl alcohol, 10% acetic acid, and 0.12 mg/ml Brilliant Blue R-250. Following destaining with 10% acetic acid over a period of 3 hours with several changes, the gel was treated with En3-Hance (trade name) (New England Nuclear, Boston, Mass.) according to the manufacturer's directions, followed by drying and fluorography at −70° C. using Kodak ® XAR-5 x-ray film.

A comparison of the peptide patterns from cells containing plasmids pKT-52 or pRNF-6852, labeled with L-[$^{35}$S]-cysteine as described above, is shown in FIG. 14. A peptide with an approximate molecular size of 6200 daltons appears uniquely in lane C, which represents the total peptides derived from pRNF-6852. This peptide is specifically immunoreactive only to anti-ANVP IgG (lane D). In addition, there was no detectable reaction of anti-ANVP IgG with any peptide derived from pKT-52 (lane B). Thus, it was demonstrated that the predicted fragment of proANVP was expressed in cells containing the plasmid pRNF-6852.

E. coli strain JA221 (1pp$^-$F' lacI$^q$) containing pRNF-6852 was deposited with the American Type Culture Collection (ATCC) 12301 Parklawn Drive, Rockville, Md. 20852 on May 31, 1984 and accorded the accession number 39720.

3. Expression of Cloned cDNA Encoding Rat proANVP (26-152)

a. Construction of plasmid pRNF12852

In a manner similar to that described in Section IV. C.2, full length rat proANVP was expressed. To accomplish this, plasmid pNFl (see above) was digested to completion with AccI, followed by ethanol precipitation. The AccI-digested DNA was mixed with the synthetic double-stranded DNA linker

which had been synthesized on a SAM I DNA synthesizer (Biosearch Inc.) and purified by preparative gel electrophoresis as described above. T4-DNA ligase was added to this mixture to ligate the linker onto the digestion products.

Digestion of the ligation mixture with HinfI yielded a 627 bp DNA fragment which was purified by 5% polyacrylamide gel electrophoresis and eluted. The purified 627 bp HinfI-fragment was treated with Klenow fragment and digested with PstI, followed by ethanol precipitation. Plasmid pKT52 was digested with NcoI, followed by treatment with Klenow enzyme, PstI digestion and calf intestinal alkaline phosphatase treatment as described (Maniatis, et al., supra. at pp. 133-134). The HinfI-PstI digested pNFI fragment was then mixed with NcoI-PstI digested pKT52 and ligated using T4-DNA ligase.

Following transformation of JA221 (1pp$^-$/F'lacIq) with the ligation mixture, mini-preps of plasmids derived from the resulting ampicillin resistant colonies were screened for the correct insert by digestion with HindIII, followed by KpnI or HincII digestion.

A plasmid having both HindIII - KonI and HindTTT -HincII fragments, of approximately 120 bp and 312 bp respectively, was chosen and designated pRNF-12852. The reading frame of the cloned full length rat proANVP sequence in pKT52 was confirmed by dideoxynucleotide sequence analysis (Sanger, et al., supra).

Plasmid pRNF-12852 (FIG. 13D) encodes a protein encompassing residues 25 through 152 of the rat proANVP precursor with the additional methionine codon ATG preceding the codon AAT, which corresponds to amino acid residue 25.

b. Expression of plasmid pRNF-12852

E. coli JA221 (lpp⁻/F'lacIq) containing pRNF-12852 or pKT52 were grown at 37° C. and labeled with L-[³⁵S]-cysteine as described in Section IV.A.2.b. Following immunoabsorption with anti-ANVP IgG, the labeled total and immunoabsorbed peptides were separated by SDS-polyacrylamide gel electrophoresis and submitted to autoradiography as described previously.

A comparison of the peptide patterns from cells containing plasmids pKT-52 or pRNF-12852, labeled with L-[³⁵S]-cysteine as described above is shown in FIG. 4, lanes A and E, respectively. One major peptide species, with an approximate molecular size of 18,400 daltons, appear uniquely in lane E (marked by arrows) which contained the total peptides derived from pRNF12852. This peptide species was specifically immunoreactive only to anti-ANVP IgG, whereas there was no detectable reaction of immune IgG; with any peptide derived from pKT-52 (compare lanes B and F in FIG. 14). The 18,400 dalton peptide observed in FIG. 14F is believed to be rat proANVP starting at amino acid 25 following an initiator methionine as shown in FIG. 13D.

4. Expression of Human proANVP(102-151)

The plasmid pHGRBl, containing the human genomic DNA, was digested to completion with ApaI, followed by T4-DNA polymerase treatment (Maniatis et al., supra, at p. 395) to blunt the 3'-extended termini A synthetic HindIII linker (pCAAGCTTG, Collaborative Research Inc , Lexington, Mass.) was attached to the blunt-ended human genomic DNA through blunt-end ligation as described above. The ligation mixture was then digested with HindIII and NcoI, followed by the isolation of a 272 bp HindIII-NcoI fragment using 5% polyacrylamide gel electrophoresis and elution. The 272bp HindIII-NcoI fragment was mixed with HindIII-NcoI digested pBR329 (Covarrubias, L. and F. Bolivar, Gene 17:79-89 (1982)) and treated with T4-DNA ligase. The resulting plasmid pHNF-298 was digested with BamHI and NcoI and the resulting 620 bp NcoI-BamHI fragment purified by agarose gel electrophoresis. The 620 bp NcoI-BamHI fragment was digested to completion with MsoI followed by repair of the 5'extended termini by E. coli DNA polymerase I (Klenow fragment). The synthetic HindIII linker pTTACTAAGCTTAGTAA was synthesized, purified and phosphorylated and attached to the MsoI digested NcoI-BamHI fragment through blunt-end ligation.

The ligation mixture was then digested with HindIII, followed by the isolation cf an 156 bp HindIII fragment by 5% polyacrylamide gel electrophoresis. The 156 bp HindIII fragment was attached to pKT52, which had been digested with HindIII and treated with calf intestinal alkaline phosphatase using T4-DNA ligase as described previously.

Following transformation of JA221 (1pp⁻/F'lacIq) with the ligation mixture, mini-preps of plasmids derived from the resulting ampicillin resistant colonies, were screened for the correct insert by digestion with NcoI, followed by ClaI digestion.

A plasmid having an NcoI-ClaI insert of 150 bp was chosen and designated pHNF-5752. The reading frame of the cloned human proANVP sequence in pKT52 was confirmed by DNA sequence analysis as described above.

Because a synthetic HindIII 8-mer linker was used to allow cloning of the proANVP cDNA fragment into the HindIII site of pKT52, the amino acids preceding the proANVP sequence are Met-Ala-Ala-Ala-Lys-Leu-Ala. In addition, the synthetic HindIII 16-mer linker was used to reconstruct the Carboxy-terminal amino acid residues Arg and Tyr. Therefore, the sequence of the expressed human proANVP fragment was determined to be:

| NH₂ | Met | ala | Ala | Ala | Lys | Leu | Ala | Trp | Asp | Ser |
|---|---|---|---|---|---|---|---|---|---|---|
| Ser | Asp | Arg | Ser | Ala | Leu | Leu | Lys | Ser | Lys | Leu |
| Arg | Ala | Leu | Leu | Thr | Ala | Pro | Arg | Ser | Leu | Arg |
| Arg | Ser | Ser | Cys | Phe | Gly | Gly | Arg | Met | Asp | Arg |
| Ile | Gly | Ala | Gln | Ser | Gly | Leu | Gly | Cys | Asn | Ser |
| Phe | Arg | Tyr | COOH | | | | | | | | using dideoxynucleotide sequence analysis as described (Sanger et al., supra).

5. Expression of Cloned cDNA Encoding Human proANVP(26-151)

a. Construction of Plasmid phNF-233

λ-phage DNA from clone 6, containing the human ANVP cDNA (Section II.C), was digested with EcoRI, followed by the isolation of a 713 bp fragment using polyacrylamide gel electrophoresis and elution. The purified EcoRI fragment was ligated to similarly digested plasmid pUC-9 (Vieira, J. and Messing, J., Gene 19, supra) followed by transformation into E. coli as described. A plasmid with an appropriate 713 bp EcoRI fragment was isolated and designated phNF-pUC-1. Plasmid phNF-pUC-1 was digested to completion with RsaI followed by phenol/chloroform extraction and ethanol precipitation.

The RsaI digested DNA was mixed with the synthetic double stranded DNA linker

which had been synthesized and purified as described above, followed by the addition of T4-DNA ligase to ligate the linker onto the RsaI digestion products. Digestion of the ligation mixture with NdeI yielded a 370 bp DNA fragment which was purified by polyacrylamide gel electrophoresis and eluted. Plasmid pUC-19 (Vieria, J. & Messing, J. supra) was digested with NdeI and treated with calf intestinal phosphatase, followed by phenol/chloroform extraction and ethanol precipitation. The 370 bp DNA fragment described above was ligated onto the NdeI digested pUC-19, followed by transformation of E. coli The screening of transformants resulted in a plasmid containing the 370 bp NdeI human proANVP cDNA sequence, which was chosen and designated phNF-pUC-2. phNF-pUC-2 was digested with ApaI and EcoRI, followed by isolation of the larger sequence by agarose gel electrophoresis, as described above. Plasmid phNF-pUC-1 was also digested with ApaI and EcoRI, followed by the isolation of a 442 bp sequence by polyacrylamide gel electrophoresis and elution. The 442 bp ApaI-EcoRI fragment derived from phNF-pUC-1 was ligated onto ApaI-EcoRI digested phNF-pUC-2, followed by transformation of E. coli. The resulting transformants were screened by digestion with NdeI and PstI which yielded a plasmid containing a 517 bp NdeI-PstI fragment. This plasmid was isolated and designated phNF-pUC-3.

The expression plasmid pTRP-233 (FIG. 13F) was digested to completion with NdeI and PstI, followed by calf-intestinal phosphatase treatment, as previously described. Plasmid phNF-pUC-3 was digested to completion with NdeI and PstI, followed by the isolation of a 517bp DNA sequence by polyacrylamide gel electrophoresis and elution. The NdeI-PstI fragment derived from phNF-pUC-3 was ligated to NdeI-PstI digested pTRP-233, followed by transformation of E. coli. The resulting plasmid containing the 517bp NdeI-PstI fragment in pTRP233 was isolated and designated phNF-233 (FIG. 13G). To confirm the fidelity of the trp promoter/operator sequence, as well as the reading frame of cloned human proANVP sequence in pTRP-233, phNF-233 was digested with EcoRI and PstI, followed by the isolation of the DNA sequence by polyacrylamide gel electrophoresis and elution. This fragment was ligated to plasmid M13-mp18 (Messing, J. and Vieria, J., supra) and submitted to dideoxynucleotide sequence analysis ,Sanger et al., supra).

As shown in FIG. 13G, plasmid phNF-233 was designed to express full length human proANVP encompassing residues 26 through 151 of the human pre-proANVP compound, with an additional methionine codon, ATG, preceeding the codon AAT, which corresponds to residue 26.

b. Expression of Cloned Full length Human proANVP (26-151) cDNA in phNF-233

E. coli E103S (Hfr, MetB, lacI$^{ts}$), containing phNF-233 or pTRP-233, were grown overnight at 37° C. in Luria-Bertani medium (Maniatis et al., supra, at p. 68) supplemented with ampicilin (100 [g/ml). The resultant cultures were diluted 1:100 in media containing M9 minimal salts (Miller, J., supra) supplemented with glucose (0.4%), thiamine (2 μg/ml), MgSO4 7H2O (200 μg/ml), Casamino acids (0.5%) and ampicillin (100 μg/ml) and grown at 37° C. until the cell density reached an $A_{550}$ of 0.1, at which time 3-β-indoleacrylic acid (Sigma Chemical Co.) was added from a 10 mg/ml ethanolic solution to a final concentration of 25 μg/ml. At an $A_{550}$ of 0.50, L-[$^{35}$S]-cysteine (200 μCi/ml culture (New England Nuclear)) was added and incubation continued for 1 min. One ml of culture was removed at this time and added to 340 μl of ice-cold 20% trichloroacetic acid and treated as described in section IV.A.2.

Immunoabsorption of L-[$^{35}$S]-cysteine-labeled peptides derived from cells containing phNF-233 or pTRP-233 was accomplished as described in Section IV.A.2. using antisera raised in rabbits challenged with synthetic rat ANVP (127-152).

Total and immunoabsorbed L-[$^{35}$S]-cysteine-labeled peptides were analyzed by SDS-polyacrylamide gel electrophoresis and fluorography as described in Section IV.A.2. A comparison of the peptide patterns from cells containing plasmids pTRP-233 or phNF-233 labeled with L-[$^{35}$S]-cysteine is shown in FIG. 15. A major peptide species, with an approximate molecular weight of 18,000 daltons, appears uniquely in lane B, which represents the total peptides derived from phNF-233, as compared to lane A which represents total peptides derived from pTRP-233. This 18,000 dalton peptide is specifically immunoreactive to anti-ANVP antisera whereas immunoreaction with peptides derived from pTRP-233 was not detected (compare lanes C and D in FIG. 15). The predicted peptide of human pro-ANVP (26-151) was therefore expressed in cells containing the specific plasmid phNF-233.

E. coli strain K12 E103S Hfr Cavalli, met B, lacI$^{ts}$ containing pRNF-6852 was deposited with the American Type Culture Collection (ATCC) 53085 Parklawn Drive, Rockville, MD 20852 on April 9, 1985 and accorded the accession number 53085.

c. Purification and Characterization of Human pro-ANVP(26-151) from E. coli

E. coli E103S containing phNF-233 were grown in Luria-Bertani media supplemented with ampicillin (100 μg/ml) at 37° C. overnight. Ten ml of the culture was diluted into 1000 ml of media containing minimal salts and supplements as described in Section IV.A.5.b and grown at 37° C. to a cell density corresponding to 0.1 $A^{550}$. At this time, 3-β-indoleacrylic acid was added from a 10 mg/ml ethanolic solution to a final concentration of 25 μg/ml. The cells were allowed to grow until a cell density corresponding to 1.0 $A_{550}$ was reached, at which time the cells were collected by centrifugation at 7,000 rpm at 4° C. The cell pellets were resuspended in an ice-cold solution of 10 mM Tris-HCl, pH 8, and centrifuged as before. The washed cell pellet was resuspended in 40 ml of an aqueous solution containing 1 M acetic acid and 20 mM HCl. The cells were disrupted using a Heat Systems-Ultrasonics Inc. Model W-225-R sonicater at 0° C. The lysed suspension was then incubated in a closed container in a boiling water bath for 5 min., followed by centrifugation at 12,000 rpm at 4° C. for 20 min. The supernatant (termed acid extract) was removed and applied to a 2.5 cm × 100 cm column containing Sephadex ® G-10 (Pharmacia) which had been equilibrated with 10 mM Tris-HCl, pH 7.5 and 1 mM EDTA. The resulting immunoreactive fractions, as detected by a specific ANVP radioimmunoassay (see Section V), were pooled and lyophilized. The dried fractions were resuspended in 0.5 M acetic acid and applied to a 2.5 × 50 cm column containing Sephadex ® G-10, previously equilibrated in 0.5 M acetic acid.

Resulting immunoreactive column fractions were pooled and lyophilized. The dried material was brought up in approximately 4 ml of distilled water and submitted to high performance liquid chromatography (HPLC) purification. The material was applied to a 1 × 25 centimeter Vydac C18 column (Vydac 218TPIO10) using a Perkin-Elmer Series 4 LC injector and solvent delivery system (Perkin-Elmer). The bound material was washed for 2 minutes with aqueous 15% acetonitrile (CH3CN) and 0.1% trifluoroacetic acid (TFA), followed by the development of a linear gradient of CH3CN and 0.1% TFA from 15:85 to 60:40 over 45 minutes. Aliquots from 1 minute fractions were collected and portions were dried and assayed for immunoreactivity, using an anti-ANVP radioimmunoassay as described above. The peak of immunoreactivity was subsequently collected and dried in vacuo. The dried material was resuspended in water and dried again by lyophilization.

One hundred pmoles of this material was submitted to automated amino acid sequence analysis using a Model 470A protein sequenator (Applied Biosystems Inc., Foster City, Calif.). The first 18 amino acids analyzed were:

Met-Asn-Pro-Met-Tyr-Asn-Ala-Val-Ser-Asn-Ala-AspLeu-Met-Asp-Phe-Lys-Asn

No other detectable impurities could be observed from this analysis.

SDS-polyacrylamide gel analysis, as described in section IV.2.b, also revealed no other detectable impurities of the purified material, which migrated with an apparent molecular size of 18,000 daltons. From the sequence analysis of this peptide, described above, it was demonstrated that this peptide corresponds to full length human pro-ANVP(26-151), with an additional Amino-terminal methionine, and contains no detectable contamination from bacterial peptides.

B. Expression of ProANVP and Pre-proANVP Compounds in *Saccharomyces cerevisiae*

In the examples that follow, the expression of various proANVP and ANVP compounds in *S. cerevisiae* are described. In a similar manner, any proANVP or ANVP sequence can be expressed in *S. cerevisiae*.

1. Intracellular Expression

Two procedures are disclosed for the preparation of vectors for intracellular expression in the yeast *Saccharomyces cerevisiae* of cDNA encoding pre-proANVP, proANVP and ANVP compounds. Each procedure utilizes the strong promoter sequence found in front of the yeast phosphoglycerate kinase (PGK) gene.

For the first procedure, the plasmid pNF1 was digested with HincII (New England Biolabs). BamHI linker oligonucleotides (8 nucleotides in length, Collaborative Research, Inc.) were ligated onto the digestion products, and the resulting molecules were digested with BamHI. The 454 bp fragment from this digest, containing the rat ANVP(126-150) sequence was then purified by 5% polyacrylamide gel electrophoresis and ligated into the BamHI site of the yeast —*E. coli* vector pYPGK2.

This vector was constructed by digesting the yeast—*E. coli* shuttle vector YEp13 (J. (roach et al., Gene 8:121-133 (1979)) with the restriction enzymes BamHI and HindIII, and then ligating the largest of the restriction fragments thus obtained to a restriction fragment spanning the promoter region from the yeast PGK gene. The PGK promoter-containing fragment extends from a HindIII restriction site, approximately 1500 base pairs upstream from the ATG start codon of PGK, to a BamHI linker oligonucleotide (8 base pairs in length, Collaborative Research,. Inc.) inserted 28 base pairs downstream from the ATG start codon after BAL-31 digestion from within the PGK coding region.

Using the vector pYPGK2, any sequence of DNA in the pre-proANVP coding sequence can be inserted and used to express a desired portion of pre-proANVP. For example, insertion of the 454 bp ANVP-containing fragment into the BamHI linker site in this vector in the correct orientation allows the synthesis of a 78 amino acid long fusion protein from the PGK promoter (consisting of 9 amino acids from the amino terminus of the PKG gene, 3 amino acids coded for by the linker oligonucleotide, 39 amino acids of the pro-ANVP region, the 25 amino acids of the mature ANVP sequence, and the two arginine residues of the carboxy terminus of the ANVP precursor).

A second procedure for intracellular expression of pre-proANVP compounds also allows extracellular secretion of proANVP compounds. In the second procedure, a restriction fragment containing the entire pre-proANVP precursor coding region is isolated from the plasmid pNF4 by first digesting the plasmid with the restriction enzyme SalI (New England Biolabs). The single-stranded regions on the ends of the resulting linear length plasmid molecules are made doublestranded by treatment with DNA polymerase I (Klenow fragment), and BamHI linkers (8 nucleotides in length, Collaborative Research, Inc.) are then ligated on to these blunt ends. The linear plasmid molecules are then digested with BamHI and EcoRI, and the approximately 900 bp BamHI (SalI) - EcoRI fragment containing the pre-proANVP sequence is isolated.

The fragment is ligated into a vector identical to the pYPGK2 vector described above, with two modifications: (1) the BamHI linker oligonucleotide lies 23 bp upstream from (5' to) the ATG codon of PGK, and (2) the cloned cDNA fragment is followed by the transcription termination regin of the PGK gene (EcoRI-—HindIII fragment containing the 3' end of the PGK locus, plus the 346 bp HindIII—BamHI fragment from pBR322 as a 3' linker).

Expression of the inserted pre-proANVP cDNA from the PGK promoter results in the synthesis of pre-proANVP compounds. The expressed pre-proANVP compound will be processed and secreted by the yeast cell if the signal and/or processing sites are recognized as such by the cell and acted upon. The material so secreted will be either proANVP, fragments thereof or ANVP compounds alone. If recognition of the signal sequence does not occur, the full-length pre-proANVP compounds, or fragments thereof, will be found internally in the cells.

2. Extracellular Expression a) Construction of YEp-α-8 Expression Vector

A yeast library in the *E. coli* shuttle vector YEp13 (Nasmyth, K. and K. Tatchell, Cell 19:753-764 (1980)) was screened using a 5'-[=P] end-labeled oligodeoxynucleotide (5'-CCTGGCCAACCAATG-3'), (see Maniatis et al., supra, at pp. 324–325). Plasmids containing inserts of yeast DNA hybridizing to this oligonucleotide were subsequently isolated. One of these plasmids contained an insert of approximately 15 kb of yeast DNA, and was shown to contain the 1.7 kb EcoRI fragment containing the α-factor gene, as described by Kurjan, J. and I. Herskowitz, Cell 30:933-943 (1982).

The ends of the 1.7 kb EcoRI fragment were made blunt by incubation with DNA polymerase I (Klenow fragment) and BamHI linkers were attached using T4-DNA ligase (Maniatis et al., supra, at pp. 113–114, 116, 392–394). The BamHI ends were made cohesive by digestion with BamHI, and subsequently ligated into the BamHI site of the *E. coli* shuttle plasmid pCV7-HinΔ 228. A deletion around the HindIII site of the plasmid CV7 was made by HindIII digestion, treatment with exonuclease III, treatment with S1-nuclease, and religation with T4-DNA ligase to generate the plasmid pCV7-HinΔ228, all using the method described in Broach, J. R. and J. B. Hicks, Cell 21:501-508 (1980). This plasmid containing the yeast α-factor gene is diagrammed in FIG. 16, and henceforth referred to as YEp-α-8.

b) Insertion of cDNA Coding for Rat proANVP Compounds into YEp-α-8

Two fragments of DNA from pNF1 (Section II.A.3.) encoding pre-proANVP were inserted into the unique HindIII site of YEp-α-8 (FIG. 16) by restriction endonuclease cleavage, filling in the ends of DNA with DNA polymerase I (Klenow fragment) as necessary and adding HindIII linkers (Maniatis et al., supra, at p. 392). The ends of the DNA fragments were subsequently made cohesive by digestion with HindIII, and ligated into HindIII cleaved YEp-α-8, which had been treated with alkaline phosphatase (see Maniatis et al., supra, at pp. 133-134). Recombinant molecules were transformed into *E. coli* and colonies analyzed for plasmid DNA (Maniatis et al., supra. at pp. 366–369).

A HaeIII fragment was generated as shown (FIG. 16) and size selected from polyacrylamide gels as described in Maniatis et al. supra, at pp. 173-175. This fragment of 266 bp was then cloned into YEp-α-8, as described above, to generate expression vector YEpα-NF-5. This insert, in the correct orientation, encodes a 33 amino acid peptide containing the sequence for rANVP(121-152), with an additional phenylalanine at the Amino-terminus. As a control, the reverse orientation of the insert was cloned into YEp-α-8 and designated YEp-α-NF-7. This insert would encode an unrelated protein having a sequence of different amino acid. Similarly, an AccI fragment of 623 bp was isolated and cloned, in its correct orientation, into YEp-α-8, yielding expression vector YEp-α-NF-9. This insert encodes prorANVP(28-152), with an additional tyrosine at the Amino-terminus. This insert was also cloned in its inverse orientation to generate control plasmid YEp-α-NF12. Insertion of these HaeIII and AccI fragments of rat proANVP cDNA, after the addition of the HindIII linkers, yields DNA sequences coding a chimeric protein. This protein codes for the α-factor signal/leader peptide, a spacer fragment and the desired proANVP sequence.

DNA was prepared from *E. coli* cultures containing these plasmids (Maniatis et al., supra, at pp. 366-369) and used to transform *S. cerevisiae* strain W301-18A (αade 2-1, trp 1-1, leu 2-3, 112, can 1-100, ura 3-1, his 3-11, 15) to Leu 2 prototrophy. Yeast strains were grown on standard media (Sherman et al., Methods in Yeast Genetics, Cold Spring Harbor Press, Cold Spring Harbor, N.Y.). Plasmid DNA from *E. coli* was also re-cloned into M13 for sequencing and confirmation of the α-factor proANVP DNA constructions (Messing J. and J. Vieira, supra).

c) Expression and secretion of rat *proANVP compounds in S. cerevisiae*

The α-factor proANVP fragment processing scheme is shown in FIG. 16. The mRNA transcript is initiated and terminated from the α-factor sequences in the vector. This is translated into a chimeric protein and initiated through the yeast secretory process. Proteolytic processing of this protein occurs both at the Glu-Ala (QA) residues and the Lys-Arg (KR) residues in the α-factor portion of the molecule (Kurjan J. and I. Herskowitz, supra). The Carboxy-terminal portion of this processed protein therefore is the predicted amino acid sequence of rat proANVP.

Cultures of yeast containing these plasmids were maintained in synthetic medium lacking leucine (Sherman et al., supra). This selection is necessary, as yeast plasmids are relatively unstable and lost at approximately 1.0% per generation. Yeast cultures were labeled with 0.1 to 0.5 mCi/ml [$^{35}$S]-methionine (approximately 1000 Ci/mmole) in synthetic medium without leucine for four hours. Bovine serum albumin was added at a final concentration of 100 μg/ml to prevent possible proteolysis. Samples (1.0 ml) were taken and cells were removed by centrifugation. The media proteins were concentrated by 10% TCA precipitation at 4° C. for 15 minutes and subsequent centrifugation in an Eppendorf microfuge (15,000×g). The resulting pellet was washed with acetone, dried under vacuum and resuspended in SDS sample buffer (Laemlli, U.K., Nature 227:680-685 (1970)). These samples were applied directly to an SDS-PAGE gel (17.5% acrylamide) to examine the pattern of total secreted [$^{35}$S]-Met proteins by autoradiography of the dried gel. As can be seen in FIG. 16A, culture supernatants from yeast cultures containing YEp-α-NF-9 showed [35S]-Metlabeled bands at approximately 11.I and 9.4 kd (lanes 3 and 4) while media from cultures of YEp-α-NF-12 (the inverse construction) showed a [$^{35}$S]-Met-labeled band at approximately 5 kd (lanes 5 and 6). Neither of these bands were detected in media from cultures containing the plasmid vector YEp-α-8 (lanes 1 and 2).

The molecular weights of the proteins whose synthesis and secretion is directed by YEp-α-NF-9 are indicate that an endogenous yeast protease may cleave the ANVP peptide from the proANVP precursor encoded by the AccI fragment in this plasmid. To confirm this possibility, yeast cultures harboring this plasmid, its corresponding inverse orientation (YEp-α-NF-12), and yeast cultures which harbor YEp-α-NF-5 and YEp-α-NF-7 (the HaeIII fragment encoding the small fragment of proANVP) were labeled as above with both [$^{35}$S]-methionine and [$^{35}$S]-cysteine to determine if they expressed [$^{35}$S]-labeled proteins which could be specifically immunoprecipitated. The [$^{35}$S]-Met will be incorporated into proANVP protein but not rANVP(126-150), while [$^{35}$S]-Cys is selectively incorporated into rANVP(126-150). Since control experiments suggested that some yeast media components prohibited direct immunoprecipitation, a novel partial purification scheme was performed as follows.

Cells were removed by centrifugation and the cell-free supernatant was used either directly or concentrated by lyophilization. Ten volumes of acetone were added to the aqueous solution and the mixture was allowed to precipitate on ice for 10-15 minutes. The precipitate was then pelleted by centrifugation, and the acetone was removed. A small amount of water (no more than 1 volume) was added to this pellet to facilitate resuspension. Ten volumes of methanol were then added to this mixture, extensively mixed, and the precipitate was collected by centrifugation. The supernatant was then removed and dried under vacuum. This pellet was resolubilized in 1.0 ml of immunoprecipitation buffer and immunoprecipitated and washed as described in Section IV.A.2.

As shown in FIG. 17B, the complexity of proteins as determined after the above extraction procedure is relatively simple compared with the complexity of total secreted protein. Lanes 1 and 2 in FIG. 17B show the secreted [$^{35}$S]-Cys-labeled protein whose synthesis is directed by YEp-α-NF-7 and YEp-α-NF-5, respectively, in the methanol soluble fraction. Lanes 3 and 4 in FIG. 17B show the same proteins following immunoprecipitation, in each case with anti-ANVP IgG. The antiserum appears to specifically precipitate a 3,000 Dalton protein from YEp-α-NF-5 (lane 4, FIG. 17B) while no protein was precipitated from the corresponding inverse orientation (YEp-α-NF-7) (lane 3, FIG. 17B). Lanes 5 and 6 show a similar immunoprecipitation of [$^{35}$S]-Cysteine labeled proteins appearing in the methanol soluble fraction of media conditioned by yeast cultures harboring plasmids YEp-α-NF-12 and YEp-α-NF-9, respectively. The result is the same as shown for lanes 3 and 4, FIG. 17B, and a 3,000 Dalton protein was specifically immunoprecipitated from media conditioned by *S. cerevisiae* containing YEp-α-NF-9.

The results indicate that both yeast expression plasmids, YEp-α-NF-5 and YEp-α-NF-9, direct the synthesis of a 3 kd [$^{35}$S]-Cys-labeled protein (approximately 25-30 amino acids in length) which is immunoprecipitated by specific anti-ANVP IgG.

*S. cerevisiae* strain W301-18A containing YEp-α-NF-9 was deposited with the ATCC on May 31, 1984 and accorded accession number 20710.

d) Expression and Secretion of Human ANVP(128-151) in *S. cerevisiae* i. Construction of PJCl-5 Expression Vector

Plasmid YEp-α-8 (Section IV.B.2.b.) was digested to completion with HindIII, followed by purification of the largest of the restriction fragments by agarose gel electrophoresis as previously described. The purified DNA was ligated and transformed in *E. coli*. Plasmid DNA containing only one HindIII restriction site was purified and designated pJJ-1 (FIG. 18A).

Plasmid pJJ-1 was digested to completion with PstI and SalI, followed by the purification of a 317 bp DNA fragment by agarose gel electrophoresis. The PstI-SalI fragment was ligated to similarly digested plasmid M13-mp8 (Messing, J. and Vieria, J., supra). Single stranded recombinant phage M13 DNA, designated MP-JJ1, was isolated and used as the template for oligodeoxynucleotide-mediated, site-directed mutagenesis (Zoller, M. J. and Smith, M., Methods in Enzymology 100:468-500 (1983)) utilizing the mutagenic oligodeoxynucleotide 5'-GAAGAAGGGGGTAAGCTT-GGATAAAAGAG-3'. The resulting mutagenesis changed the nucleotide codon -TCT-, present at position 241-243 in the coding region of the α-factor gene (Kurjan, J. And Herskowitz, I., supra), to AGC, which introduces a HindIII restriction site at this position but does not change the amino acid (Serine) encoded by this codon (FIG. 18A). The mutagenized recombinant MP-JJ-1 was designated MP-JJ-5.

Plasmid JJ-1 was partially digested with PstI in the presence of ethidium bromide, followed by phenol/chloroform extraction and ethanol precipitation. The DNA was digested to completion with HindIII, followed by calf intestinal phosphatose treatment and the purification of the largest of the restriction fragments by agarose gel electrophoresis.

The replicative from of MP-JJ-5 was digested with PstI and HindIII, followed by isolation of a 220 bp DNA fragment by polyacrylamide gel electrophoresis. The 220 bp PstI-HindIII DNA fragment was ligated to the similarly digested pJJ-1 and transformed into *E. coli*. The resulting plasmid, containing PstI-HindIII restriction fragments of 5853, 2280, 993, 780 and 220 bp, was purified and designated pJCl-5 (FIG. 18A).

ii. Construction of plasmid pJC-2 containing a synthetic DNA sequence encoding hANVNP(1-28-151)

The synthetic DNA sequence shown in FIG. 18B was designed with the set of preferred yeast codons derived from the codon usage in the highly expressed yeast genes encoding the glycolytic enzymes.

The eight oligodeoxynucleotides shown in FIG. 18B were assembled as described in Section IV.A.1.b. Following ligation, the mixture of DNA was digested with HindIII, followed by the purification of a 103 bp fragment by polyacrylamide gel electrophoresis. The purified DNA fragment was ligated into HindIII digested M13-mp18 and M13-mp19 (Vierra, J. and Messing, J., supra) and subjected to dideoxynucleotide sequence analysis as described above (Sanger et al., supra), which resulted in the sequence shown in FIG. 18B.

Plasmid pJCl-5 was digested to completion with HindIII, followed by calf intestinal phosphatase treatment, phenol/chloroform extraction and ethanol precipitation. The purified synthetic DNA sequence described above was ligated to HindIII digested pJCl-5, followed by transformation in *E. coli*. Resultant plasmids were screened for the 103 bp synthetic HindIII sequence, of which one was purified and designated pJC-2. Plasmid pJC-2 encodes the α-factor signal/leader peptide (Kurjan, J. and Herskowitz, I., supra) with an inframe fusion of the human AVNP(128-151) starting after amino acid 85 of the α-factor precursor. The presence of the α-factor regulatory and secretory sequences upstream of the AVNP peptide permits proteolytic processing by the protease encoded by the KEX2 locus (Julius, D. et al., Cell 37 1075-1089 (1984)) following the -Lys-Arg- residues at positions 84 and 85 (FIG. 18B), respectively, and the extracellular secretion of hAVNP(128-151), similar to the secretion described in Section IV.b.1.c. for rat pro-AVNP sequences. Plasmid pJC-2 was used to transform *S. cerevisiae* W301-18A (Section IV.B.1.b.) which was maintained on selective media.

iii. Expression and Purification of Human ANVP(128-151) sequence from *S. cerevisiae*

*S. cerevisiae* W301-184 containing plasmids pJCl-5 or pJC-2 were grown at 30.C in selective synthetic medium as previously described (Section IV.B.1.c.) to stationary phase of growth, at which time the cells were removed by centrifugation at 4.C. The resulting supernatant was removed and assayed for the presence of the ANVP peptide by specific radioimmunoassay (Section V). The results, shown in Table IX, demonstrate that S. cerevisae containing plasmid pJC-2 are secreting immunoreactive peptide.

TABLE IX

| Immunoreactive Peptide | (mg/l of culture) |
|---|---|
| pJCl-5 | 0.0 ± 0.03 |
| pJC-2 | 0.57 ± 0.10 |

To positively identify the immunoreactive peptide, *S. cerevisae* containing plasmid pJC-2 were grown at 30° C. in one liter of selective synthetic media to stationary phase. The cells were removed by centrifugation. The resulting supernatent was adjusted to pH 8.0 with ammonium hydroxide, followed by centrifugation. The resulting cleared supernatent was applied to a 2.5 cm×10 cm column containing DEAE ® Sephacel ® (Pharmacia), previously equilibrated with 0.01 M ammonium acetate, followed by the collection of the eluate (approximately 1.1 l) and lyophilization. The dried mixture was resuspended in approximately 12 ml of 0.5 M acetic acid and applied to a 2.5 cm×50 cm column containing Sephadex ® G-10, equilibrated with the resuspension solution. Fractions containing immunoactivity as assayed by radioimmunoassay (Section V) were collected, pooled and lypholized.

The dried material was resuspended in 5 ml of acetic acid and submitted to HPLC as described in Section IV.A.5.

The immunoreactive peak fraction was isolated and a 200 pmole sample was submitted to automated amino acid sequence analysis as described (Section IV.A.5.). The resulting amino acid sequence was:

H-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH

In addition, contaminants due to yeast peptides were not detected by this method of analysis.

*S. cerevisiae* strain W301-18A containing pJC2 was deposited with the ATCC on April 9, 1985 and accorded accession number 20754.

C. Expression of pre-proANVP Compounds in Cultured Chinese Hamster Ovary Cells In the examples that follow, the expression of pro-rANVP(25-152) and prohANVP(26-151) in CHO cells is described. These examples are provided by way of illustration and it will be readily understood that any pre-proANVP, proANVP, or ANVP compound can be expressed in mammalian cells in a similar manner.

1) Expression of Rat pre-proANVP Compounds

To facilitate the expression of rat pre-proANVP compounds in mammalian cells, a hybrid gene was constructed, in which the coding segment for rat pre-proANVP was fused to a powerful regulated promoter derived from the human metallothionein II (hMTII) gene. This was performed in two steps.

First, an expression vector was prepared. The expression vector, pHSI, carries 840 nucleotide base pairs of hMTII sequence (Karin, M. et al., Nature 99:797-802 (1982)) from a naturally occuring HindIII restriction site at base −765 at the start of transcription to base +70, located in the 5'-untranslated region adjacent to the coding region. Plasmid pHSI also carries a region into which coding sequences may be inserted. To construct pHSI, the plasmid p84H, which carries the hMTII gene, was digested to completion with BamHI, followed by treatment with Bal-31 to remove terminal nucleotides. Following digestion with HindIII, the products of this reaction were ligated into plasmid pUC8 (Vieira, J. and J. Messing, Gene 19:259-268 (1982), which had been opened with HindIII and HincII digestion. One of the resulting plasmid recombinants had the composition of pHSI as determined by nucleotide sequencing.

To complete the construction of the hybrid gene, the EcoRI-SalI rat pre-proANVP cDNA was isolated from plasmid pNF1 (Section II.A.) by digestion with EcoRI and SalI, followed by polyacrylamide gel purification. pHSI was opened with EcoRI and ligated to the cDNA fragment with T4-DNA ligase. The reaction products were then incubated with the four nucleotide triphosphates and DNA polymerase I (Klenow fragment), in order to create blunt-ended molecules which were then subjected to a second ligation to allow recirculization. The recombinant plasmid molecules were introduced into *E. coli* MC1061 and screened by restriction endonuclease analysis (Maniatis et al., supra at p. 104). Two recombinants, pMT-NF1-10 and pMT-NF1-20 (FIG. 19A), were introduced into the chinese hamster ovary (CHO) line of cultured cells by co-transformation with pSV2:NEO (Southern, P. and P. Berg, J. Mol. Appl. Genet. 1:327-341 (1982)), a plasmid carrying a functional gene conferring resistance to the neomycin analogue G418. 500 ng of pSV2:NEO and 5 µg of pMT-NF1-10 or pMT-NF1-20 were applied to a 60 mm dish of cells in a calcium phosphate-DNA coprecipitate according to standard protocols (Wigler, M., et al., Cell 16:777-785 (1979)) with the inclusion of a two minute "shock" with 15% glycerol after 4 hours exposure to the DNA. One day later, the cells were subjected to exposure to G418 at 1 mg/ml. This procedure yielded a pool of G418 resistant colonies, most which had also acquired stable inheritance of pMT-NF1-10 or pMT-NF1-20.

Previous experience with CHO cells, and other cultured cells (McCormick, F. et al., *Molecular and Cellular Biology* 4-1 p.166 (1984)), indicates that they are able to cleave the signal peptide from mammalian prehormones and are able to secrete the remainder of the peptide into the nutrient medium. Accordingly, the production of pre-proANVP compounds is demonstrated by incubating the cells with [$^{35}$S]-methionine and examining the radiolabeled secreted products by standard protein gel analysis.

Autoradiograms of [$^{35}$S]-Met-labeled proteins secreted into the media reveal the appearance of a 18,000 dalton protein that is specifically immunoprecipitated by anti-ANVP IgG. This protein is not seen in [$^{35}$S]-Met-labeled proteins of cells containing a control plasmid. Thus CHO cells containing pMT-NF-1-10 secrete proANVP compounds into the media of these cells.

Chinese Hamster Ovary (CHO) cells containing pMT-NF1-10 were deposited with the ATCC on May 31, 1984 and accorded accession number CRL 8569.

2) Expression of Human pre-proANVP compounds in cultured mammalian cells

Human pre-proANVP compounds were expressed in a manner similar to rat proANVP compounds, with appropriate modifications to account for the features of the human genomic clone. Briefly, a plasmid, pHGRB1, carrying the BamHI to EcoRI human genomic segment spanning the pre-proANVP gene, was constructed, then partially digested with AccI and completely digested with EcoRI. The resulting AccI-EcoRI fragment was isolated by polyacrylamide gel purification. This fragment, which extends from the 5' untranslated region to a point past the 3' end of the gene, was ligated to the expression plasmid pMT401, which was opened with AccI and EcoRI. Plasmid pMT401 was derived by insertion of the BamHI-bounded polylinker region from M13mp7 (Vieira and Messing, supra) into the BamHI site of pHSI. The resulting recombinant, containing the human pre-proANVP gene positioned 3' from the human metallothionein promoter, was designated pHNF-8. The hybrid construction pHNF-8 was then introduced into cultured CHO cells for expression in a manner similar to that described above for rat pre-proANVP compounds.

Cultured CHO cells, which were transformed with pHNF-8, were subcloned by plating cells at low dilutions in dishes containing Harris F-12 medium supplemented with 10% fetal calf serum. Individual subclones were subsequently removed and each examined for pro-ANVP production by both radioimmunoassay (Section V) and radiolabeling with [$^{35}$S]-methionine. The [$^{35}$S]-Met-labeled proteins were resolved by SDS-polyacrylamide gel electrophoresis.

As shown in FIG. 19B, lanes 3–6, patterns of [$^{35}$S]-methionine-labeled proteins from four subclones containing pHNF-8, designated CHO 8/2-6, CHO-8/2-55, CHO-8/2-81, CHO-8/2-93, respectively, contain distinct bands at 18,000 and 10,000 daltons. The bands were identified as proANVP (18,000 k) and a proANVP fragment comprising the Amino-terminus of proANVP, by immunoprecipitation with specific antibodies. Lane 2 contained [$^{35}$S]-Met-labeled proteins from control CHO cells and lane 1 shows [$^{35}$S]-methionine-labeled proteins from a CHO pool transformed with pHNF-8 prior to subcloning. The fact that the subclones are producing proANVP was confirmed by radioimmunoassay as described in Section V.

It should be noted that the 10,000 dalton form implies that a substantial portion of proANVP is being cleaved by proteolysis in this system. Such a proteolytic event yields the Amino-terminal portion (10,000 k) and smaller Carboxy-terminal fragments containing shorter ANVP compounds. Thus, the clones are considered useful for producing proANVP and smaller compounds.

Chinese Hamster Ovary (CHO) cells containing pHNF-8 and designated CHO-8/2-81 were deposited with the ATCC on April 9, 1985 and accorded accession number CRL-8782.

D. Biological Activity of Expression Products Derived from pre-proANVP and proANVP Compounds Various rat and human proANVP and ANVP compounds, whose expression and secretion are directed by the yeast α-factor system described in Section D.2 and the E. coli system described in Section C.2 above, possess biological activity.

Yeast cultures (100 ml) were grown in synthetic media containing 100 µg/ml HSA for 16 hours at 30° C. The cells were removed by centrifugation and the media was lyophilized. The lyophilized powder was reconstituted in 2 ml of distilled $H_2O$ and 10 volumes of acetone were added. The solution was thoroughly mixed and then centrifuged at $10,000 \times g$ for 10 minutes in a Sorvall RT6000 centrifuge (Sorvall Instruments, Wilmington, Del.). After removal of the supernatant, the pellet was resuspended in 1 ml of distilled $H_2O$ and 10 volumes of methanol added. This solution was thoroughly mixed and again centrifuged at $20,000 \times g$ in a Sorvall RC5B centrifuge for 10 minutes. One-half of the solution was dried by rotary evacuation on a Savant-type evaporator ("methanol soluble" fraction; see Table I). The remaining solution was diluted 1:1 with 0.5 M acetic acid and applied to a 3 ml column of SP-Sephadex ® (Sigma Chemical Co.) equilibrated in 0.5 M acetic acid. The column was washed with 15 ml 0.5 M acetic acid and then eluted with 6 ml of 1.0 M ammonium acetate. The eluted material was then dried by lyophilization ("post SP- Sephadex" fraction of Table X).

The dried methanol soluble and ammonium acetate eluted material was resolubilized in 0.5 ml of distilled $H_2O$ and tested for biological activity using the precontracted rabbit thoracic aortic ring model described in Kleinert, et al., Hypertension 6:Suppl. 1:143–146 (1984). Equal volumes of material reconstituted from crude lyophilized media, methanol soluble protein or protein eluted from SP-Sephadex ® with 1.0 M ammonium acetate were compared using aortic rings precontracted with 5 µM histamine. Material synthesized by yeast cultures whose plasmids encoded proANVP (amino acids 26-152) (YEp-α-NF-9) and proANVP (amino acids 121-152) (YEp-α-NF-5), as well as the corresponding inverse orientations (YEp-α-NF-12 and YEp-α-NF-7, respectively), were compared. The results are depicted in Table X.

TABLE X

Vasorelaxant Properties of ProANVP Compounds Expressed by S. cerevisiae

| Media Sample | | % Relaxation |
| --- | --- | --- |
| YEp-α-NF-5 | (methanol soluble) | 100.0 |
| YEp-α-NF-5 | (post SP-Sephadex) | 65.5 |
| YEp-α-NF-7 | (methanol soluble) | 11.7 |
| YEp-α-NF-7 | (post SP-Sephadex) | 3.3 |
| YEp-α-NF-9 | (methanol soluble) | 71.2 |

TABLE X-continued

Vasorelaxant Properties of ProANVP Compounds Expressed by S. cerevisiae

| Media Sample | | % Relaxation |
| --- | --- | --- |
| YEp-α-NF-9 | (post SP-Sephadex) | 48.2 |
| YEp-α-NF-12 | (methanol soluble) | 13.2 |
| YEp-α-NF-12 | (post SP-Sephadex) | 6.5 |

Aortic rings were precontracted with 5 µM histamine. The aortic rings were then treated with proteins obtained from S. cerevisiae cultures. The proteins were purified by acetone/methanol treatment of culture media and the indicated fractions were passed over SP-Sephadex. YEp-α-NF-5 and YEp-α-NF-9 contained proANVP cDNA in its correct orientation and YEp-α-NF-7 and YEp-α-NF-12 contained DNA in an inverse orientation. Data are expressed as percent relaxation of the precontracted rings as described in Kleinert, supra.

Significant vasodilatory activity was detected in the methanol soluble material as well as the post SP-Sephadex material in extracts from cells containing YEp-α-NF-5 and YEp-α-NF-9. Extracts from cells containing inverse orientation DNA plasmids were not active. This finding, as well as the immunoprecipitation data shown in FIG. 17, demonstrates that yeast process full-length proANVP and smaller ANVP compounds into a form that exhibits potent biological activity.

Samples of the above expressed material were also tested for natriuretic and diuretic activity using the isolated perfused rat kidney model as described by Camargo, M. et al., Am. J. Physiol. 246:F447–F456(1984).

TABLE XI

Effects of ANVP Compounds Expressed and Secreted by S. cerevisiae on Renal Function in the Isolated Perfused Rat Kidney

| | Control | YEp-α-NF-5 | YEp-α-NF-7 |
| --- | --- | --- | --- |
| Urinary Sodium (µEq/min) | 3.56 | 11.05 | 3.78 |
| Urinary Volume (µl/min) | 6.15 | 14.0 | 7.24 |

Results represent the average of two ten minutes control periods followed by the addition of 50 µl of SP-Sephadex ® purified protein. Experimental measurements represent the average of values obtained during three successive ten minute periods.

As shown in Table XI, material synthesized and secreted by yeast cultures containing YEp-α-NF-5, and purified as described above through the SP-Sephadex ® step, increased urinary $Na^+$ excretion approximately 3-fold and increased urinary volume 2-fold, as determined during repeated test periods of 10 minutes each. Glomerular filtration also increased in this test, consistent with the diuretic action. No significant increase in urinary $Na^+$ excretion, urinary volume, glomerular filtration or renal resistance was detected when the same test was performed on material synthesized and secreted by yeast cultures containing the reverse orientation control plasmid YEp-α-NF-7 and purified through SP-Sephadex ®.

The hANVP(128–151), purified as described in Section IV.B.2.d., was tested as described above and displayed the full range of biological activities.

In a manner similar to the yeast-expressed active material, rat and human pre-proANVP, proANVP and ANVP compounds expressed by the bacterial and mammalian cell expression systems described in Section IV.A and IV.C, respectively, have been shown to possess biological activity.

The rat proANVP compounds rANVP(87–152) and rANVP(26–152), whose syntheses were directed by plasmids pRNF-6852 and pRNF-12852, respectively, in E. coli, were extracted from 1 liter of bacterial cells as follows. The cells were collected by centrifugation at 5,000×g for 60 minutes and resuspended in 10 ml of 50 mM Tris, pH 7.5. This suspension was sonicated for 1 minute using a Heat Systems ultrasonic sonicator (Heat Systems, Farmingdale, N.Y.) at setting 4. The sonicate was then centrifuged at 105,000×g to remove particulate matter and the resulting supernatant was saved and called crude bacterial extract.

A fraction of the crude bacteria extract was subsequently boiled for 5 minutes and lowered to pH 2.5 for 1 hour. The pH was then neutralized and both the resulting boiled-acid extract and crude bacterial extract were applied to rabbit thoracic aortic rings as described. The results are displayed in Table XII.

TABLE XII

| Vasorelaxant Activities of ProANVP Compounds Expressed in E. coli | |
|---|---|
| Sample | % Relaxation |
| Control (pKT52) | 8 ± 2 |
| prorANVP(87-152) | 74 ± 8 |
| prorANVP(25-152) | 65 ± 9 |

Rabbit thoracic aortic rings were precontracted with 5 μM histamine. Data are expressed as the % relaxation of the precontracted rings.

As shown in Table XII, both the crude bacterial extracts and boiled-acid extracts from bacterial samples containing pRNF-6852 and pRNF-12852 relaxed the precontracted tissue. Control samples from bacteria containing the pKT52 vector without proANVP DNA were inactive. Thus, in a manner similar to the yeast expression products, the bacterial rat proANVP compounds were demonstrated to have vasodilatory activity. Furthermore, since a fraction of these samples were boiled and acid-extracted, to prevent subsequent processing, without a loss of biological activity relative to the crude bacterial extract, it appears that the entire 68 amino acid compounds were biologically active.

Purified human proANVP(26-151), prepared from E. coli as described in Section IV.A.5, was shown to have a profound effect on vascular tissue.

In the case of mammalian cell expression, both pro-rANVP(25-152) and hANVP(126-151) produced in CHO cells exhibited biological activity similar to that observed above.

The proANVP compounds expressed using the above described recombinant DNA techniques in yeast, bacteria and mammalian cells all contain the common ANVP sequence:

H—Arg—Ser—Ser—Cys—Phe—Gly—Gly—Arg—

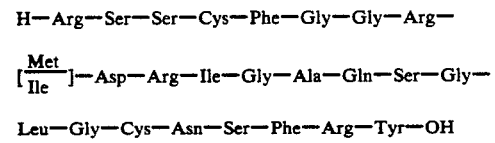

Leu—Gly—Cys—Asn—Ser—Phe—Arg—Tyr—OH where the bracketed amino acid residue is Met in human ANVPs and Ile in rat ANVPs. The proANVP compounds expressed in the systems described above show potent vasorelaxant, natriuretic and diuretic activities (Tables X, XI and XII). These same and related activities have also been demonstrated with rANVP(126-150) and hANVP(127-151). Thus, these expressed fragments should share all properties with a synthetic ANVP, both on in vitro preparations and when injected in vivo into humans or animals. As shown in Table VIII, synthetic ANVPs lowered mean arterial blood pressure, plasma renin activity and plasma aldosterone, and increased urine volume and urine sodium excretion. These are desirable properties for diuretic and antihypertensive agents. Furthermore, proANVP and ANVP compounds act at all major foci of volume and blood pressure regulation. Thus, it can be concluded that pre-proANVP, proANVP, and ANVP compounds, when produced by recombinant DNA methods and expressed in yeast, bacteria or mammalian cells in a manner comparable to that described above, will find utility in the acute and chronic treatment of edematous states (i.e., congestive heart failure, nephrotic syndrome, hepatic cirrhosis and ineffective renal perfusion) and in the chronic treatment of renal insufficiencies and hypertension.

As demonstrated in the above examples, the methods and compositions disclosed can find use in expressing pre-proANVP, proANVP and ANVP compounds. It is apparent to one having ordinary skill in the art that any sequence or fragment of peptide disclosed herein can be expressed by employing minor modifications to this disclosure, while remaining within the scope of the invention.

In particular, any fragment of the pre-proANVPs amino acid sequence disclosed can be expressed. Certain of these fragments will not contain the complete sequence of rANVP(126-150) or hANVP(127-151), but may contain portions of these ANVP compounds. These fragments can themselves demonstrate biological activity comparable with or complementary to the activities disclosed for the instant compounds. Alternatively, they can serve as intermediates for the production of biologically active ANVP compounds.

In addition, human-derived proANVP, fragments thereof and hANVP compounds contain a single amino acid replacement, compared to the biologically active rat-derived peptides. Therefore yeast, bacterial and mammalian cell expressed human-derived compounds, prepared in the manner previously described, will display similar biological activity.

V. PRODUCTION OF ANTIBODY TO ATRIAL NATRIURETIC/VASODILATOR PEPTIDE COMPOUNDS

Compounds of the present invention were used to provide immunoassays, particularly radioimmunoassays, for the determination of the presence or amount of ANVP compounds in samples.

Antibody to ANVP compounds was produced by immunizing New Zealand white rabbits subcutaneously and intramuscularly with 250 μg rANVP(126-150) conjugated to bovine serum albumin in complete Freund's adjuvant. Immunized rabbits were boosted at three week intervals with an identical quantity of conjugate in incomplete Freund's adjuvant. The rabbits were bled from the ear artery 7-10 days after a boost and the resulting serum was tested for its ability to bind ANVP compounds. Parallel control non-immune serum samples were also tested. Table VIII presents data from a representative experiment in which the ability of antisera to interact specifically with ANVP compounds was determined. Five Hundred ng of rANVP(126-150) was immobilized in individual wells of a polystyrene plate. Varying dilutions of antisera were then added to these wells and the amount of antibodies specifically bound was quantified by adding [$^{125}$I]-labeled sheep anti-rabbit IgG antisera. This is a standard method for determining specific antibody titres. As shown in Table XIII, at a serum dilution of 1:400 significant quantities of antibody continued to bind to ANVP compounds. Specific binding was not observed with non-immune serum.

TABLE XIII

Specific Binding of Anti-ANVP Antisera to Immobilized ANVP Compounds

| Antiserum Dilution | Antibody Bound (CPM) | |
|---|---|---|
| | Immune | Non-Immune |
| 1:10 | 7481 | 734 |
| 1:50 | 6977 | 681 |
| 1:100 | 6135 | 685 |
| 1:200 | 5096 | 634 |
| 1:400 | 3898 | 525 |

Table XIV presents data from tests identical to those of Table XIII, however, varying concentrations of non-immobilized ANVP compounds were added concurrently with a 1:100 dilution of anti-ANVP antiserum.

TABLE XIV

Competitive Displacement of ANVP Compound Binding To Immobilized ANVP Compounds by Addition of Free ANVP Compounds

| Conc. Free ANVP (nmoles) | Antibody Bound (CPM) |
|---|---|
| 0 | 6777 |
| 0.002 | 6343 |
| 0.02 | 5603 |
| 0.2 | 2893 |
| 2.0 | 1223 |

As shown, non-immobilized ANVP compounds competitively displaced antibody binding from immobilized ANVP compounds. Thus, this demonstrates a competitive displacement assay. This assay and similar radioimmunoassays, can be used to quantify ANVP-like immunoreactivity in tissues or serum under a variety of physiological or pathophysiological states. Thus far, the assay has been used to detect ANVP compounds in atrial extracts. ANVP compounds were not detected in ventricular extracts.

Although the foregoing invention has been described in some detail by way of clarity and for purposes of understanding, it will be understood by those skilled in the art that modifications of the invention may be practiced while remaining within the spirit and scope of the appended claims.

We claim:

1. A polypeptide compound useful as a natriuretic, diuretic, and/or vasodilator in mammals, said polypeptide compound having the formula:

$$\overset{1}{X—Arg}—\overset{2}{Ser}—\overset{3}{Ser}—\overset{4}{Cys}—\overset{5}{Phe}—AA_6—AA_7—\overset{8}{Arg}—AA_9—\overset{10}{Asp}—\overset{11}{Arg}—AA_{12}—AA_{13}—\overset{14}{Ala}—\overset{15}{Gln}—\overset{16}{Ser}—AA_{17}—\overset{18}{Leu}—\overset{19}{Gly}—\overset{20}{Cys}—Y \quad (1)$$

wherein

X is hydrogen, acetyl, or an oligopeptide of up to 125 amino acid residues from the naturally occurring N-terminal Atrial Peptide Sequence, including the N-acetyl derivatives thereof;

Y is hydroxyl, amido, Asn-OH, Asn-Ser-OH, Asn-Ser-Phe-OH, Asn-Ser-Phe-Arg-OH, Asn-Ser-Phe-Arg-Tyr-OH, or the C-terminal amide derivatives thereof; or an oligopeptide extension of up to 20 amino acid residues from the C-terminus of any of the foregoing, including the C-terminal amide derivatives thereof;

each of $AA_6$, $AA_7$, $AA_{13}$, and $AA_{17}$, is independently selected from the group consisting of Gly and Ala; $AA_9$ is selected from Ile, met, and Val; and $AA_{12}$ is selected from Ile and Val, wherein 0, 1 or 2 residues selected from residues 1-20 are substituted by the D-isomer thereof, and including such compound containing a disulfide bridge joining the cysteine residues and the pharmacologically acceptable salts thereof, and which compound contains at least one of the following substitutions for residues in formula (1):

des—Ser at position 2 or 3;
Ala or Leu in place of Phe at position 5;
Nle in place of Arg at position 8; and
Nle in place of Arg at position 11.

* * * * *